(12) United States Patent
Pigge et al.

(10) Patent No.: US 11,851,447 B2
(45) Date of Patent: Dec. 26, 2023

(54) DINUCLEAR PLATINUM(II) COMPOUNDS AND METHODS OF USE THEREOF

(71) Applicant: UNIVERSITY OF IOWA RESEARCH FOUNDATION, Iowa City, IA (US)

(72) Inventors: Christopher Pigge, Iowa City, IA (US); Moustafa Tarek Ahmed Ibrahim Gabr, Iowa City, IA (US)

(73) Assignee: UNIVERSITY OF IOWA RESEARCH FOUNDATION, Iowa City, IA (US)

(*) Notice: Subject to any disclaimer, the term of this patent is extended or adjusted under 35 U.S.C. 154(b) by 840 days.

(21) Appl. No.: 16/814,423

(22) Filed: Mar. 10, 2020

(65) Prior Publication Data

US 2020/0308208 A1 Oct. 1, 2020

Related U.S. Application Data

(60) Provisional application No. 62/816,421, filed on Mar. 11, 2019.

(51) Int. Cl.
| | |
|---|---|
| *G01N 21/76* | (2006.01) |
| *C07F 15/00* | (2006.01) |
| *C07H 21/04* | (2006.01) |
| *G01N 21/359* | (2014.01) |
| *C12N 15/11* | (2006.01) |
| *C12Q 1/34* | (2006.01) |
| *C12Q 1/68* | (2018.01) |

(52) U.S. Cl.
CPC ......... *C07F 15/0086* (2013.01); *C07H 21/04* (2013.01); *C12N 15/11* (2013.01); *C12Q 1/34* (2013.01); *G01N 21/359* (2013.01); *G01N 21/76* (2013.01); *C12Q 1/68* (2013.01); *G01N 2333/916* (2013.01)

(58) Field of Classification Search
CPC ..... C07F 15/0086; C07H 21/04; C12N 15/11; C12Q 1/34; C12Q 1/68; G01N 21/359; G01N 21/76; G01N 2333/916
See application file for complete search history.

(56) References Cited

PUBLICATIONS

Gabr, Inorg Chem, 2018, vol. 57, 12641-12649. (Year: 2018).*
Baranovskii, A , et al., "Human Deoxyribonucleases", Biochemistry 69, 587-601 (2004).
Basnakian, A , et al., "Cisplatin nephrotoxicity is mediated by deoxyribonuclease I", J Am Soc Nephrol 16, 697-702 (2005).
Cherepanova, A , et al., "Deoxyribonuclease activity and circulating DNA concentration in blood plasma of patients with prostate tumors", Ann N.Y. Acad Sci 1137, 218-221 (2008).
Cherepanova, A , et al., "Immunochemical assay for deoxyribonuclease activity in body fluids", J Immunol Methods 325, 96-103 (2007).

(Continued)

*Primary Examiner* — D Margaret M Seaman
(74) *Attorney, Agent, or Firm* — Viksnins Harris Padys Malen LLP

(57) ABSTRACT

The invention provides a compound of formula (Ia) or (Ib):

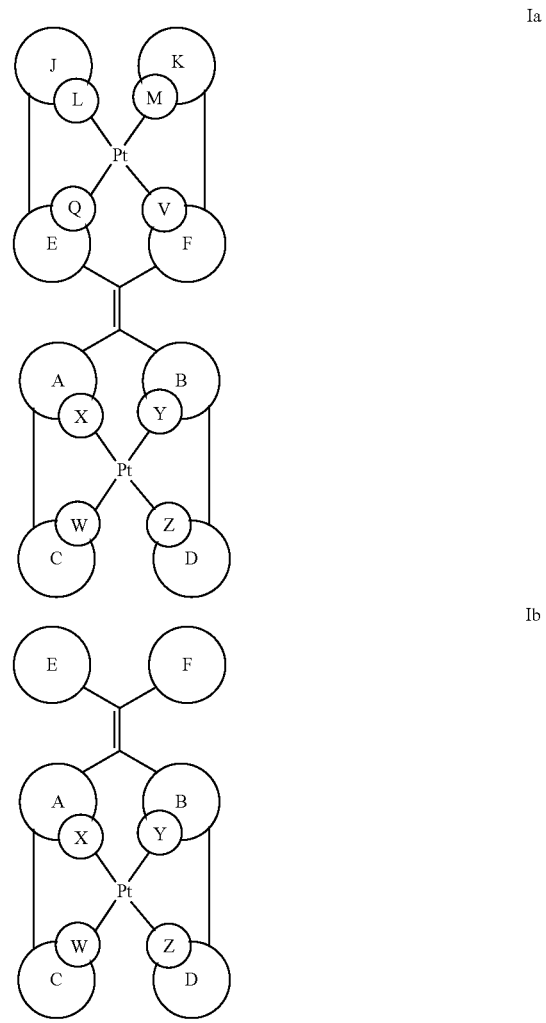

or a salt thereof, wherein A, B, C, D, E, F, J, K, L, M, Q, V, X, Y, W and Z have any of the values described in the specification, as well as compositions comprising a compound of formula (Ia) or (Ib) or a salt thereof, and methods of use thereof.

19 Claims, 41 Drawing Sheets

Specification includes a Sequence Listing.

(56) References Cited

PUBLICATIONS

Choi, S, et al., "Fluorometric Determination of Deoxyribonuclease I Activity with PicoGreen", Anal Biochem 281, 95-97 (2000).

Chyan, W, et al., "Enzyme-Activated Fluorogenic Probes for Live-Cell and in Vivo Imaging", ACS Chem Biol 13, 1810-1823 (2018).

Dou, Y, et al., "Novel high-sensitive fluorescent detection of deoxyribonuclease I based on DNA-templated gold/silver nanoclusters", Anal Chim Acta 784, 53-58 (2013).

Fojta, M, et al., "Cleavage of Supercoiled DNA by Deoxyribonuclease I in Solution and at the Electrode Surface", Electroanalysis 11, 1005-1012 (1999).

Gabr, M, "AIE-Based Probes for Label-Free Biosensing", Thesis Final Defense, The University of Iowa, 25 pages (Mar. 13, 2019).

Gabr, M, et al., "Dinuclear platinum(II) complex with switchable near-infrared emission as a probe of nuclease activity", Abstracts of Papers, 257th American Chemical Society National Meeting, Orlando, FL, INOR-0193, Mar. 31-Apr. 4, 2019.

Gabr, M, et al., "Dinuclear platinum(II) complex with switchable near-infrared emission as a probe of nuclease activity", Poster, American Chemical Society National Meeting, Orlando, FL, Mar. 31-Apr. 4, 2019.

Gabr, M, et al., "Expanding the Toolbox for Label-Free Enzyme Assays: A Dinuclear Platinum(II) Complex/DNA Ensemble with Switchable Near-IR Emission", Molecules 24(23), 4390, 13 pages, Supporting Information, S1-S48 (2019).

Garland, M, et al., "A Bright Future for Precision Medicine: Advances in Fluorescent Chemical Probe Design and Their Clinical Application", Cell Chem Biol 23, 12-136 (2016).

Grimm, J, "The chemistry of small-molecule fluorogenic probes", Prog Mol Biol Transl Sci 113, 1-34 (2013).

Hao, C, et al., "Chiral supernanostructures for ultrasensitive endonuclease analysis", J Mater Chem B, 1, 539-5542 (2013).

Hernandez, L, et al., "Nuclease activity as a specific biomarker for breast cancer", Chem Commun 52(83), 12346-12349 (2016).

Jang, D, et al., "Novel High-Throughput Deoxyribonuclease 1 Assay", J Biomol Screen 20, 202-211 (2015).

Jung, Y, et al., "A signal-on, colorimetric determination of deoxyribonuclease I activity utilizing the photoinduced synthesis of gold nanoparticles", Nanoscale 10, 4339-4343 (2018).

Keyel, P, et al., "Dnases in health and disease", Dev Biol 429, 1-11 (2017).

Lavis, L, et al., "Bright Ideas for Chemical Biology", ACS Chem Biol 3, 142-155 (2008).

Lee, C, "A label-free fluorescent assay for deoxyribonuclease I activity based on DNA-templated silver nanocluster/graphene oxide nanocomposite", Biosens Bioelectron 93, 293-297 (2017).

Morikawa, N, et al., "Serum deoxyribonuclease I activity can be used as a novel marker of transient myocardial ischaemia: results in vasospastic angina pectoris induced by provocation test", Eur Heart J 28, 2992-2997(2007).

Mozioglu, E, et al., "Detection of nuclease activity using a simple fluorescence based biosensor", Anal Methods 8, 4017-4021 (2016).

Nadano, D, et al., "Measurement of Deoxyribonuclease I Activity in Human Tissues and Body Fluids by a Single Radial Enzyme-Diffusion Method", Clin Chem 39, 448-452 (1993).

Pedersen, H, et al., "Lupus nephritis: low urinary DNase I levels reflect loss of renal DNase I and may be utilized as a biomarker of disease progression", J Pathol Clin Res 4, 193-203 (2018).

Samejima, K, et al., "Trashing the genome: the role of nucleases during apoptosis", Nat Rev Mol Cell Biol 6, 677-688 (2005).

Sato, S, et al., "Highly Sensitive Nuclease Assays Based on Chemically Modified DNA or RNA", Sensors 14, 12437-12450 (2014).

Shi, J, et al., "Enzyme-Responsive Bioprobes Based on the Mechanism of Aggregation-Induced Emission", ACS Appl Mater Interfaces 10, 12278-12294 (2018).

Singh, K, et al., "Fluorescent Chemosensors as Future Tools for Cancer Biology", ACS Chem Biol 13, 1785-1798 (2018).

Skiljevic, D, et al., "Serum DNase I activity in systemic lupus erythematosus: correlation with immunoserological markers, the disease activity and organ involvement", Clin Chem Lab Med 51, 1083-1091 (2013).

Sun, S, et al., "A label-free near-infrared fluorescent assay for the determination of deoxyribonuclease I activity based on malachite green/G-quadruplexes", Analyst 138, 2592-2597 (2013).

Yao, J, et al., "Chemistry, biology, and medicine of fluorescent nanomaterials and related systems: new insights into biosensing, bioimaging, genomics, diagnostics, and therapy", Chem Rev 114, 6130-6178 (2014).

Yu, C, et al., "Nucleic acid-induced self-assembly of a platinum(ii) terpyridyl complex: detection of G-quadruplex formation and nuclease activity", Chem Commun 3756-3758 (2009).

Zhang, Q, et al., "One-pot Synthesis of Quencher Labeled Hairpin DNA—CdTe QDs Conjugate for Target DNA and Deoxyribonuclease I Detection", Anal Sci 32, 1035-1037 (2016).

Zhao, C, et al., "DNase-targeted natural product screening based on a sensitive and selective DNase I detecting system", RSC Adv 7, 30911-30918 (2017).

Zheng, Q, et al., "Development of photostable fluorophores for molecular imaging", Curr Opin Chem Biol 39, 32-38 (2017).

Zhou, Z, et al., "G-quadruplex-Based Fluorescent Assay of S1 Nuclease Activity and K+", Anal Chem 85, 2431-2435 (2013).

\* cited by examiner

| | |
|---|---|
| single-stranded DNA (ssDNA) | 5' AAAAAAAAAAAAAAAAAAAAAA 3' |
| double-stranded DNA (dsDNA) | 5' CGCGAATTCGC 3' |
| | 3' GCGCTTAAGCG 5' |
| G-quadruplex DNA (QDNA), QI | 5' (GGGGTTTTGGG)$_2$ 3' |
| QDNA, QII | 5' AGGGTTAGGGTTAGGGTTAGGG 3' |
| QDNA, QIII | 5' TGAGGGTGGGTAGGGTGGGTAA 3' |

SEQUENCE LISTING

```
<160> NUMBER OF SEQ ID NOS: 5

<210> SEQ ID NO 1
<211> LENGTH: 22
<212> TYPE: DNA
<213> ORGANISM: Unknown
<220> FEATURE:
<223> OTHER INFORMATION: Description of Unknown:
      G-quadruplex DNA sequence

<400> SEQUENCE: 1
ggggttttgg gggggttttg gg                                                 22

<210> SEQ ID NO 2
<211> LENGTH: 22
<212> TYPE: DNA
<213> ORGANISM: Homo sapiens

<400> SEQUENCE: 2
agggttaggg ttagggttag gg                                                 22

<210> SEQ ID NO 3
<211> LENGTH: 22
<212> TYPE: DNA
<213> ORGANISM: Homo sapiens

<400> SEQUENCE: 3
tgagggtggg tagggtgggt aa                                                 22
```

```
<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
aaaaaaaaaa aaaaaaaaaa aa                                              22

<210> SEQ ID NO 5
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cgcgaattcg c                                                          11
```

DINUCLEAR PLATINUM(II) COMPOUNDS AND METHODS OF USE THEREOF

RELATED APPLICATION

This application claims priority to U.S. Provisional Patent Application No. 62/816,421 that was filed on Mar. 11, 2019. The entire content of the application referenced above is hereby incorporated by reference herein.

SEQUENCE LISTING

The instant application contains a Sequence Listing which has been filed electronically in ASCII format and is hereby incorporated by reference in its entirety. Said ASCII copy, created on May 11, 2020, is named 17023_228US1_SL.txt and is 1,271 bytes in size.

BACKGROUND

Developing luminescent probes for rapid detection of biomolecules and/or monitoring of biochemical processes is an important objective in contemporary bio-organic chemistry (Lavis, L. D. et al. *ACS Chem. Biol.* 2008, 3, 142-155; Grimm, J. B. et al. *Prog. Mol. Biol. Transl. Sci.* 2013, 113, 1-34; Zheng Q. et al. *Curr. Opin. Chem. Biol.* 2017, 39, 32-38; Garland, M. et al. *Cell Chem. Biol.* 2016, 23, 122-136 and Yao, J. et al. *Chem. Rev.* 2014, 114, 6130-6178). Such probes can provide fundamental insight into mechanistic features of cellular events or function as diagnostic agents in biomedical applications. Additionally, probes for specific biocatalytic transformations are important bioanalytical tools for detection and quantification of enzymatic activity (Chyan W. et al. *ACS Chem. Biol.* 2018, 13, 1810-1823; Singh, K. et al. *ACS Chem. Biol.* 2018, 13, 1785-1798 and Shi, J. et al. *ACS Appl. Mater. Interfaces* 2018, 10, 12278-12294). Significantly, elevated or reduced levels of specific enzyme activity often serve as biomarkers of human disease.

Deoxyribonuclease I (DNAse I) is the most abundant nuclease in human blood plasma. It is a non-restriction endonuclease that cleaves phosphodiester linkages within polynucleotide chains to release shorter oligonucleotides (Baranovskii, A. G.; et al. *Biochemistry* (Moscow) 2004, 69, 587-601; Cherepanova, A. et al. *J. Immunol. Methods* 2007, 325, 96-103; Basnakian, A. G. et al. *J. Am. Soc. Nephrol.* 2005, 16, 697-702; Keyel, P. A. et al. *Dev. Biol.* 2017, 429, 1-11). DNAse I functions as a waste-management nuclease through degradation of circulating DNA released into human serum upon cellular death (Samejima K. et al. *Nat. Rev. Mol. Cell. Biol.* 2005, 6, 677-688). Clinically, DNAse I may also serve as a functional biomarker in monitoring the progression of different human diseases (Cherepanova, A. V. et al. *Ann. N. Y Acad. Sci.* 2008, 1137, 218-221; Pedersen, H. L. et al. *J. Pathol. Clin. Res.* 2018, 4, 193-203; Morikawa, N. et al. *Eur. Heart J.* 2007, 28, 2992-2997; Skiljevic, D. et al. *Clin. Chem. Lab. Med.* 2013, 51, 1083-1091 and Hernandez, L. I. et al. *Chem. Commun.* 2016, 52, 12346-123490). For example, low DNAse activity in blood plasma of prostate cancer patients in comparison to healthy controls was demonstrated (Cherepanova, A. V. et al. *Ann. N. Y Acad. Sci.* 2008, 1137, 218-221). Recently, low urinary DNAse I level was identified as a marker for progression of lupus nephritis (Pedersen, H. L. et al. *J. Pathol. Clin. Res.* 2018, 4, 193-203). In addition, elevated serum DNAse I activity is a valuable marker of acute myocardial infraction and transient myocardial ischemia (Morikawa, N. et al. *Eur. Heart J.* 2007, 28, 2992-2997). The correlation between serum DNAse I activity and immunoserological markers in systemic lupus erythematosus (SLE) patients has been advanced as a means of monitoring SLE progression (Skiljevic, D. et al. *Clin. Chem. Lab. Med.* 2013, 51, 1083-1091).

Conventional methods for assessing DNAse I activity include enzyme-linked immunosorbent assays (ELISA) (Cherepanova, A. et al. *J. Immunol. Methods* 2007, 325, 96-103), single radial enzyme-diffusion methods (Nadano, D. et al. *Clin. Chem.* 1993, 39, 448-452), and electrochemical assays (Fojta, M. et al. *Electroanalysis* 1999, 11, 1005-1012). These methods are time-consuming, labor intensive, and/or require use of covalently labelled DNA. These limitations are partially addressed by luminescence-based DNAse I assays that feature simplicity, sensitivity and ease of operation (Jang, D. S. et al. *J. Biomol. Screen.* 2015, 20, 202-211; Zhao, C.; Chen, Y. et al. *RSC Adv.* 2017, 7, 30911-30918 and Lee, C. Y et al. *Biosens. Bioelectron.* 2017, 93, 293-297). However, these methods often rely on the use of fluorophore-labelled DNA (Sato, S. et al. *Sensors* 2014, 14, 12437-12450; Mozioğlu, E. et al. *Anal. Methods* 2016, 8, 4017-4021; Zhang, Q. et al. *Anal. Sci.* 2016, 32, 1035-1037 and Jung, Y. L. et al. *Nanoscale,* 2018, 10, 4339-4343). The high cost and synthetic challenges encountered in developing fluorophore-labelled DNA probes render label-free assays more convenient and cost-effective alternatives. Most existing label-free DNAse I assays are based on "turn-off" fluorescence signalling, which can lead to reduced sensitivity and false positive responses (Sun, S.-K. et al. *Analyst,* 2013, 138, 2592-2597; Dou Y. et al. *Anal. Chim. Acta* 2013, 784, 53-58; Hao, C. et al. *J. Mater. Chem. B* 2013, 1, 5539-5542; Choi S.-J. et al. *Anal. Biochem.* 2000, 281, 95-97; Zhou, Z. et al. *Anal. Chem.* 2013, 85, 2431-2435 and Yu, C. et al. *Chem. Commun.* 2009, 3756-3758). Consequently, "turn-on" luminescence bioassays are more attractive, but only one label-free turn-on DNAse I assay has been reported. This system, based on DNA-Ag nanocluster composites with graphene oxide, requires multiple steps and prolonged reaction times that restrict its potential utility, especially in high-throughput assays for DNAse I activity (Lee, C. Y. et al. *Biosens. Bioelectron.* 2017, 93, 293-2970).

Accordingly, there is a need for new compounds and methods for the detection DNAse I activity.

SUMMARY OF THE INVENTION

Accordingly the invention provides a compound of formula (Ia) or (Ib):

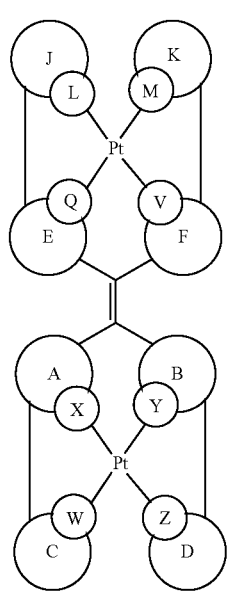

Ia

-continued

Ib

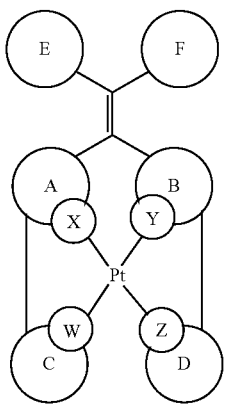

wherein:

A, B, C, D, E, F, J and K are aryl or heteroaryl, wherein the aryl or heteroaryl is optionally substituted with one or more groups that are independently selected from the group consisting of carboxy, hydroxy, halo, aryl, heteroaryl, heterocycle, ($C_1$-$C_6$)alkyl, ($C_1$-$C_6$)alkoxy, ($C_2$-$C_6$)alkenyl, ($C_2$-$C_6$)alkynyl, ($C_1$-$C_6$)alkanoyl, ($C_1$-$C_6$)alkoxycarbonyl, ($C_1$-$C_6$)alkanoyloxy, and ($C_3$-$C_6$)cycloalkyl;

L, M, Q and V are heteroatom or carbon; provided 2 and only 2 of the 4 are nitrogen;

X, Y, W and Z are heteroatom or carbon; provided 2 and only 2 of the 4 are nitrogen; or a salt thereof.

Certain embodiments also provide a method of detecting the presence of DNAse I in a test sample, the method comprising: 1) contacting a composition with the test sample to provide a first reaction mixture; and 2) measuring the NIR emission intensity of the first reaction mixture, wherein an increase in the NIR emission intensity as compared to a control correlates with the presence of DNAse I in the test sample.

Certain embodiments provide a method of detecting the presence of DNAse I in a test sample, the method comprising: 1) measuring the NIR emission intensity of a composition; 2) contacting the composition with the test sample to provide a first reaction mixture; and 3) measuring the NIR emission intensity of the first reaction mixture, wherein an increase in the NIR emission of the first reaction mixture as compared to the NIR emission intensity of the composition correlates with the presence of DNAse I in the test sample.

Certain embodiments also provide a method of identifying a DNAse I inhibitor, the method comprising: 1) contacting a composition, DNAse I and a test compound to provide a first reaction mixture; 2) measuring the NIR emission intensity of the first reaction mixture; and 3) identifying the test compound as a DNAse I inhibitor when a decrease in the NIR emission intensity is detected as compared to a control.

Certain embodiments also provide a method of identifying a DNAse I inhibitor, the method comprising: 1) contacting a composition and DNAse I to provide a first reaction mixture; 2) measuring the NIR emission intensity of the first reaction mixture; 3) contacting a composition, DNAse I and the test compound to provide a second reaction mixture; 4) measuring the NIR emission intensity of the second reaction mixture; and 5) identifying the test compound as a DNAse I inhibitor when the NIR emission intensity of the second reaction mixture is less than the NIR emission intensity of the first reaction mixture.

Certain embodiments also provide a kit comprising: 1) a plurality of compounds of formula (Ia), (Ib) or salts thereof; 2) G-quadruplex DNA; and 3) instructions for detecting the presence of DNAse I in a test sample or identifying a DNAse I inhibitor, using the plurality of compounds of formula (Ia), (Ib) or salts thereof, and the G-quadruplex DNA.

The invention also provides processes and intermediates disclosed herein that are useful for preparing a compound of formula I or a salt thereof.

DETAILED DESCRIPTION

Figure 1:
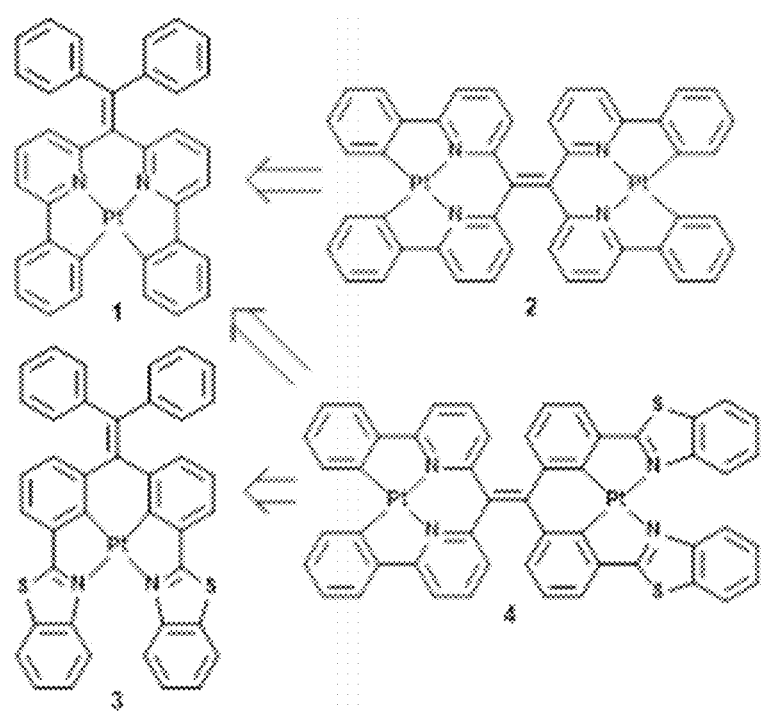
FIG. 1. Structures of Pt(II) complexes 1-4.

Switchable luminescent bioprobes whose emission can be turned on as a function of specific enzymatic activity are emerging as important tools in chemical biology. Described in certain embodiments herein is a platform for the development of label-free and continuous enzymatic assays in high-throughput mode based on the reversible solvent-induced self-assembly of a neutral dinuclear Pt(II) complex. In particular, the Examples describe the switchable luminescence of a dinuclear Pt(II) complex, which was used in developing an experimentally simple, fast (10 min), low cost, and label-free turn-on luminescence assay for the endonuclease enzyme DNAse I. The complex displays a near-IR (NIR) aggregation-induce emission at 785 nm in aqueous solution that is completely quenched upon binding to G-quadruplex DNA from the human c-myc oncogene. Luminescence is restored upon DNA degradation elicited by exposure to DNAse I. Correlation between near-IR luminescence intensity and DNAse I concentration in human serum samples allows for fast and label-free detection of DNAse I down to 0.002 U/mL. The Pt(II) complex/DNA assembly is also effective for identification of DNAse I inhibitors, and assays can be performed in multiwell plates compatible with high-throughput screening. The combination of sensitivity, speed, convenience, and cost render this method superior to other reported luminescence-based DNAse I assays. The versatile response of the Pt(II) complex to DNA structures promises broad potential applications in developing real-time and label-free assays for other nucleases as well as enzymes that regulate DNA topology.

Certain Definitions

The following definitions are used, unless otherwise described: halo or halogen is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to.

The term "alkyl", by itself or as part of another substituent, means, unless otherwise stated, a straight or branched chain hydrocarbon radical, having the number of carbon atoms designated (i.e., $C_{1-8}$ means one to eight carbons). Examples include $(C_1-C_8)$alkyl, $(C_2-C_8)$alkyl, $C_1-C_6)$alkyl, $(C_2-C_6)$alkyl and $(C_3-C_6)$alkyl. Examples of alkyl groups include methyl, ethyl, n-propyl, iso-propyl, n-butyl, t-butyl, iso-butyl, sec-butyl, n-pentyl, n-hexyl, n-heptyl, n-octyl, and higher homologs and isomers.

The term "alkenyl" refers to an unsaturated alkyl radical having one or more double bonds. Examples of such unsaturated alkyl groups include vinyl, 2-propenyl, crotyl, 2-iso-pentenyl, 2-(butadienyl), 2,4-pentadienyl, 3-(1,4-pentadienyl) and the higher homologs and isomers.

The term "alkynyl" refers to an unsaturated alkyl radical having one or more triple bonds. Examples of such unsaturated alkyl groups ethynyl, 1- and 3-propynyl, 3-butynyl, and higher homologs and isomers.

The term "alkoxy" refers to an alkyl groups attached to the remainder of the molecule via an oxygen atom ("oxy").

The term "cycloalkyl" refers to a saturated or partially unsaturated (non-aromatic) all carbon ring having 3 to 8 carbon atoms (i.e., $(C_3-C_8)$carbocycle). The term also includes multiple condensed, saturated all carbon ring systems (e.g., ring systems comprising 2, 3 or 4 carbocyclic rings). Accordingly, carbocycle includes multicyclic carbocyles such as a bicyclic carbocycles (e.g., bicyclic carbocycles having about 3 to 15 carbon atoms, about 6 to 15 carbon atoms, or 6 to 12 carbon atoms such as bicyclo[3.1.0]hexane and bicyclo[2.1.1]hexane), and polycyclic carbocycles (e.g tricyclic and tetracyclic carbocycles with up to about 20 carbon atoms). The rings of the multiple condensed ring system can be connected to each other via fused, spiro and bridged bonds when allowed by valency requirements. For example, multicyclic carbocycles can be connected to each other via a single carbon atom to form a spiro connection (e.g., spiropentane, spiro[4,5]decane, etc), via two adjacent carbon atoms to form a fused connection (e.g., carbocycles such as decahydronaphthalene, norsabinane, norcarane) or via two non-adjacent carbon atoms to form a bridged connection (e.g., norbornane, bicyclo[2.2.2]octane, etc). Non-limiting examples of cycloalkyls include cyclopropyl, cyclobutyl, cyclopentyl, cyclohexyl, bicyclo[2.2.1]heptane, pinane, and adamantane.

The term "aryl" as used herein refers to a single all carbon aromatic ring or a multiple condensed all carbon ring system wherein at least one of the rings is aromatic. For example, in certain embodiments, an aryl group has 6 to 20 carbon atoms, 6 to 14 carbon atoms, 6 to 12 carbon atoms, or 6 to 10 carbon atoms. Aryl includes a phenyl radical. Aryl also includes multiple condensed carbon ring systems (e.g., ring systems comprising 2, 3 or 4 rings) having about 9 to 20 carbon atoms in which at least one ring is aromatic and wherein the other rings may be aromatic or not aromatic (i.e., cycloalkyl). The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. Non-limiting examples of aryl groups include, but are not limited to, phenyl, indenyl, indanyl, naphthyl, 1, 2, 3, 4-tetrahydronaphthyl, anthracenyl, and the like.

The term "heterocycle" refers to a single saturated or partially unsaturated ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems are further described below. Thus, the term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The sulfur and nitrogen atoms may also be present in their oxidized forms. Exemplary heterocycles include but are not limited to azetidinyl, tetrahydrofuranyl and piperidinyl. The term "heterocycle" also includes multiple condensed ring systems (e.g., ring systems comprising 2, 3 or 4 rings) wherein a single heterocycle ring (as defined above) can be condensed with one or more groups selected from cycloalkyl, aryl, and heterocycle to form the multiple condensed ring system. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heterocycle) can be at any position of the multiple condensed ring system including a heterocycle, aryl and carbocycle portion of the ring. In one embodiment the term heterocycle includes a 3-15 membered heterocycle. In one embodiment the term heterocycle includes a 3-10 membered heterocycle. In one embodiment the term heterocycle includes a 3-8 membered heterocycle. In one embodiment the term heterocycle includes a 3-7 membered heterocycle. In one embodiment the term heterocycle includes a 3-6 membered heterocycle. In one embodiment the term heterocycle includes a 4-6 membered heterocycle. In one embodiment the term heterocycle includes a 3-10 membered monocyclic or bicyclic heterocycle comprising 1 to 4 heteroatoms. In one embodiment the term heterocycle includes a 3-8 membered monocyclic or bicyclic heterocycle heterocycle comprising 1 to 3 heteroatoms. In one embodiment the term heterocycle includes a 3-6 membered monocyclic heterocycle comprising 1 to 2 heteroatoms. In one embodiment the term heterocycle includes a 4-6 membered monocyclic heterocycle comprising 1 to 2 heteroatoms. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl, 1,4-benzodioxanyl, spiro[cyclopropane-1,1'-isoindolinyl]-3'-one, isoindolinyl-1-one, 2-oxa-6-azaspiro[3.3]heptanyl, imidazolidin-2-one imidazolidine, pyrazolidine, butyrolactam, valerolactam, imidazolidinone, hydantoin, dioxolane, phthalimide, and 1,4-dioxane.

The term "heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from cycloalkyl, aryl, heterocycle, and heteroaryl. It is to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, triazolyl, tetrazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, and quinazolyl.

The term "alkoxycarbonyl" as used herein refers to a group (alkyl)-O—C(=O)—, wherein the term alkyl has the meaning defined herein.

The term "alkanoyloxy" as used herein refers to a group (alkyl)-C(=O)—O—, wherein the term alkyl has the meaning defined herein.

As used herein, the term "heteroatom" is meant to include oxygen (O), nitrogen (N), sulfur (S) and silicon (Si).

As used herein, the term "protecting group" refers to a substituent that is commonly employed to block or protect a particular functional group on a compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl) ethyl, 2-(trimethylsilyl)ethoxymethyl, 2-(p-toluenesulfonyl) ethyl, 2-(p-nitrophenylsulfenyl)ethyl, 2-(diphenylphosphino)-ethyl, nitroethyl and the like. For a general description of protecting groups and their use, see P. G. M. Wuts and T. W. Greene, Greene's Protective Groups in Organic Synthesis 4$^{th}$ edition, Wiley-Interscience, New York, 2006.

As used herein a wavy line " $\sim\!\!\sim$ " that intersects a bond in a chemical structure indicates the point of attachment of the bond that the wavy bond intersects in the chemical structure to the remainder of a molecule.

The compounds disclosed herein can also exist as tautomeric isomers in certain cases. Although only one delocalized resonance structure may be depicted, all such forms are contemplated within the scope of the invention.

It is understood by one skilled in the art that this invention also includes any compound claimed that may be enriched at any or all atoms above naturally occurring isotopic ratios with one or more isotopes such as, but not limited to, deuterium ($^2$H or D). As a non-limiting example, a —$CH_3$ group may be substituted with -$CD_3$.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities.

When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95% the absolute stereoisomer depicted. In another embodiment, the compound may be at least 99% the absolute stereoisomer depicted.

The term "residue" as it applies to the residue of a compound refers to a compound that has been modified in any manner which results in the creation of an open valence wherein the site of the open valence. The open valence can be created by the removal of 1 or more atoms from the compound (e.g., removal of a single atom such as hydrogen or removal of more than one atom such as a group of atoms including but not limited to an amine, hydroxyl, methyl, amide (e.g., —C(=O)$NH_2$) or acetyl group). The open valence can also be created by the chemical conversion of a first functional group of the compound to a second functional group of the compound (e.g., reduction of a carbonyl group, replacement of a carbonyl group with an amine,)

followed by the removal of 1 or more atoms from the second functional group to create the open valence.

Specific values listed below for radicals, substituents, and ranges, are for illustration only; they do not exclude other defined values or other values within defined ranges for the radicals and substituents. It is to be understood that two or more values may be combined. It is also to be understood that the values listed herein below (or subsets thereof) can be excluded.

Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; $(C_2-C_6)$alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

In one embodiment, a specific value for A, B, C, D, E, F, J and K are aryl or heteroaryl, wherein the aryl or heteroaryl is optionally substituted with one or more groups that are independently selected from the group consisting of carboxy, hydroxy, halo, aryl, heteroaryl, and heterocycle.

In one embodiment, a specific value for A, B, C, D, E, F, J and K are each heteroaryl.

In one embodiment, a specific value for C, D, J and K are each benzothiazolyl.

In one embodiment, a specific value for A, B, E and F are each pyridyl.

In one embodiment, a specific value for formula (Ia), wherein A and B, or C and D, or E and F, or J and K, or A and D, or B and C, or J and F, or E and K are each phenyl.

In one embodiment, a specific value for formula (Ib), wherein E and F are each phenyl, anthracenyl, pyrenyl, naphthyl, 1,1'-binapthyl, or 1,1'-biphenyl.

In one embodiment, a specific value for formula (Ia), wherein L and M, or Q and V, or L and V, or Q and M are each carbon.

In one embodiment, a specific value for formula (Ia), wherein L and M, or Q and V, or L and V, or Q and M are each a heteroatom.

In one embodiment, a specific value for formula (Ia), wherein L and M, or Q and V, or L and V, or Q and M are each nitrogen.

In one embodiment, a specific value for X and Y, or W and Z, or X and Z, or W and Y are each a heteroatom.

In one embodiment, a specific value for X and Y, or W and Z, or X and Z, or W and Y are each nitrogen.

In one embodiment, a specific value for X and Y, or W and Z, or X and Z, or W and Y are each carbon.

In one embodiment, the compound of formula (Ia) or (Ib) is selected from a group consisting of:

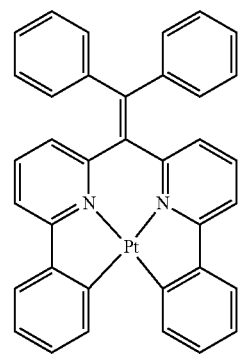

1

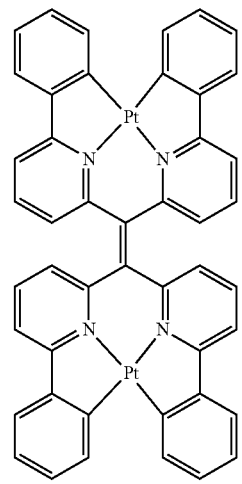

2

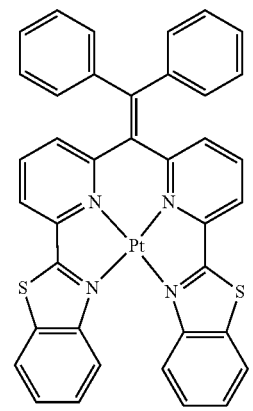

3

-continued

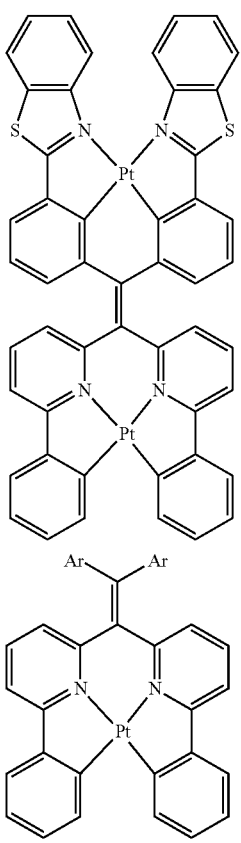

and wherein each of Ar is independently

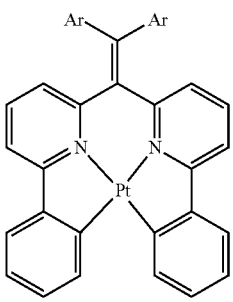

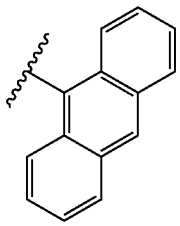

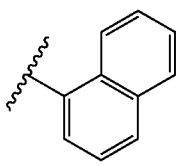

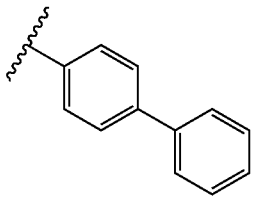

or

-continued

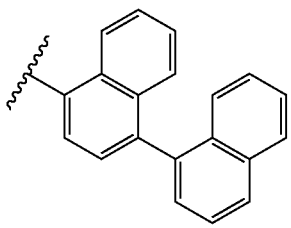

or a salt thereof.

Processes for preparing compounds of formula I are provided as further embodiments of the invention and are illustrated by the following procedures in which the meanings of the generic radicals are as given above unless otherwise qualified.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The term "mammal" as used herein refers to humans, higher non-human primates, rodents, domestic, cows, horses, pigs, sheep, dogs and cats. In one embodiment, the mammal is a human. The term "patient" as used herein refers to any animal including mammals. In one embodiment, the patient is a mammalian patient. In one embodiment, the patient is a human patient.

The term "nucleic acid" refers to deoxyribonucleotides or ribonucleotides and polymers thereof in either single- or double-stranded form, made of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues.

The terms "nucleotide sequence" and "nucleic acid sequence" refer to a sequence of bases (purines and/or pyrimidines) in a polymer of DNA or RNA, which can be single-stranded or double-stranded, optionally containing synthetic, non-natural or altered nucleotide bases capable of incorporation into DNA or RNA polymers, and/or backbone modifications (e.g., a modified oligomer, such as a morpholino oligomer, phosphorodiamate morpholino oligomer or vivo-mopholino). The terms "oligo", "oligonucleotide" and "oligomer" may be used interchangeably and refer to such sequences of purines and/or pyrimidines. The terms "modified oligos", "modified oligonucleotides" or "modified oligomers" may be similarly used interchangeably, and refer to such sequences that contain synthetic, non-natural or altered bases and/or backbone modifications (e.g., chemical modifications to the internucleotide phosphate linkages and/or to the backbone sugar). Additionally, a modified oligonucleotide may be covalently linked to a delivery molecule (e.g., a dendrimer, e.g., an octa-guanidine dendrimer). Accordingly, the term modified oligonucleotide includes morpholino oligonucleotides, such as vivo-morpholinos.

Modified nucleotides are known in the art and include, by example and not by way of limitation, alkylated purines and/or pyrimidines; acylated purines and/or pyrimidines; or other heterocycles. These classes of pyrimidines and purines are known in the art and include, pseudoisocytosine; N4, N4-ethanocytosine; 8-hydroxy-N6-methyladenine; 4-acetylcytosine, 5-(carboxyhydroxylmethyl) uracil; 5-fluorouracil; 5-bromouracil; 5-carboxymethylaminomethyl-2-thiouracil; 5-carboxymethylaminomethyl uracil; dihydrouracil; inosine; N6-isopentyl-adenine; 1-methyladenine; 1-methylpseudouracil; 1-methylguanine; 2,2-dimethylguanine; 2-methyladenine; 2-methylguanine; 3-methylcytosine; 5-methylcytosine; N6-methyladenine; 7-methylguanine; 5-methylaminomethyl uracil; 5-methoxy amino methyl-2-thiouracil; β-D-mannosylqueosine; 5-methoxycarbonylmethyluracil; 5-methoxyuracil; 2-methylthio-N6-isopentenyladenine; uracil-5-oxyacetic acid methyl ester; psueouracil; 2-thiocytosine; 5-methyl-2 thiouracil, 2-thiouracil; 4-thiouracil; 5-methyluracil; N-uracil-5-oxyacetic acid methylester; uracil 5-oxyacetic acid; queosine; 2-thiocytosine; 5-propyluracil; 5-propyl cytosine; 5-ethyluracil; 5-ethyl cytosine; 5-butyluracil; 5-pentyluracil; 5-pentylcytosine; and 2,6,-diaminopurine; methylpsuedouracil; 1-methylguanine; 1-methylcytosine. Backbone modifications are similarly known in the art, and include, chemical modifications to the phosphate linkage (e.g., phosphorodiamidate, phosphorothioate (PS), N3'phosphoramidate (NP), boranophosphate, 2',5'phosphodiester, amide-linked, phosphonoacetate (PACE), morpholino, peptide nucleic acid (PNA) and inverted linkages (5'-5' and 3'-3' linkages)) and sugar modifications (e.g., 2'-O-Me, UNA, LNA).

The oligonucleotides described herein may be synthesized using standard solid or solution phase synthesis techniques which are known in the art. In certain embodiments, the oligonucleotides are synthesized using solid-phase phosphoramidite chemistry (U.S. Pat. No. 6,773,885) with automated synthesizers. Chemical synthesis of nucleic acids allows for the production of various forms of the nucleic acids with modified linkages, chimeric compositions, and nonstandard bases or modifying groups attached in chosen places through the nucleic acid's entire length.

Certain embodiments of the invention encompass isolated or substantially purified nucleic acid compositions. In the context of the present invention, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule is substantially free of other cellular material or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived.

The following terms are used to describe the sequence relationships between two or more nucleotide sequences: (a) "reference sequence," (b) "comparison window," (c) "sequence identity" (d) "percentage of sequence identity," (e) "substantial identity" and (f) "complementarity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art. Thus, the determination of percent identity, including sequence complementarity, between any two sequences can be accomplished using a mathematical algorithm. Non-limiting examples of such mathematical algorithms are the algorithm of Myers and Miller (Myers and Miller, CABIOS, 4, 11 (1988)); the local homology algorithm of Smith et al. (Smith et al., Adv. Appl. Math., 2, 482 (1981)); the homology alignment algorithm of Needleman and Wunsch (Needleman and Wunsch, J M B, 48, 443 (1970)); the search-for-similarity-method of Pearson and Lipman (Pearson and Lipman, Proc. Natl. Acad. Sci. USA, 85, 2444 (1988)); the algorithm of Karlin and Altschul (Karlin and Altschul, Proc. Natl. Acad. Sci. USA, 87, 2264 (1990)), modified as in Karlin and Altschul (Karlin and Altschul, Proc. Natl. Acad. Sci. USA 90, 5873 (1993)).

Computer implementations of these mathematical algorithms can be utilized for comparison of sequences to determine sequence identity or complementarity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (Higgins et al., CABIOS, 5, 151 (1989)); Corpet et al. (Corpet et al., Nucl. Acids Res., 16, 10881 (1988)); Huang et al. (Huang et al., CABIOS, 8, 155 (1992)); and Pearson et al. (Pearson et al., Meth. Mol. Biol., 24, 307 (1994)). The ALIGN program is based on the algorithm of Myers and Miller, supra. The BLAST programs of Altschul et al. (Altschul et al., JMB, 215, 403 (1990)) are based on the algorithm of Karlin and Altschul supra.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, less than about 0.01, or even less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. Alignment may also be performed manually by inspection.

For purposes of the present invention, comparison of nucleotide sequences for determination of percent sequence identity may be made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection.

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, or 94%, or even at least 95%, 96%, 97%, 98%, or 99% sequence identity, compared to a reference sequence using one of the alignment programs described using standard parameters.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

(f) The term "complementary" as used herein refers to the broad concept of complementary base pairing between two nucleic acids aligned in an antisense position in relation to each other. When a nucleotide position in both of the molecules is occupied by nucleotides normally capable of base pairing with each other, then the nucleic acids are considered to be complementary to each other at this position. Thus, two nucleic acids are substantially complementary to each other when at least about 50%, preferably at least about 60% and more preferably at least about 80% of corresponding positions in each of the molecules are occupied by nucleotides which normally base pair with each other (e.g., A:T (A:U for RNA) and G:C nucleotide pairs).

Compositions and Kits

Certain embodiments provide a composition comprising 1) a plurality of compounds of formula (Ia), (Ib) or salts thereof as described herein; and 2) at least one DNA oligonucleotide.

As used herein, the term "plurality" refers to two or more (e.g., 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300 or more).

In certain embodiments, the plurality of compounds may be the same. In certain other embodiments, the plurality of compounds may be different (e.g., comprising a mixture of compounds of formula (Ia) or salts thereof, a mixture of compounds of formula (Ib) or salts thereof, or a mixture of compounds of formula (Ia) and (Ib) or salts thereof.

As described herein, the composition may comprise at least one DNA oligonucleotide (e.g., 2, 3, 4, 5, 6, 7, 8, 9, 10, 15, 20, 25, 30, 35, 40, 45, 50 or more oligonucleotides). In certain embodiments, the DNA oligonucleotide is capable of quenching near-IR (NIR) emission from the plurality of compounds described herein.

As used herein, the term "quenching" refers to reducing the intensity of the NIR emission from the compounds described herein. In certain embodiments, the NIR emission is reduced by about 20%, 25%, 30%, 35%, 40%, 45%, 50%, 55%, 60%, 65%, 70%, 75%, 80%, 85%, 90%, 95% or 100% upon contact with the DNA oligonucleotide.

In certain embodiments, the at least one DNA oligonucleotide is between about 10 to about 200 nucleotides in length (or any value in between). In certain embodiments, the oligonucleotide is about 10-150 nucleotides in length, about 10-100 nucleotides in length, about 10-90 nucleotides in length, about 10-80 nucleotides in length, about 10-70 nucleotides in length, about 10-60 nucleotides in length, about 10-50 nucleotides in length, about 10-40 nucleotides in length, about 15-40 nucleotides in length, about 20-40 nucleotides in length or about 15-30 nucleotides in length.

In certain embodiments, the at least one DNA oligonucleotide is G-quadruplex DNA. In certain embodiments, the sequence of the oligonucleotide is derived from a human c-myc oncogene. In certain embodiments, the at least one DNA oligonucleotide comprises a sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% sequence identity to GGGGTTTTGGGGGGGTTTTGGG (SEQ ID NO:1), AGGGTTAGGGTTAGGGTTAGGG (SEQ ID NO:2), or TGAGGGTGGGTAGGGTGGGTAA (SEQ ID NO:3). In certain embodiments, the at least one DNA oligonucleotide comprises a sequence GGGGTTTTGGGGGGGTTTTGGG (SEQ ID NO:1), AGGGTTAGGGTTAGGGTTAGGG (SEQ ID NO:2), or TGAGGGTGGGTAGGGTGGGTAA (SEQ ID NO:3). In certain embodiments, the at least one DNA oligonucleotide consists of GGGGTTTTGGGGGGGTTTTGGG (SEQ ID NO:1), AGGGTTAGGGTTAGGGTTAGGG (SEQ ID NO:2), or TGAGGGTGGGTAGGGTGGGTAA (SEQ ID NO:3).

In certain embodiments, the at least one DNA oligonucleotide comprises TGAGGGTGGGTAGGGTGGGTAA (SEQ ID NO:3). In certain embodiments, the at least one DNA oligonucleotide consists of TGAGGGTGGGTAGGGTGGGTAA (SEQ ID NO:3).

In certain embodiments, the composition further comprises a buffer (e.g., Tris buffer)

In certain embodiments, the composition further comprises a solvent, such as DMSO.

In certain embodiments, the composition further comprises magnesium.

The present invention further provides kits for practicing the present methods.

Accordingly, certain embodiments provide a kit comprising:

1) a plurality of compounds of formula (Ia), (Ib) or salts thereof as described herein;

2) G-quadruplex DNA; and 3) instructions for detecting the presence of DNAse I in a test sample or identifying a DNAse I inhibitor, using the plurality of compounds and the G-quadruplex DNA.

In certain embodiments, the kit further comprises DNAse I. Such kits may also optionally contain one or more of: a positive and/or negative control, RNase-free water, and one or more buffers. In certain embodiments, a kit may further include RNase-free laboratory plasticware (e.g., a plate(s), such a multi-well plate(s), such as a 96 well plate(s) (e.g., DNA binding), a petri dish(es), a test tube(s), a cuvette(s), a plate(s) for fluorescence or luminescence etc.). For example, in certain embodiments, the kit further comprises a solid support.

Methods of Use

Certain embodiments provide a method of detecting the presence of DNAse I in a test sample, the method comprising:

1) combining a plurality of compounds of formula (Ia), (Ib) or salts thereof as described herein and at least one DNA oligonucleotide to form a composition;

2) contacting the composition with the test sample to provide a first reaction mixture; and 3) measuring the NIR emission intensity of the first reaction mixture, wherein an increase in the NIR emission intensity as compared to a control correlates with the presence of DNAse I in the test sample. In certain embodiments, the control is a negative control, wherein the control sample does not contain DNAse I.

Certain embodiments also provide a method of detecting the presence of DNAse I in a test sample, the method comprising:

1) contacting a composition as described herein with the test sample to provide a first reaction mixture; and 2) measuring the NIR emission intensity of the first reaction mixture, wherein an increase in the NIR emission intensity as compared to a control correlates with the presence of DNAse I in the test sample.

In certain embodiments, the method further comprises measuring the NIR emission intensity of the composition prior to contact with the test sample.

Certain embodiments provide a method of detecting the presence of DNAse I in a test sample, the method comprising:

1) measuring the NIR emission intensity of a composition described herein;

2) contacting the composition with the test sample to provide a first reaction mixture; and 3) measuring the NIR emission intensity of the first reaction mixture, wherein an increase in the NIR emission of the first reaction mixture as compared to the NIR emission intensity of the composition correlates with the presence of DNAse I in the test sample.

In certain embodiments, the test sample is a liquid laboratory sample. In certain embodiments, the test sample is a biological sample (e.g., fluid) obtained from a test subject, such as a mammal. As described herein, the term "biological fluid" refers to any bio-organic fluid produced by an organism and includes, but is not limited to, e.g., amniotic fluid, aqueous humour, vitreous humour, bile, blood or components of blood (e.g., serum or plasma), milk, cerebrospinal fluid (CSF), endolymph, perilymph, feces, lymph, mucus, pericardial fluid, peritoneal fluid, pleural fluid, pus, serous fluid, semen, sputum, synovial fluid, sweat, urine, saliva, tears, vaginal secretions and vomit. In certain embodiments, the biological fluid is blood or a blood component, such as serum. In certain embodiments, the biological fluid is urine. In certain embodiments, a method described herein may be used to directly analyze a biological fluid for the presence of a DNAse I, without processing the fluid. Accordingly, in certain embodiments, the test sample is an unprocessed biological fluid obtained from a mammal, such as a human. In certain embodiments, the test sample comprises DNAse I. In certain embodiments, the test sample does not comprise DNAse I.

In certain embodiments, the methods further comprise obtaining a test sample (e.g., a biological sample) from a test subject (e.g., a mammal, e.g., a human).

Certain embodiments provide a method of identifying a DNAse I inhibitor, the method comprising:
1) combining a plurality of compounds of formula (Ia), (Ib) or salts thereof as described herein and DNA to form a composition;
2) contacting the composition, DNAse I and a test compound to provide a first reaction mixture;
3) measuring the NIR emission intensity of the first reaction mixture; and
4) identifying the test compound as a DNAse I inhibitor when a decrease in the NIR emission intensity is detected as compared to a control.

Certain embodiments provide a method of identifying a DNAse I inhibitor, the method comprising:
1) contacting a composition as described herein, DNAse I and a test compound to provide a first reaction mixture;
2) measuring the NIR emission intensity of the first reaction mixture; and
3) identifying the test compound as a DNAse I inhibitor when a decrease in the NIR emission intensity is detected as compared to a control.

Certain embodiments provide a method of identifying a DNAse I inhibitor, the method comprising:
1) contacting a composition as described herein and DNAse I to provide a first reaction mixture;
2) measuring the NIR emission intensity of the first reaction mixture;
3) contacting a composition as described herein, DNAse I and the test compound to provide a second reaction mixture;
4) measuring the NIR emission intensity of the second reaction mixture; and
5) identifying the test compound as a DNAse I inhibitor when the NIR emission intensity of the second reaction mixture is less than the NIR emission intensity of the first reaction mixture.

In certain embodiments, the emission is measured at 785 nm.

In certain embodiments, the methods further comprise incubating the plurality of compounds and the at least one DNA oligonucleotide under conditions and for a time sufficient for binding between the compounds and the DNA oligonucleotide to occur. In certain embodiments, these components incubated under a set of conditions described herein.

In certain embodiments, the methods further comprise incubating a composition comprising the plurality of compounds and the at least one DNA oligonucleotide with the test sample under conditions and for a time sufficient for DNAse I to disrupt binding between the compounds and the DNA oligonucleotide and for the compounds to form a complex. In certain embodiments, these components incubated under a set of conditions described herein.

Certain embodiments provide an assay as described herein for detecting the presence of DNAse I in a test sample (see, e.g., the Examples or Figures).

Certain embodiments provide an assay as described herein for detecting a DNAse I inhibitor (see, e.g., the Examples or Figures).

The invention will now be illustrated by the following non-limiting Examples.

EXAMPLES

Example 1

Synthesis of Platinum(II) Complex 2

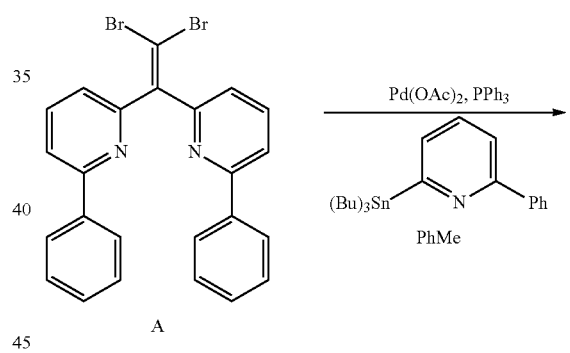

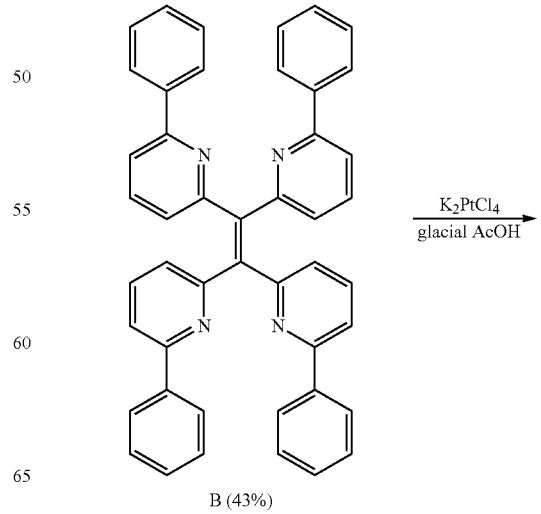

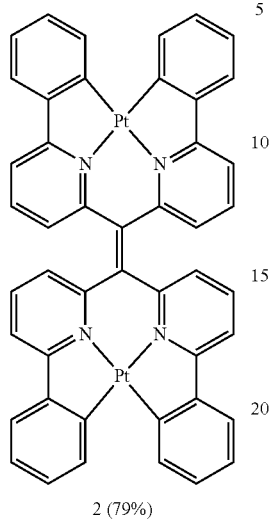

2 (79%)

1,1,2,2-Tetrakis(6-phenylpyridin-2-yl)ethene (B). Compound A (Gabr M. T. et a. *Inorg. Chem.* 2018, 57, 12641-12649.) (377 mg, 0.76 mmol) was dissolved in PhMe (25 mL). The flask was charged with Pd(OAc)$_2$ (108 mg, 0.48 mmol), PPh$_3$ (524 mg, 2.00 mmol) and 2-phenyl-6-(tributylstannyl)pyridine (Gros, P. et al. *J. Org. Chem.* 2003, 63, 2028-2029.) (1.37 g, 3.10 mmol). The reaction was heated to reflux under argon overnight. The organic solvent was evaporated under reduced pressure and the crude product was dissolved in MeCN (50 mL) and filtered over Celite. The MeCN layer was extracted with hexane (2×25 mL), then the hexane layer was discarded. The MeCN layer was concentrated under reduced pressure and the crude product was purified by flash column chromatography using 40% ethyl acetate in hexane as eluent to yield B (212 mg, 43%) as a yellowish white solid. Mp 129-132° C. $^1$H NMR (400 MHz, CDCl$_3$) δ 7.56-7.66 (m, 16H), 7.90 (d, 4H, J=7.8 Hz), 8.02 (t, 4H, J=7.8, 7.8 Hz), 8.28-8.33 (m, 8H). $^{13}$C NMR (75 MHz, CDCl$_3$) δ 119.4, 120.2, 126.9, 128.6, 128.9, 136.7, 137.5, 139.3, 155.8, 156.2. HRMS (ESI): calcd for C$_{46}$H$_{33}$N$_4$ [M+H]$^+$, 641.2705; found, 641.2709.

Complex 2. Compound B (22.0 mg, 0.034 mmol) and K$_2$PtCl$_4$ (29.0 mg, 0.068 mmol) were mixed in glacial acetic acid (3 mL), and the resulting mixture was heated under reflux overnight. After cooling to rt, the crude reaction mixture was poured into H$_2$O (30 mL) and the resulting yellow precipitate was collected by vacuum filtration. The crude material was purified by flash column chromatography using 100% dichloromethane to yield 2 (27.5 mg, 79%) as a yellow solid. Mp>220° C. $^1$H NMR (400 MHz, DMSO-d$_6$) δ 7.01-7.05 (m, 4H), 7.29-7.41 (m, 12 H), 7.85 (d, 4H, J=7.6 Hz), 7.91-7.95 (m, 4H), 8.52 (d, 4H, J=7.9 Hz). $^{13}$C NMR (100 MHz, methanol-d$_4$) δ 120.1, 122.3, 123.4, 127.2, 127.6, 127.8, 129.5, 129.8, 138.6, 140.5, 149.8, 158.6. MS (EI): calcd for C$_{46}$H$_{28}$N$_4$Pt$_2$ [M]$^+$, 1026.1; found, 1026.1.

Example 2

Synthesis of 3,3'-(2,2-Diphenylethene-1,1-diyl)dibenzaldehyde (D)

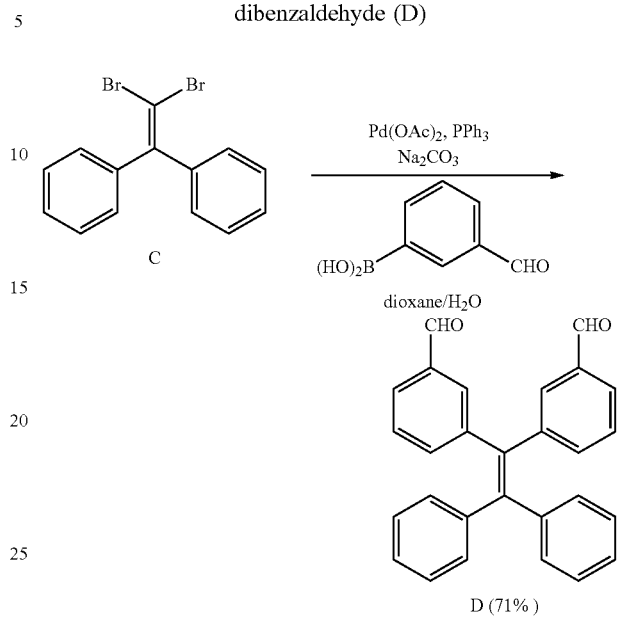

D (71%)

3,3'-(2,2-Diphenylethene-1,1-diyl)dibenzaldehyde (D). Compound C (Barnes, J. C. et al. *J. Am. Chem. Soc.* 2013, 135, 183-192.) (338 mg, 1.00 mmol) was dissolved in 50 mL of dioxane:water (4:1). The flask was charged with Na$_2$CO$_3$ (690 mg, 5.00 mmol), Pd(OAc)$_2$ (54 mg, 0.24 mmol), PPh$_3$ (262 mg, 1.00 mmol) and 3-formylphenylboronic acid (750 mg, 5.00 mmol). The reaction was heated to reflux under argon overnight. After cooling, the reaction mixture was diluted with water and extracted with ethyl acetate (2×50 mL) and the combined organic fractions were dried over anhydrous Na$_2$SO$_4$, filtered, and concentrated under reduced pressure. The crude product was purified by flash column chromatography using 5% ethyl acetate in hexane as eluent to yield D (275 mg, 71%) as a white solid. Mp 115-116° C. $^1$H NMR (400 MHz, CDCl$_3$) δ 7.03-7.06 (m, 4H), 7.10-7.13 (m, 6H), 7.26-7.34 (m, 4H), 7.54-7.56 (m, 2H), 7.64-7.66 (m, 2H), 9.80 (s, 2H). $^{13}$C NMR (100 MHz, CDCl$_3$) δ 128.3, 129.0, 129.1, 129.8, 132.2, 133.7, 137.3, 138.3, 139.0, 143.5, 144.9, 145.1, 193.1. HRMS (ESI): calcd for C$_{28}$H$_{21}$O$_2$ [M+H]$^+$, 389.1542; found, 389.1539.

Example 3

Synthesis of 2,2'-((2,2-Diphenylethene-1,1-diyl)bis(3,1-phenylene))bis(benzothiazole) (E)

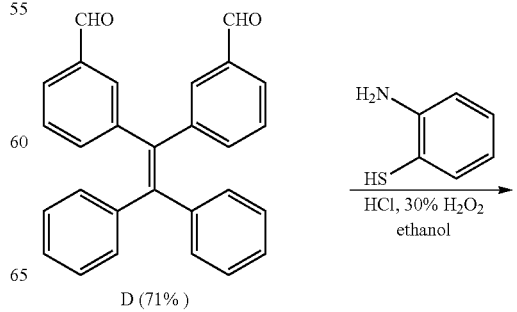

D (71%)

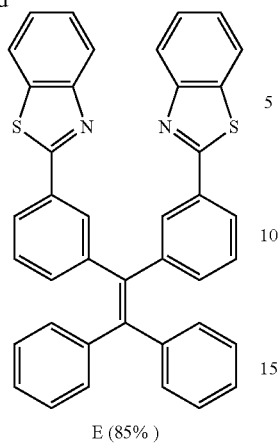

E (85%)

2,2'-((2,2-Diphenylethene-1,1-diyl)bis(3,1-phenylene)) bis(benzothiazole) (E). Compound D (415 mg, 1.07 mmol) and 2-aminothiophenol (266 mg, 2.13 mmol) were dissolved in ethanol (12 mL). After addition of 37.2% aq. HCl (0.52 mL, 6.20 mmol) and 30% aq. $H_2O_2$ (1.33 mL, 13.00 mmol), the reaction mixture was stirred at room temperature for 2 h. The reaction mixture was diluted with water (100 mL) and extracted with ethyl acetate (2×50 mL) and the combined organic fractions were dried over anhydrous $Na_2SO_4$, filtered, and concentrated under reduced pressure. The crude product was purified by flash column chromatography using 3% ethyl acetate in hexane as eluent to yield E (544 mg, 85%) as a yellowish white solid. Mp 160-162° C. $^1$H NMR (400 MHz, $CDCl_3$) δ 7.23-7.27 (m, 10H), 7.33-7.38 (m, 4H), 7.44-7.46 (m, 2H), 7.53-7.55 (m, 2H), 7.93-7.95 (m, 4H), 8.01 (dt, J=7.5, 1.4 Hz, 2H), 8.13 (d, J=8.1 Hz, 2H). $^{13}$C NMR (100 MHz, $CDCl_3$) δ 122.6, 124.2, 126.1, 126.9, 127.3, 128.1, 129.0, 129.7, 131.7, 132.3, 134.3, 135.1, 136.1, 139.9, 144.0, 144.2, 145.0, 155.1, 169.0. HRMS (ESI): calcd for $C_{40}H_{27}N_2S_2$ [M+H]$^°$, 599.1616; found, 599.1614.

Example 4

Synthesis of Platinum(II) Complex 3

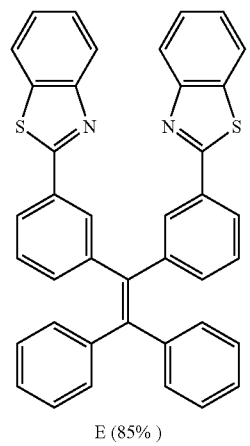

E (85%)

$\xrightarrow{K_2PtCl_4}{\text{glacial AcOH}}$

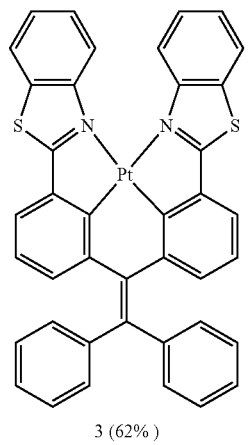

3 (62%)

Complex 3. Using the procedure given for the preparation of 2, compound E (150 mg, 0.25 mmol) and $K_2PtCl_4$ (104 mg, 0.25 mmol) gave 3 (123 mg, 62%) as a yellow solid after purification by flash column chromatography using 100% dichloromethane as eluent. Mp>230° C. $^1$H NMR (400 MHz, DMSO-$d_6$) δ 7.09-7.14 (m, 6H), 7.17-7.22 (m, 4H), 7.25-7.28 (m, 2H), 7.38-7.45 (m, 4H), 7.49-7.53 (m, 2H), 7.78-7.80 (m, 2H), 7.98-8.01 (m, 2H), 8.08-8.11 (m, 2H). $^{13}$C NMR (75 MHz, DMSO-$d_6$) δ 125.3, 126.0, 127.7, 128.1, 128.7, 129.2, 129.7, 131.5, 132.0, 132.2, 132.4, 135.8, 136.2, 137.4, 140.4, 141.7, 146.6, 156.5, 169.9. HRMS (EI): calcd for $C_{40}H_{24}N_2PtS_2$ [M]$^+$, 791.1029; found, 791.1035.

Example 5

Synthesis of 3,3'-(2,2-Bis(6-phenylpyridin-2-yl) ethene-1,1-diyl)dibenzaldehyde (F)

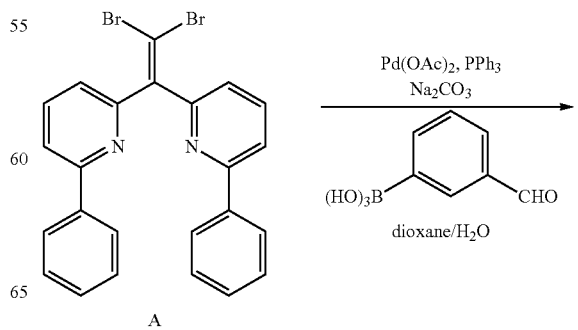

A

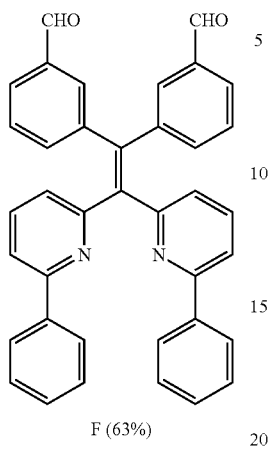

F (63%)

3,3'-(2,2-Bis(6-phenylpyridin-2-yl)ethene-1,1-diyl) dibenzaldehyde (F). Using the procedure given for the preparation of D, coupling of A (Gabr M. T. et a. *Inorg. Chem.* 2018, 57, 12641-12649.) (1.51 g, 3.07 mmol) and 3-formylphenylboronic acid (2.30 g, 15.34 mmol) gave F (1.05 g, 63%) as a light yellow solid after purification by flash column chromatography using 10% ethyl acetate in hexane followed by 20% ethyl acetate in hexane as eluent. Mp 137-139° C. $^1$H NMR (300 MHz, CDCl$_3$) δ 7.25-7.27 (m, 2H), 7.46-7.49 (m, 6H), 7.51-7.55 (m, 2H), 7.63-7.69 (m, 8H), 7.74-7.78 (m, 2H), 7.88-7.92 (m, 4H), 10.03 (s, 2H). $^{13}$C NMR (75 MHz, CDCl$_3$) δ 118.6, 124.5, 126.6, 126.8, 127.9, 128.2, 128.6, 128.7, 132.2, 136.2, 136.5, 138.8, 142.3, 142.6, 143.8, 156.4, 159.1, 191.7. HRMS (ESI): calcd for C$_{38}$H$_{27}$N$_2$O$_2$ [M+H]$^+$, 543.2073; found, 543.2072.

Example 6

Synthesis of 2,2'-((2,2-Bis(6-phenylpyridin-2-yl) ethene-1,1-diyl)bis(3,1-phenylene))bis(benzothiazole) (G)

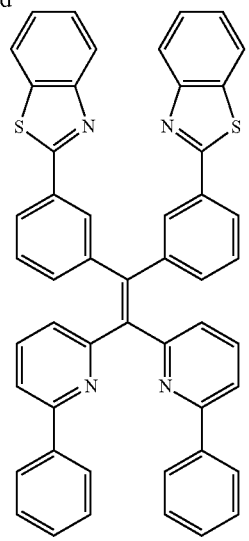

G (74%)

2,2'-((2,2-Bis(6-phenylpyridin-2-yl)ethene-1,1-diyl)bis (3,1-phenylene))bis(benzothiazole) (G). Using the procedure given for the preparation of E, compound F (364 mg, 0.67 mmol) and 2-aminothiophenol (169 mg, 1.35 mmol) gave G (373 mg, 74%) as a yellow solid after purification by flash column chromatography using 10% ethyl acetate in hexane as eluent. Mp 171-172° C. $^1$H NMR (300 MHz, CDCl$_3$) δ 7.28 (d, J=7.5 Hz, 2H), 7.38-7.43 (m, 8H), 7.46-7.52 (m, 6H), 7.55-7.57 (m, 2H), 7.64-7.67 (m, 2H), 7.69-7.74 (m, 4H), 7.86 (d, J=7.5 Hz, 2H), 8.10-8.14 (m, 6H). $^{13}$C NMR (75 MHz, CDCl$_3$) δ 118.1, 120.9, 122.5, 124.1, 124.5, 125.5, 125.6, 126.4, 127.8, 128.1, 128.2, 129.8, 132.8, 132.9, 134.4, 136.0, 138.8, 141.6, 143.0, 143.2, 153.4, 156.1, 159.2, 167.1. HRMS (ESI): calcd for C$_{50}$H$_{33}$N$_4$S$_2$ [M+H]$^°$, 753.2146; found, 753.2148.

Example 7

Synthesis of Platinum(II) Complex 4

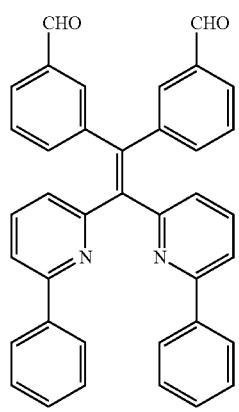

F (63%)

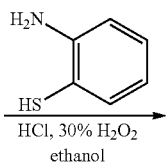

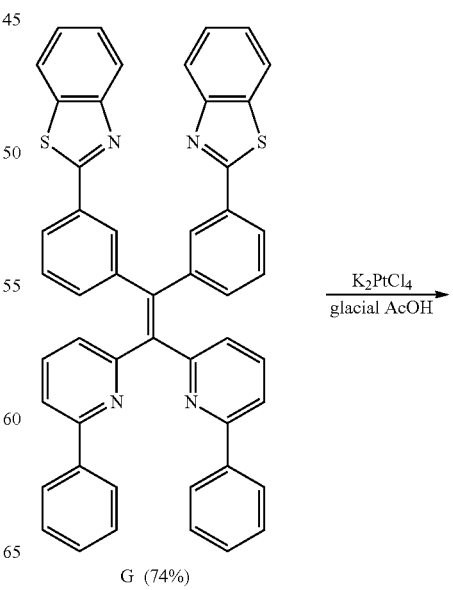

G (74%)

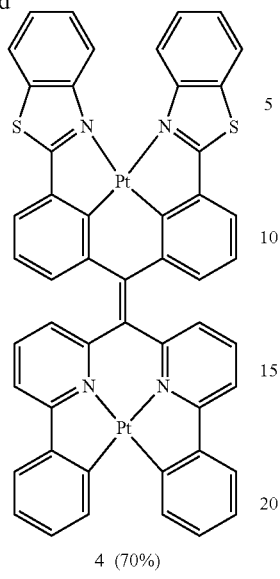

4 (70%)

Complex 4. Using the procedure given for the preparation of 2, compound G (60.2 mg, 0.08 mmol) and $K_2PtCl_4$ (99.6 mg, 0.24 mmol) gave 4 (63.7 mg, 70%) as a yellow solid after purification by flash column chromatography using 25% ethyl acetate in hexane as eluent. Mp>230° C. $^1$H NMR (300 MHz, CDCl$_3$) δ 7.29-7.34 (m, 6H), 7.41 (d, J=7.4 Hz, 2H), 7.48-7.51 (m, 4H), 7.55-7.61 (m, 4H), 7.73 (d, J=7.9 Hz, 2H), 7.82-7.84 (m, 2H), 7.91-7.93 (m, 2H), 8.00 (d, J=7.6 Hz, 2H), 8.08 (d, J=7.6 Hz, 2H), 8.31-8.33 (m, 2H). $^{13}$C NMR (100 MHz, CDCl$_3$) δ 122.4, 124.0, 124.8, 126.0, 126.2, 127.2, 128.0, 128.8, 128.9, 129.0, 129.2, 129.7, 130.0, 130.3, 131.6, 132.5, 132.7, 134.2, 135.7, 139.2, 140.4, 142.6, 148.4, 154.6, 160.2, 167.7. $^{195}$Pt NMR (86 MHz, CDCl$_3$) δ −2474.3,−2437.3. MS (EI): calcd for $C_{50}H_{28}N_4Pt_2S_2$ [M]$^+$, 1138.1; found, 1138.1. Anal. Calcd $C_{50}H_{28}N_4Pt_2S_2$ (1138.11): C, 52.72; H, 2.48; N, 4.92. Found: C, 52.48; H, 2.41; N, 4.99.

Compounds H-M below were prepared in a manner similar to compound B, as shown in Example 1.

Example 8

Synthesis of Platinum(II) Complex 1

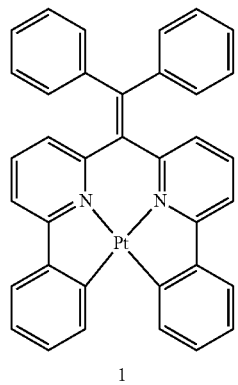

1

Complex 1. Using the procedure given for the preparation of 2, compound H (302 mg, 0.62 mmol) and $K_2PtCl_4$ (257 mg, 0.62 mmol) gave 1 (345 mg, 82%) as a yellow solid after purification by flash column chromatography using 50% petroleum ether in dichloromethane followed by 25% petroleum ether in dichloromethane. Mp>230° C. $^1$H NMR (400 MHz, CDCl$_3$) δ 6.98 (d, 2H, J=7.9 Hz), 7.13-7.24 (m, 12H), 7.36-7.41 (m, 4H), 7.51-7.53 (m, 2H), 7.59 (d, 2H, J=8.1 Hz), 8.34 (d, 2H, J=8.0 Hz). $^{13}$C NMR (100 MHz, CDCl$_3$) δ 117.8, 124.6, 125.2, 125.5, 128.4, 129.3, 129.5, 129.6, 130.6, 136.8, 137.6, 141.3, 148.5, 148.9, 153.3, 155.3, 166.5. HRMS (EI): calcd for $C_{36}H_{24}N_2Pt$ [M]$^+$, 679.1587; found, 679.1585.

Example 9

Synthesis of Platinum(II) Complex 17

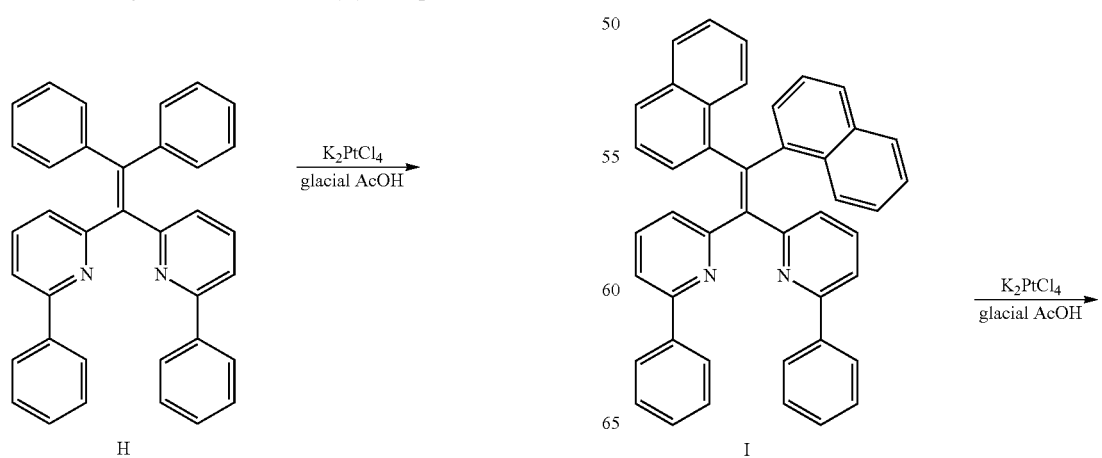

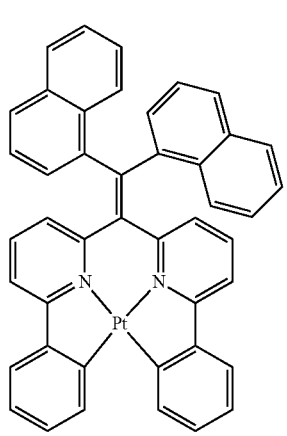

17

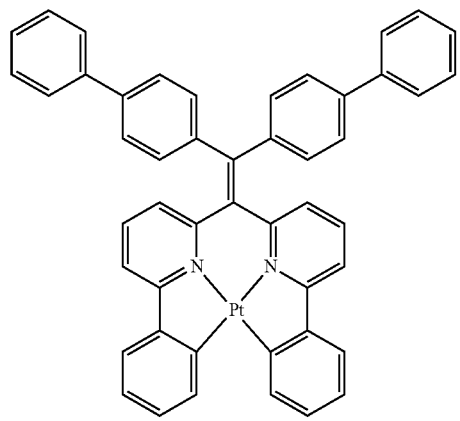

18

Complex 17. Using the procedure given for the preparation of 2, compound I (158 mg, 0.27 mmol) and K$_2$PtCl$_4$ (112 mg, 0.27 mmol) gave 17 (139 mg, 66%) as yellow solid after purification by flash column chromatography using 20% hexane in dichloromethane as eluent. Mp>230° C. 1H NMR (400 MHz, CDCl$_3$) δ 6.89 (d, 4H, J=8.0 Hz), 7.36-7.41 (m, 6H), 7.53-7.56 (m, 4H), 7.58-7.62 (m, 6H), 7.91-7.93 (m, 4H), 8.26-8.29 (m, 4H). $^{13}$C NMR (100 MHz, CDCl$_3$) δ 117.0, 119.9, 123.3, 125.7, 125.8, 126.5, 127.8, 127.9, 128.4, 129.2, 129.5, 129.8, 130.0, 133.5, 135.0, 137.5, 137.8, 140.1, 143.6, 145.1, 155.0, 157.7, 160.4. HRMS (EI): calcd for C$_{44}$H$_{28}$N$_2$Pt [M]$^+$, 779.1900; found, 779.1905.

Complex 18. Using the procedure given for the preparation of 2, compound J (57.5 mg, 0.09 mmol) and K$_2$PtCl$_4$ (37.3 mg, 0.09 mmol) gave 18 (64.4 mg, 86%) as yellow solid after purification by flash column chromatography using 100% dichloromethane as eluent. Mp>230° C. $^1$H NMR (400 MHz, CDCl$_3$) δ 7.17 (d, 2H, J=7.9 Hz), 7.28-7.33 (m, 6H), 7.45-7.50 (m, 8H), 7.56-7.60 (m, 4H), 7.65-7.69 (m, 2H), 7.83-7.87 (m, 4H), 8.01-8.04 (m, 4H), 8.27-8.32 (m, 2H). $^{13}$C NMR (100 MHz, CDCl$_3$) δ 119.0, 120.1, 121.3, 123.0, 124.4, 126.3, 127.2, 127.8, 128.0, 128.5, 129.0, 129.8, 130.3, 131.0, 137.4, 139.0, 141.7, 143.9, 154.2, 158.5, 161.1. HRMS (EI): calcd for C$_{48}$H$_{32}$N$_2$Pt [M]$^+$, 831.2213; found, 831.2216.

Example 10

Synthesis of Platinum(II) Complex 18

Example 11

Synthesis of Platinum(II) Complex 19

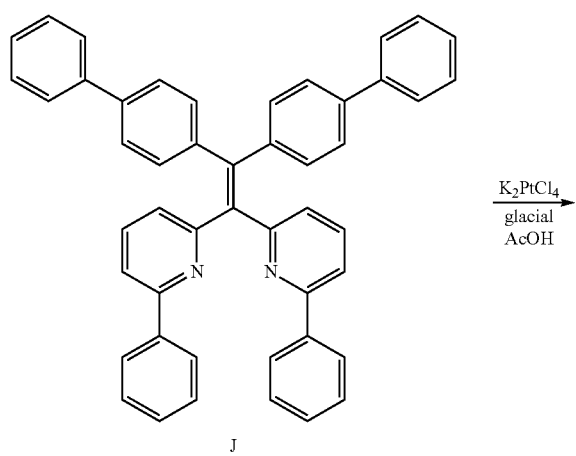

J

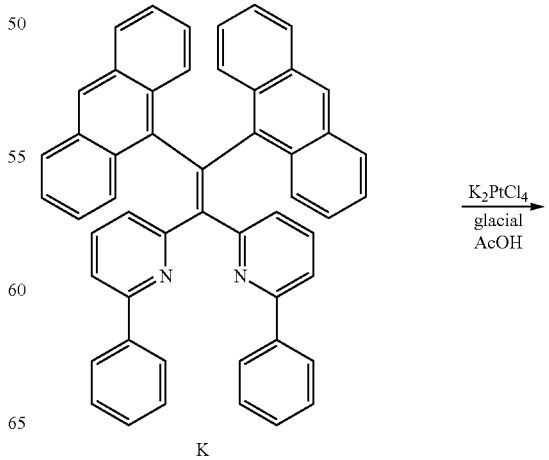

K

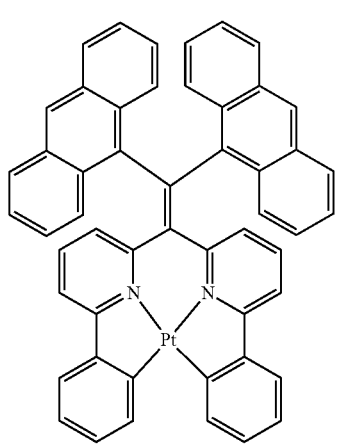

19

Complex 19. Using the procedure given for the preparation of 2, compound K (103 mg, 0.15 mmol) and K$_2$PtCl$_4$ (62.2 mg, 0.15 mmol) gave 19 (77.8 mg, 59%) as yellow solid after purification by flash column chromatography using 100% dichloromethane as eluent. Mp>230° C. $^1$H NMR (400 MHz, CDCl$_3$) δ 7.09-7.12 (m, 4H), 7.19-7.26 (m, 10H), 7.43-7.46 (m, 6H), 7.62-7.67 (m, 6H), 7.77-7.81 (m, 4H), 7.79 (s, 2H). $^{13}$C NMR (100 MHz, CDCl$_3$) δ 119.8, 124.5, 125.2, 127.3, 127.7, 128.0, 128.3, 128.6, 129.0, 129.8, 129.9, 130.2, 131.3, 131.5, 131.8, 135.2, 137.5, 140.2, 142.1, 157.8, 160.1. HRMS (EI): calcd for C$_{52}$H$_{32}$N$_2$Pt [M]$^+$, 879.2213; found, 879.2214.

Example 12

Synthesis of Platinum(II) Complex 20

20

Complex 20. Using the procedure given for the preparation of 2, compound L (347 mg, 0.47 mmol) and K$_2$PtCl$_4$ (196 mg, 0.47 mmol) gave 20 (355 mg, 81%) as yellow solid after purification by flash column chromatography using 100% dichloromethane as eluent. Mp>230° C. $^1$H NMR (400 MHz, CDCl$_3$) δ 7.23-7.31 (m, 4H), 7.47-7.57 (m, 4H), 7.70-7.83 (m, 6H), 7.87-7.95 (m, 4H), 8.03-8.17 (m, 8H), 8.46 (d, 4H, J=8.8 Hz), 8.64 (d, 2H, J=9.0 Hz). $^{13}$C NMR (100 MHz, CDCl$_3$) δ 118.7, 121.5, 122.5, 123.9, 124.2, 125.1, 125.4, 126.2, 127.2, 127.3, 127.5, 127.7, 127.8, 128.5, 129.7, 129.9, 130.2, 130.4, 131.3, 131.4, 134.2, 134.4, 136.0, 136.1, 143.4, 145.5, 149.2, 154.9, 161.6. MS (EI): calcd for C$_{56}$H$_{32}$N$_2$Pt [M]$^+$, 927.2; found, 927.2.

Example 13

Synthesis of Platinum(II) Complex 21

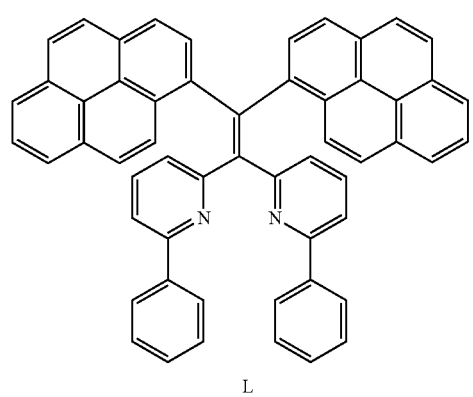

L

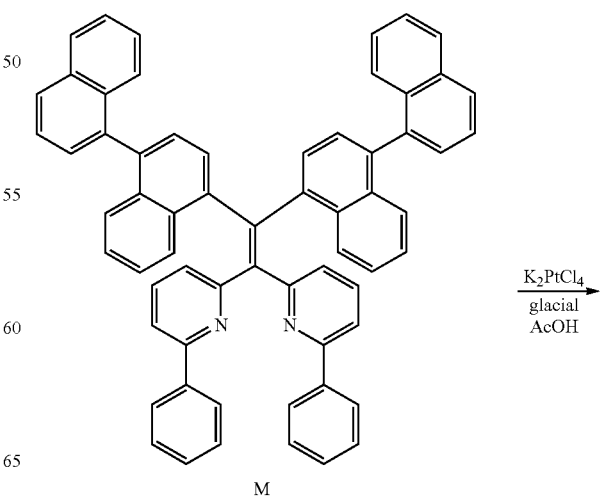

M

-continued

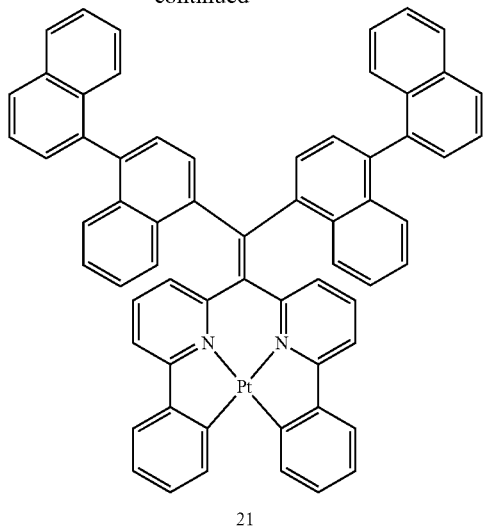

21

Complex 21. Using the procedure given for the preparation of 2, compound M (83.9 mg, 0.10 mmol) and $K_2PtCl_4$ (41.5 mg, 0.10 mmol) gave 21 (91.8 mg, 89%) as yellow solid after purification by flash column chromatography using 100% dichloromethane as eluent. Mp>230° C. $^1H$ NMR (400 MHz, $CDCl_3$) δ 7.10 (d, 2H, J=8.1 Hz), 7.32-7.36 (m, 6H), 7.47-7.52 (m, 6H), 7.56-7.63 (m, 8H), 7.78 (d, 2H, J=7.6 Hz), 7.83-7.86 (m, 4H), 8.01-8.04 (m, 6H), 8.27 (d, 2H, J=8.2 Hz), 8.32-8.35 (m, 4H). $^{13}C$ NMR (100 MHz, $CDCl_3$) δ 120.6, 122.8, 125.5, 126.4, 126.6, 127.0, 127.1, 127.2, 127.6, 128.1, 128.6, 128.9, 129.2, 129.3, 129.4, 132.2, 132.5, 132.6, 133.3, 133.4, 133.6, 133.8, 134.6, 135.5, 138.7, 139.9, 140.7, 141.9, 143.1, 144.7, 152.4, 156.0, 163.8. MS (EI): calcd for $C_{64}H_{40}N_2Pt$ $[M]^+$, 1031.2; found, 1031.2.

The compounds described in Examples 1-13 were synthesized and analyzed as described in Example 14 below.

Example 14

Luminescent platinum(II) complexes display intriguing photophysical properties and are attracting increasing interest in materials chemistry and optoelectronics (Yam, V. W.-W. et al. *Chem. Rev.* 2015, 115, 7589-7728; Mauro, M. et al. *Chem. Commun.* 2014, 50, 7269-7272; Kuang, S. et al. *Chem. Commun.* 2018, 54, 2169-2172; Chan, A. K.-W. et al. *J. Am. Chem. Soc.* 2017, 139, 10750-10761 and Huo, S. et al. *Asian Org. Chem.* 2015, 4, 1210-1245). In addition, the $d^8$ electronic configuration and typical square planar coordination geometry observed in these complexes imparts a tendency to display metal-metal and/or π-π stacking interactions upon self-assembly (Yam, V. W.-W. et al. *Chem. Rev.* 2015, 115, 7589-7728 and Mauro, M. et al. *Chem. Commun.* 2014, 50, 7269-7272). These self-assembly events are often signaled by drastic color changes in the visible region and emergence of near-infrared (NIR) luminescence. This general emission profile has resulted in the use of several Pt(II) complexes as components in luminescent sensors for applications in materials chemistry and, less commonly, as biological probes (Chan, A. K.-W. et al. *Acc. Chem. Res.* 2018, 51, 3041-3051; Law, A. S.-Y et al. *ACS Appl. Mater. Interfaces* 2017, 9, 41143-41150; Li, K. et al. *Chem. Sci.* 2016, 7, 1653-1673; Aliprandi, A. et al. *Chem. Lett.* 2015, 44, 1152-1169; Chung, C. Y-S. et al. *J. Am. Chem. Soc.* 2011, 133, 18775-18784; Yeung, M. C.-L et al. *Chem. Commun.* 2010, 46, 7709-7711 and Law, A. S.-Y. et al. Mater. *Interfaces* 2019, 11, 4799-4808).

Figure 15:
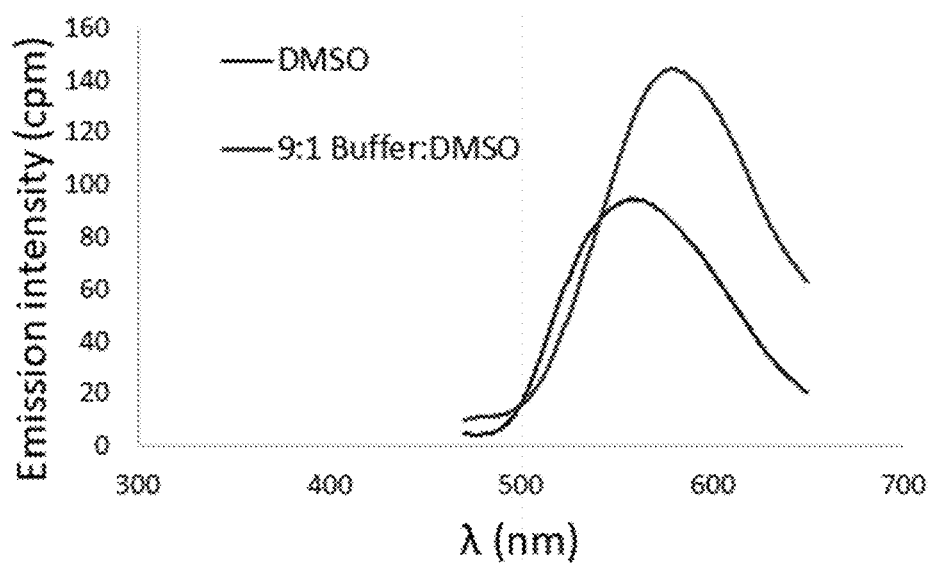
FIG. 15. Emission profile of 3 in DMSO and 9:1 Tris buffer (10 mM Tris-HCl, pH 7.5):DMSO. $\lambda_{ex}$=414 nm, [3]=4 µM.

As described herein, it has been observed that cyclometalated Pt(II) complex 1 (FIG. 1) displays significantly red-shifted emission in 9:1 Tris buffer:$CH_3CN$ solution compared to pure $CH_3CN$ ($\lambda_{em}$=594 and 505 nm, respectively) (Gabr et al., *Inorg. Chem.* 2018, 57, 12641-12649). Similarly, bis(benzothiazole)Pt(II) complex 3 also was found to exhibit a slightly red-shifted emission in aqueous solution compared to emission in DMSO (FIG. 15). Luminescent properties may be affected by Pt . . . Pt interactions. The bimetallic Pt(II) complexes 2 and 4 were prepared to test the hypothesis that introduction of additional Pt centers into the tetraarylethylene scaffold will further enhance the likelihood of metal-metal interactions upon aggregation-induced self-assembly, in turn resulting in even further bathochromic shifts in emission into the NIR region. Toward this end, bis(platinum) complex 4 were found to exhibit the targeted emission profile, and the switchability of NIR emission in 4 were successfully exploited in the presence of DNA oligomers to develop an experimentally simple, sensitive, and label-free turn-on assay for DNAse I activity.

Results and Discussion

Figure 14:
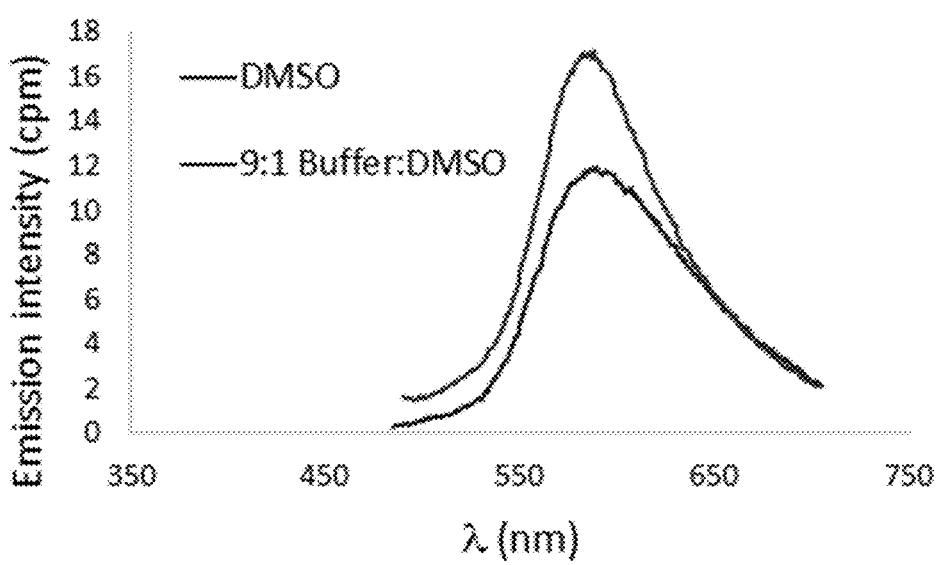
FIG. 14. Emission profile of 2 in DMSO and 9:1 Tris buffer (10 mM Tris-HCl, pH 7.5):DMSO. $\lambda_{ex}$=416 nm, [2]=4 µM.

The synthesis of 2-4 was accomplished in high yield using a route similar to that previously reported for the synthesis of 1 (see Examples). Complex 2, however, displayed absorbance ($\lambda_{abs}$=416 nm) and emission ($\lambda_{ems}$=591 nm) spectra very similar to those obtained for mono-platinum complex 1, and the wavelength of emission was unaffected by solvent-induced aggregation (FIG. 14). In contrast, complex 4 exhibited significant aggregation-induced bathochromic shifts in both absorbance and luminescence spectra.

Figure 2A:
FIGS. 2A-2C. (2A) Solution of 4 in DMSO/Tris buffer mixtures, [4]=50 Tris buffer percentage from left to right: 0, 10, 20, 40, 60, 70, 80, 90%. (2B) UV-vis absorption changes of 4 in DMSO/buffer mixtures, [4]=4 µM. (2C) Emission spectra of 4 in DMSO/buffer mixtures, $\lambda_{ex}$=445 nm, [4]=4 µM.
Figure 2B:
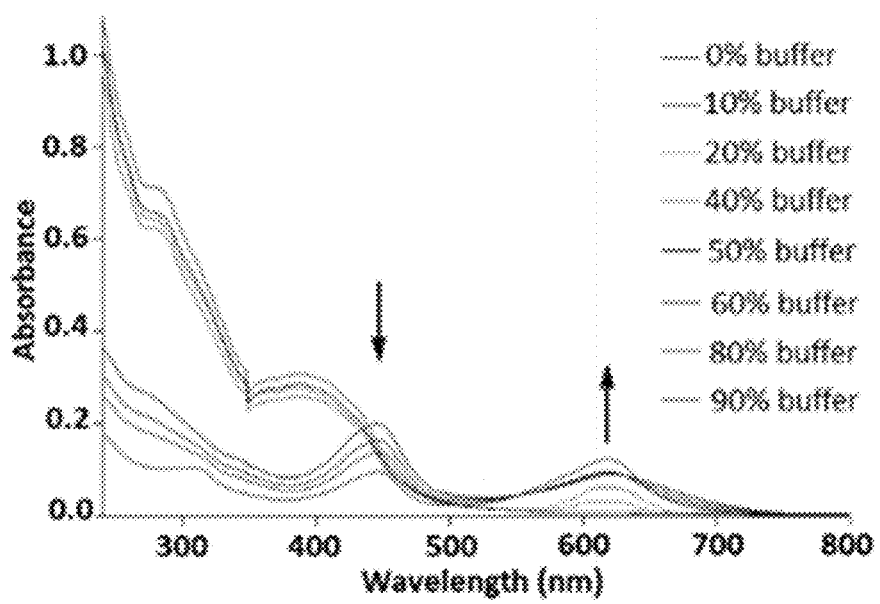
Figure 2C:
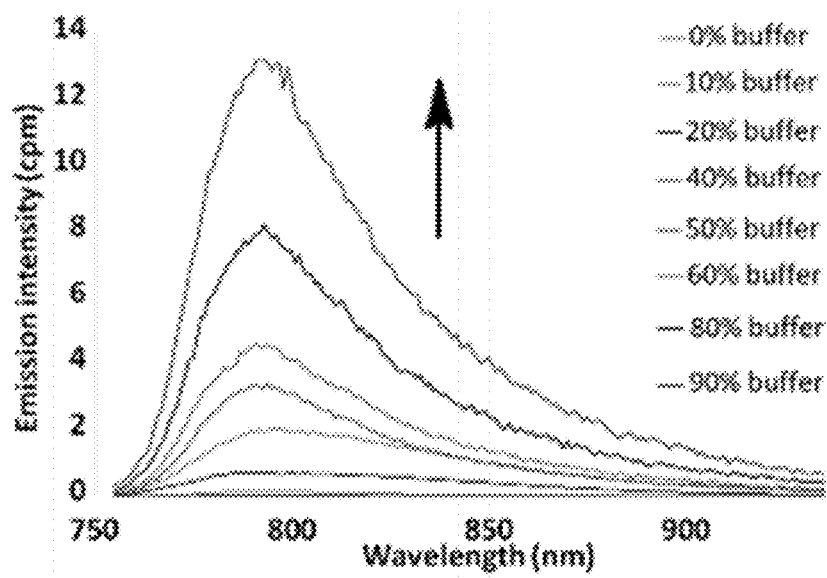
Figure 13:
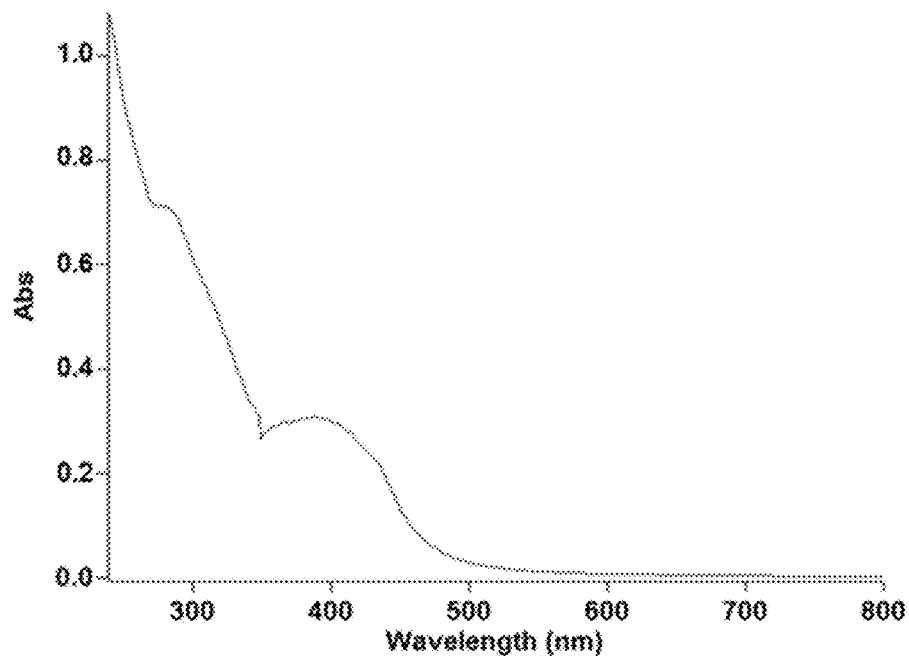
FIG. 13. UV-vis absorption spectrum of 4 (DMSO, 4 µM).
Figure 16:
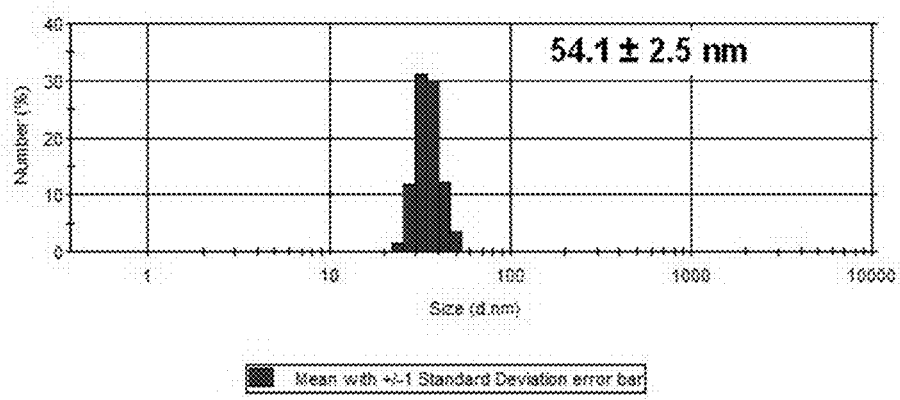
FIG. 16. DLS particle size analysis of 4 (4 µM) in 9:1 Tris buffer (10 mM Tris-HCl, pH 7.5):DMSO.
Figure 17:
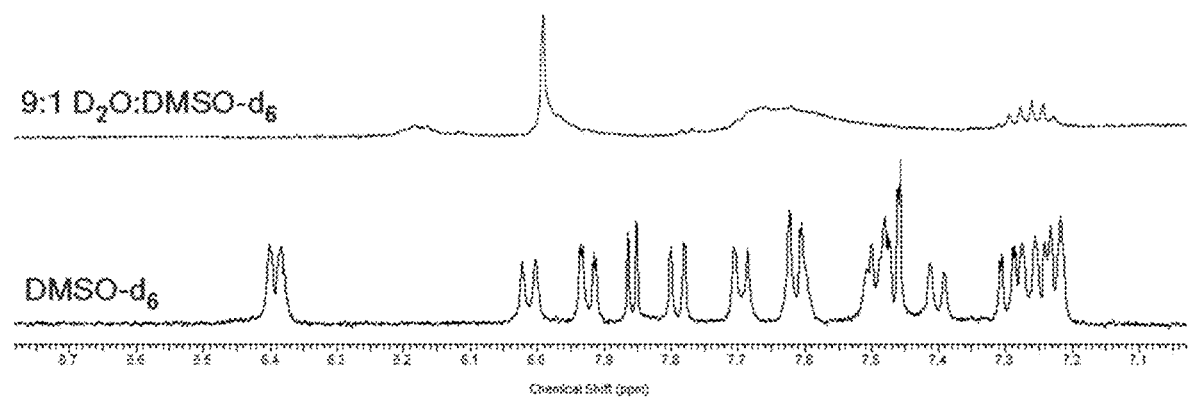
FIG. 17. $^1$H NMR spectra of 4 in DMSO-$d_6$ (bottom) and in 9:1 $D_2O$: DMSO-$d_6$ (top) collected on a Bruker NMR spectrometer at 400 MHz, [4]=50 µM.
Figure 18:
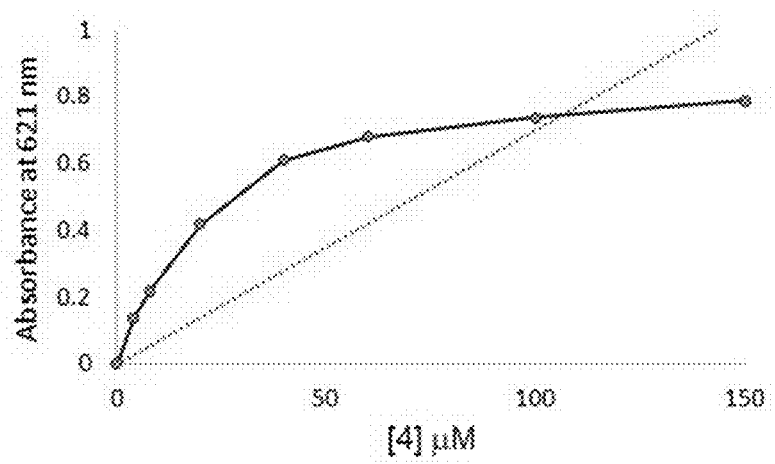
FIG. 18. The UV-vis absorbance values of 4 at 621 nm in 9:1 Tris buffer (10 mM Tris-HCl, pH 7.5):DMSO at different concentrations of 4 (0-150 µM).
Figures 19, 20:
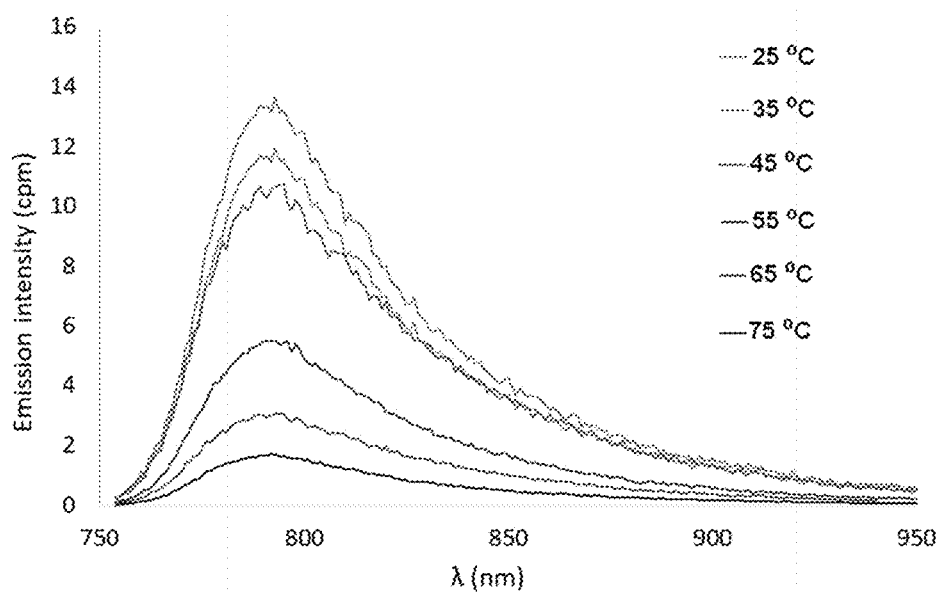
FIG. 19. Emission profile of 4 in 9:1 Tris buffer (10 mM Tris-HCl, pH 7.5):DMSO at different temperatures. $\lambda_{ex}$=445 nm, [4]=4 µM.
FIG. 20. Sequences of DNA structures used in this study (SEQ ID NOS 4-5 and 1-3, respectively, in order of appearance.
Figure 21:
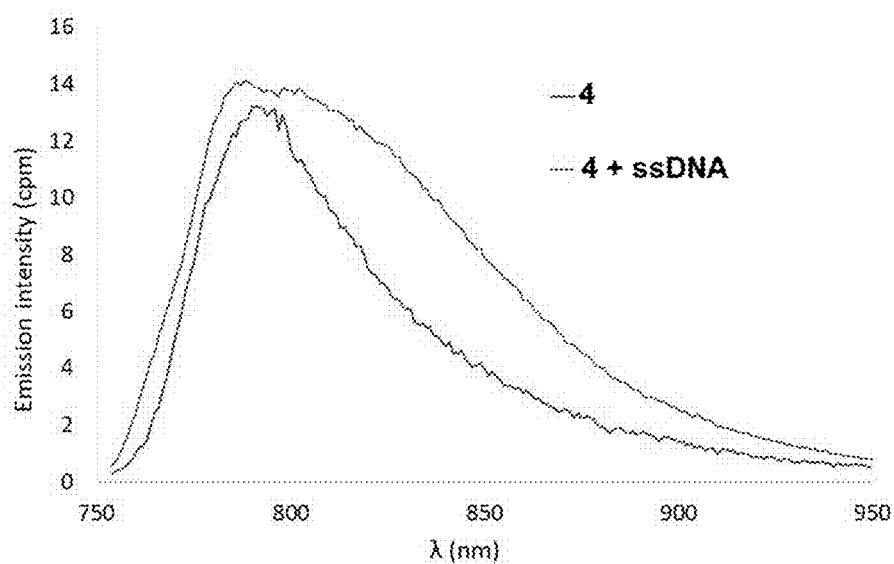
FIG. 21. Emission profile of 4 in 9:1 Tris buffer (10 mM Tris-HCl, pH 7.5):DMSO in the absence and the presence of ssDNA (8 µM). $\lambda_{ex}$=445 nm, [4]=4 µM.
Figure 22:
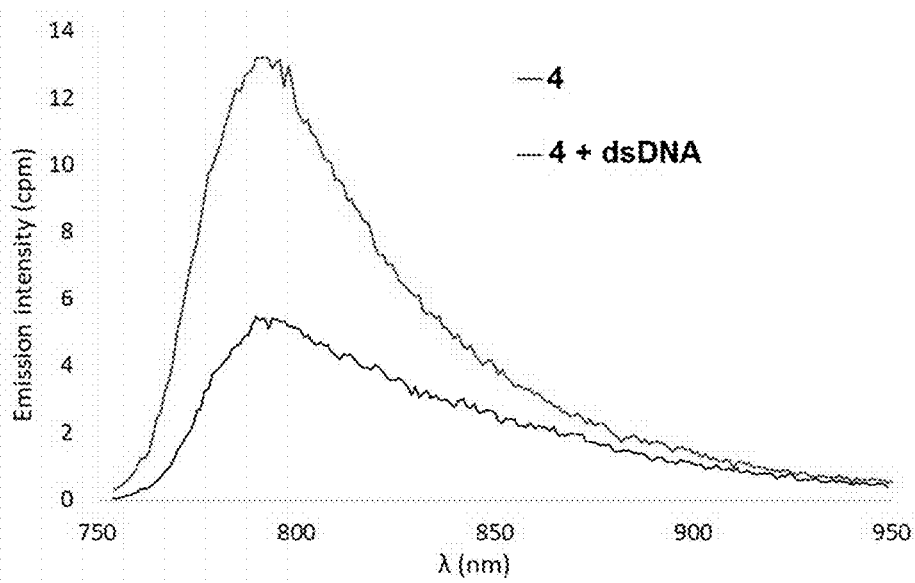
FIG. 22. Emission profile of 4 in 9:1 Tris buffer (10 mM Tris-HCl, pH 7.5):DMSO in the absence and the presence of dsDNA (8 µM). $\lambda_{ex}$=445 nm, [4]=4 µM.
Figure 23:
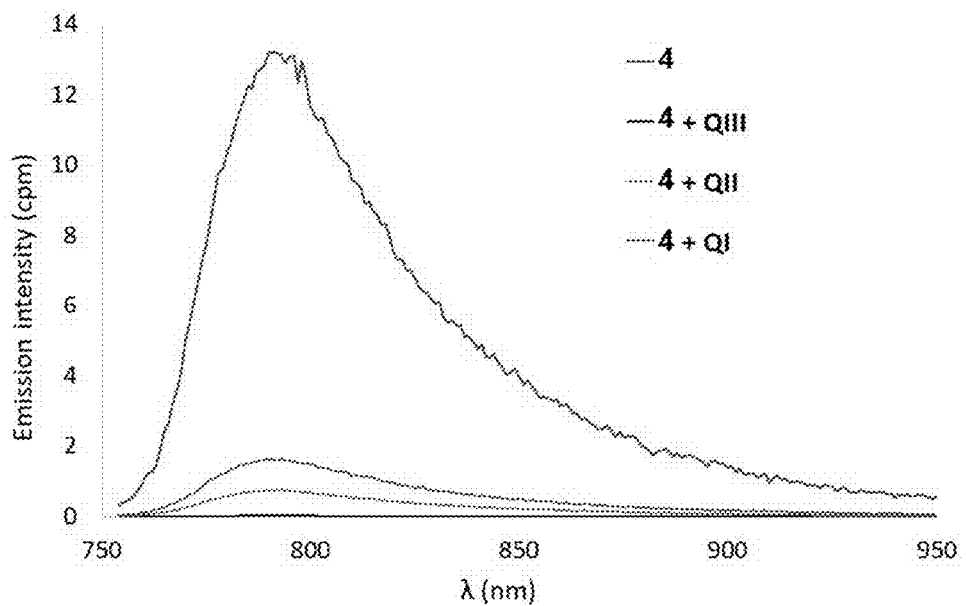
FIG. 23. Emission profile of 4 in 9:1 Tris buffer (10 mM Tris-HCl, pH 7.5):DMSO in the absence and the presence of QI, QII and QIII (8 µM). $\lambda_{ex}$=445 nm, [4]=4 µM.
Figure 24:
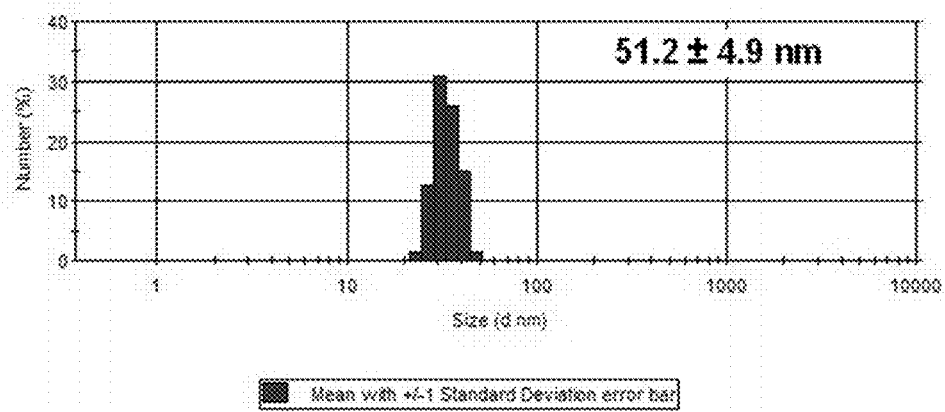
FIG. 24. DLS particle size analysis of 4 (4 µM) in the presence of ssDNA (8 µM) in 9:1 Tris buffer (10 mM Tris-HCl, pH 7.5):DMSO.
Figure 25:
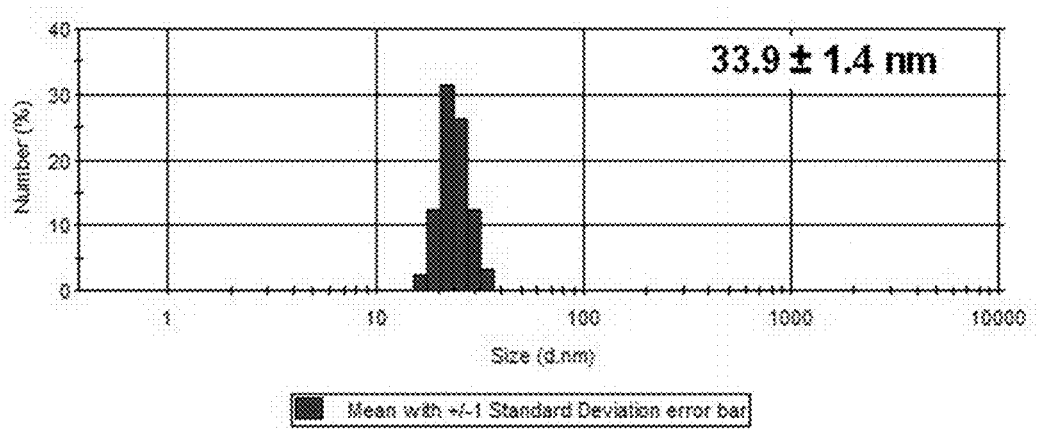
FIG. 25. DLS particle size analysis of 4 (4 µM) in the presence of dsDNA (8 µM) in 9:1 Tris buffer (10 mM Tris-HCl, pH 7.5):DMSO.
Figure 26:
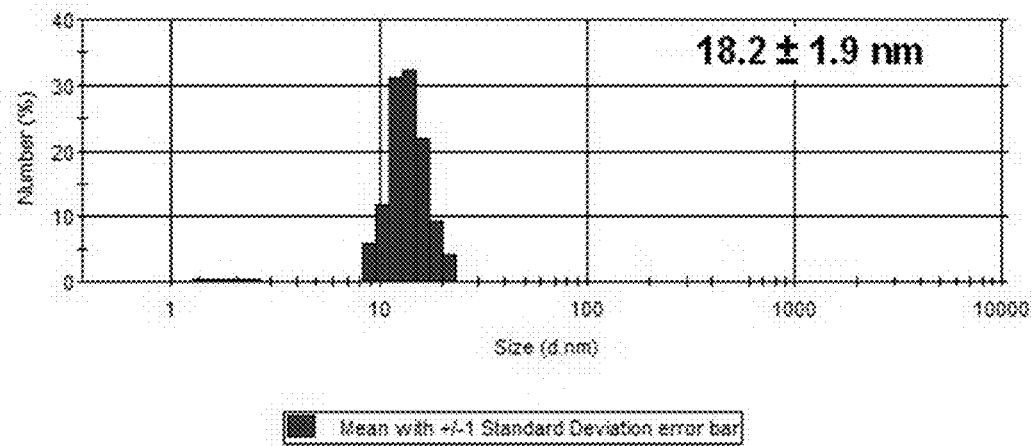
FIG. 26. DLS particle size analysis of 4 (4 µM) in the presence of QI (8 µM) in 9:1 Tris buffer (10 mM Tris-HCl, pH 7.5):DMSO.
Figure 27:
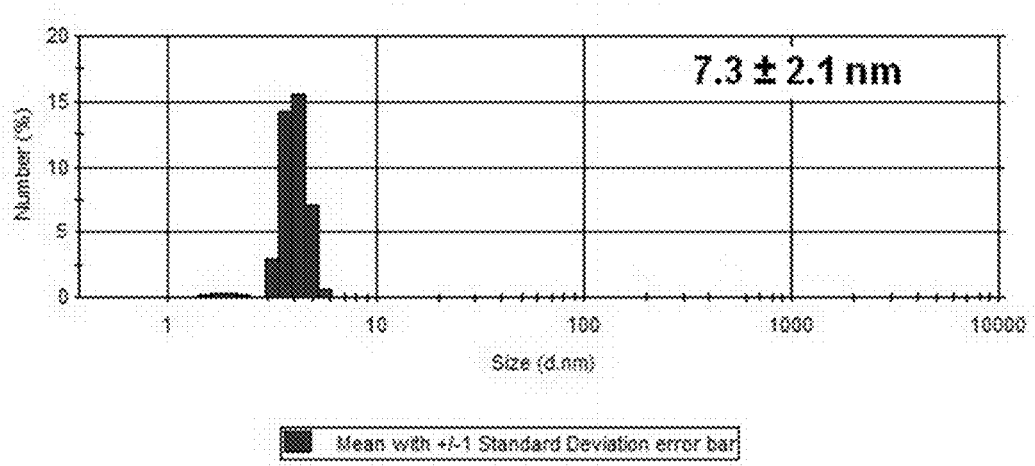
FIG. 27. DLS particle size analysis of 4 (4 µM) in the presence of QII (8 µM) in 9:1 Tris buffer (10 mM Tris-HCl, pH 7.5):DMSO.
Figure 28:
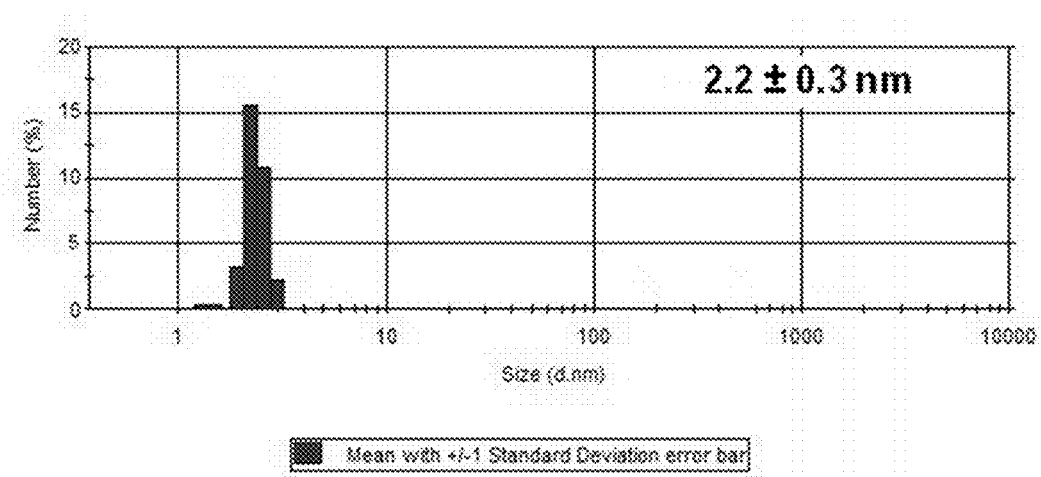
FIG. 28. DLS particle size analysis of 4 (4 µM) in the presence of QIII (8 µM) in 9:1 Tris buffer (10 mM Tris-HCl, pH 7.5):DMSO.
Figure 29:
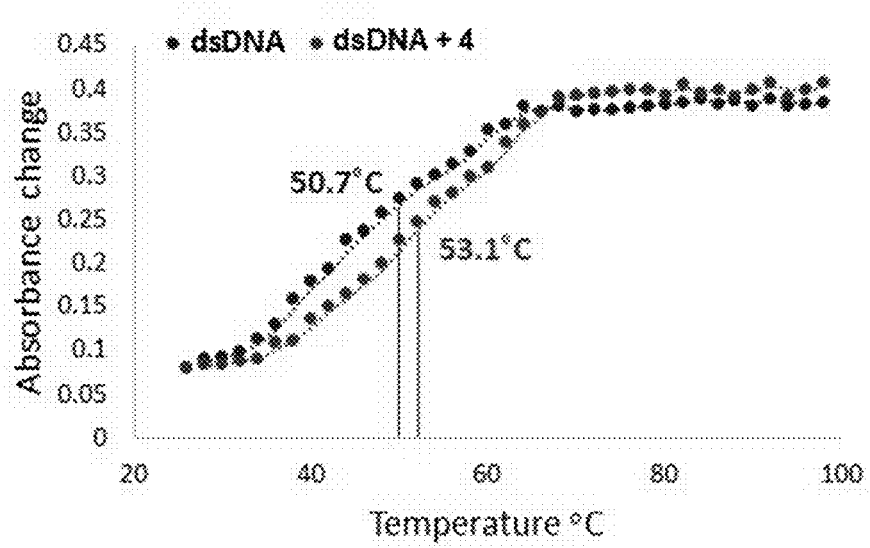
FIG. 29. Changes in UV-vis absorbance at 260 nm of dsDNA (8 µM) with and without 4 (4 µM) in 9:1 Tris buffer (10 mM Tris-HCl, pH 7.5):DMSO upon increasing temperature.
Figure 30:
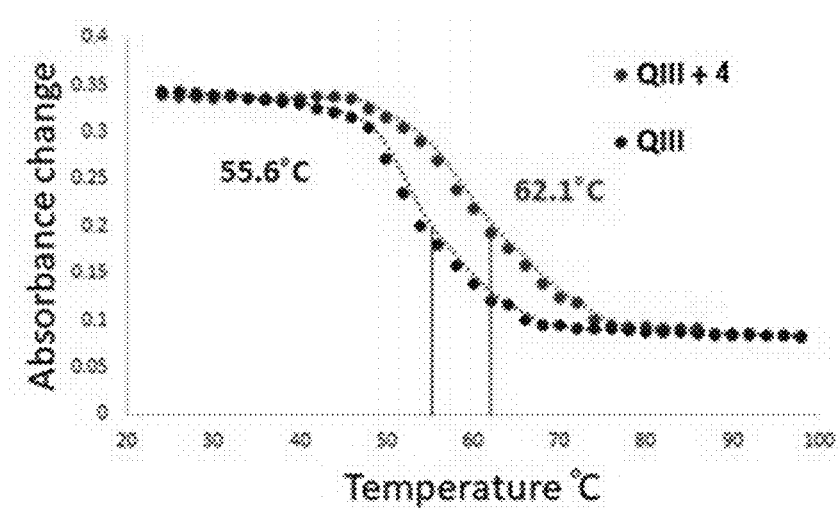
FIG. 30. Changes in UV-vis absorbance at 295 nm of QIII (8 µM) with and without 4 (4 µM) in 9:1 Tris buffer (10 mM Tris-HCl, pH 7.5):DMSO upon increasing temperature.

The UV-visible spectrum of 4 in DMSO shows a high-energy absorption band at 291 nm and a low-energy absorption band at 397 nm (FIG. 13). However, incremental addition of Tris buffer (pH 7.5) to 4 resulted in dramatic changes in the color of the solution from yellow to green (FIG. 2A) as well as in the appearance of a new absorption band at 621 nm (FIG. 2B). Concomitant with UV-vis absorption changes, gradual emergence of a NIR emission band at 785 nm was also detected in the luminescence spectrum (FIG. 2C). These spectral changes are attributed to aggregation of 4 via metal-metal and/or π-π stacking interactions, as has been previously reported for other platinum(II) complexes (Yam, et al., *Chem. Rev.* 2015, 115, 7589-7728; Mauro, et al., *Chem. Commun.* 2014, 50, 7269-7272; Chan, et al., *Acc. Chem. Res.* 2018, 51, 3041-3051; Law, et al., *ACS Appl. Mater. Interfaces* 2017, 9, 41143-41150; Li, et al., *Chem. Sci.* 2016, 7, 1653-1673; Aliprandi, et al., *Chem. Lett.* 2015, 44, 1152-1169; Chung, C et al., *J. Am. Chem. Soc.* 2011, 133, 18775-18784; Yeung, et al., *Chem. Commun.* 2010, 46, 7709-7711 and Law, et al., *ACS Appl. Mater. Interfaces* 2019, 11, 4799-4808). The self-assembly of 4 in 9:1 Tris buffer:DMSO was further confirmed by detection of nanoaggregates of 54.1±2.7 nm size by dynamic light scattering (DLS, FIG. 16). Significant signal broadening in $^1H$ NMR spectra as a function of solvent was observed as well (FIG. 17). The solvent-induced aggregation of 4 is further supported by a concentration-dependent UV-vis absorption study that shows deviation from Beer's law for the absorption band at 621 nm (FIG. 18). Finally, the disassembly of 4 as a function of increasing temperature resulted in significant attenuation of the NIR emission band at 785 nm, consistent with an emission signal that arises from intermolecular aggregation (FIG. 19).

Figure 3:
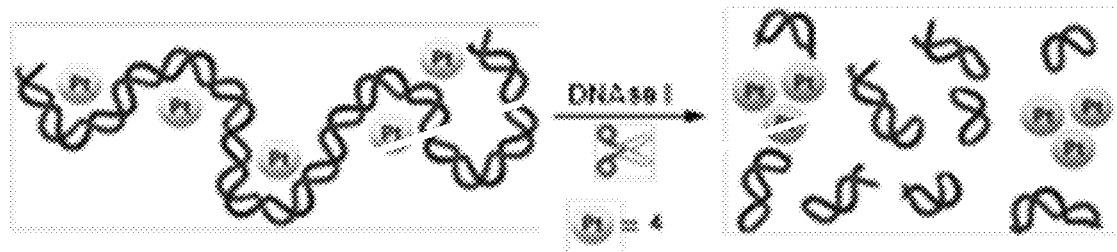
FIG. 3. Schematic illustration of the proposed DNAse I assay through self-assembly of 4 in aqueous buffer upon DNA cleavage.

Given the ability of (tetraarylethylene)Pt(II) complexes such as 1 to bind DNA structures (Gabr et al., *Inorg. Chem.* 2018, 57, 12641-12649), the potential non-covalent interaction of 4 with DNA oligomers would result in de-aggregation and shielding of the dinuclear platinum(II) complex from the aqueous environment, effectively quenching the NIR emission. Subsequent DNA cleavage by DNAse I would then release 4 back into the aqueous buffer resulting in recovery (turn-on) of NIR luminescence (FIG. 3). The dependence of NIR emission of 4/DNA ensembles on the DNA cleavage process would enable a label-free and turn-on assay of DNAse I activity.

Figure 4A:
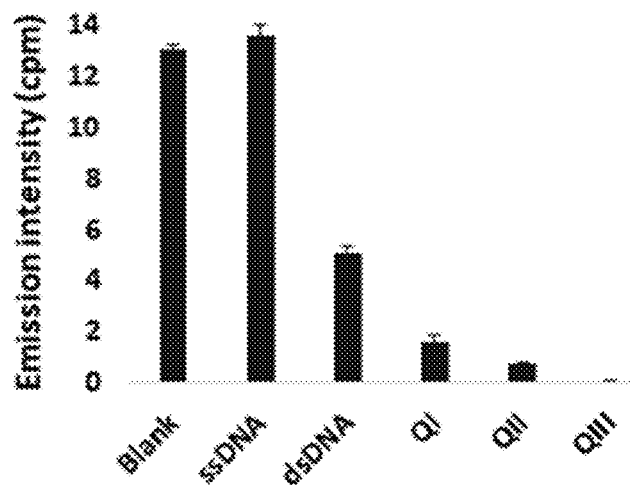
FIGS. 4A-4B. (4A) Emission intensities of 4 at 785 nm in the absence and in the presence of ssDNA, dsDNA, QI, QII and QIII; $\lambda_{ex}$=445 nm. (4B) Average particle size measured by DLS of 4 in the absence and in the presence of ssDNA, dsDNA, QI, QII and QIII. [4]=4 µM, [DNA]=8 µM. Error bars represent standard deviation (n=3).
Figure 4B:
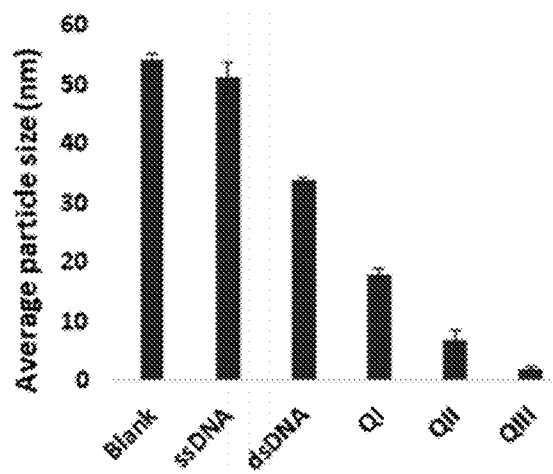
Figure 31:
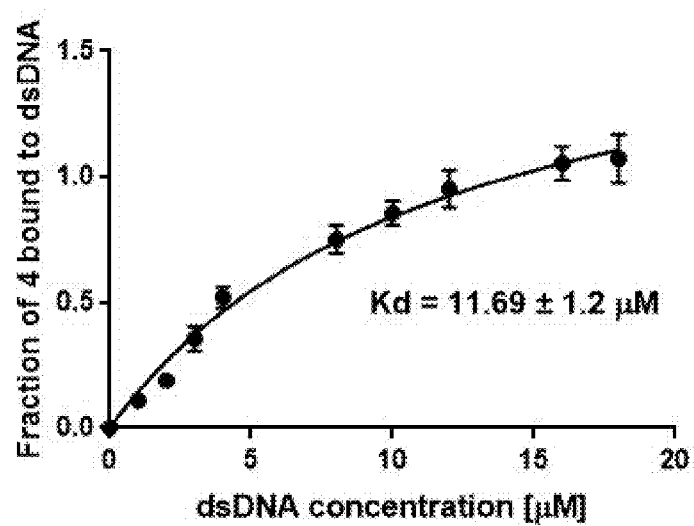
FIG. 31. Saturation binding isotherm generated by Graph-Pad Prism using various concentrations of dsDNA (0-18 µM) towards 4 (4 µM).
Figure 32:
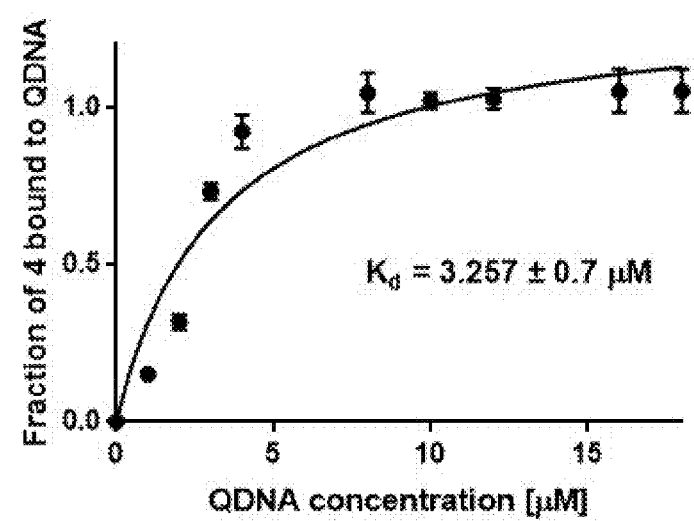
FIG. 32. Saturation binding isotherm generated by Graph-Pad Prism using various concentrations of QIII (0-18 µM) towards 4 (4 µM).

Accordingly, the luminescence response of 4 in 9:1 Tris buffer:DMSO in the presence of various DNA structures was examined (FIG. 4A and FIGS. 20-23). Minimal change in the emission profile of 4 was observed in the presence of 24-mer single-stranded DNA (ssDNA). However, considerable attenuation of the NIR emission band of 4 was achieved in the presence of a 12 base pair double-stranded DNA (dsDNA). Various metal complexes are known to bind to G-quadruplex DNA (QDNA) (Georgiades, et al., *Angew. Chem. Int. Ed.* 2010, 49, 4020-4034; Wang, et al., *Chem. Eur J.* 2010, 16, 6900-6911 and Cao, et al., *Inorg. Chem. Front.* 2017, 4, 10-32), and QDNA structures derived from three different oligonucleotides also were investigated for their effect on NIR luminescence of 4. A bimolecular G-quadruplex (QI) was prepared from (5'-(G4T4G3)2-3' (SEQ ID NO: 1)), QII is QDNA derived from the 22-mer HTelo oligomer (5'-(AG3(T2AG3)3)-3' (SEQ ID NO: 2)), and QIII is the G-quadruplex strand from the 22-mer human oncogene promoter c-myc (5'-(TGAG3T G3TAG3TG3TA2)-3' (SEQ ID NO: 3)). Remarkably, incubation of 4 with QIII resulted in virtually complete quenching of NIR luminescence (FIG. 4A). A significant reduction in the nanoaggregates particle size of 4 in the presence of QIII compared to other DNA structures investigated was additionally demonstrated in DLS studies (FIG. 4B). A stronger interaction of 4 with QIII compared to dsDNA is also indicated by UV melting curve analysis (i.e., determination of the temperature ($T_m$) at which 50% of DNA is denatured). The QIII oligomer exhibited a 6.5° C. increase in $T_m$ in the presence of 4, whereas the $T_m$ of dsDNA only increased 2.4° C. (Figures S23-S24). Consistent with these results, luminescence binding assays indicated greater affinity of 4 for QIII DNA ($K_d$=3.26 µM) compared to dsDNA ($K_d$=11.7 µM) (FIGS. 31-32).

Figure 33:
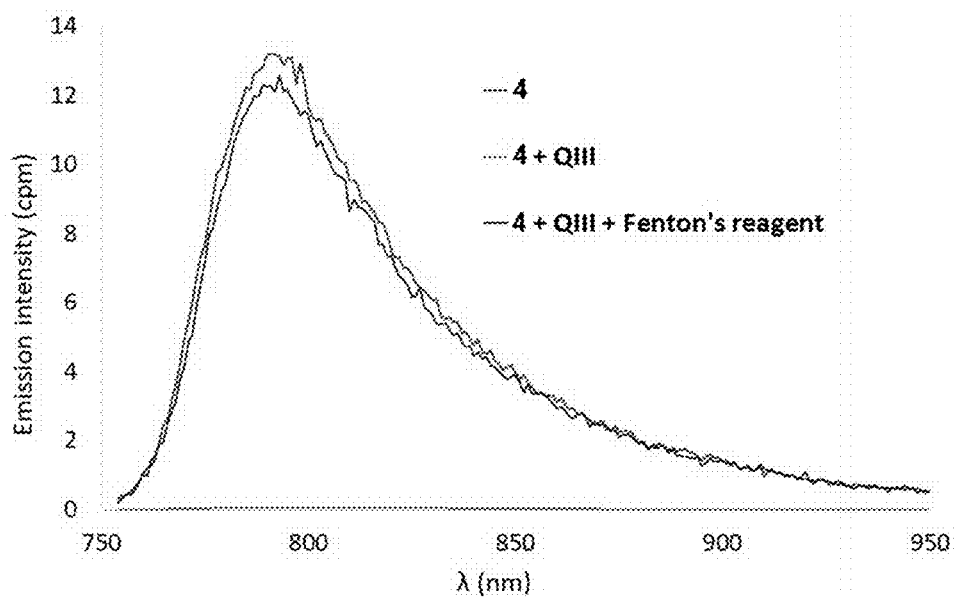
FIG. 33. Emission profile of 4 and 4/QIII in 9:1 Tris buffer (10 mM Tris-HCl, pH 7.5):DMSO in the absence and the presence of Fenton's reagent (1.4 mM $FeSO_4$+36 mM $H_2O_2$). $\lambda_{ex}$=445 nm, [4]=4 µM, QIII (8 µM).

Since complete quenching of the NIR emission of 4 was achieved in the presence of QIII DNA, this DNA oligomer was selected as the digestion substrate in 4/DNA ensembles for construction of label-free assays to monitor DNAse I activity. As a positive control and a proof of concept to test our design strategy, addition of Fenton's reagent ($Fe^{2+}$/$H_2O_2$) to a solution of the non-emissive 4/QIII DNA ensemble resulted in the recovery of NIR luminescence (FIG. 33) (Tullius, et al., *Free Radical Res. Commun.* 1991, 13, 521-529). Thus, platinum complex 4 liberated upon DNA cleavage effectively self-assembles into emissive aggregates without interference from DNA fragmentation products.

Figure 5A:
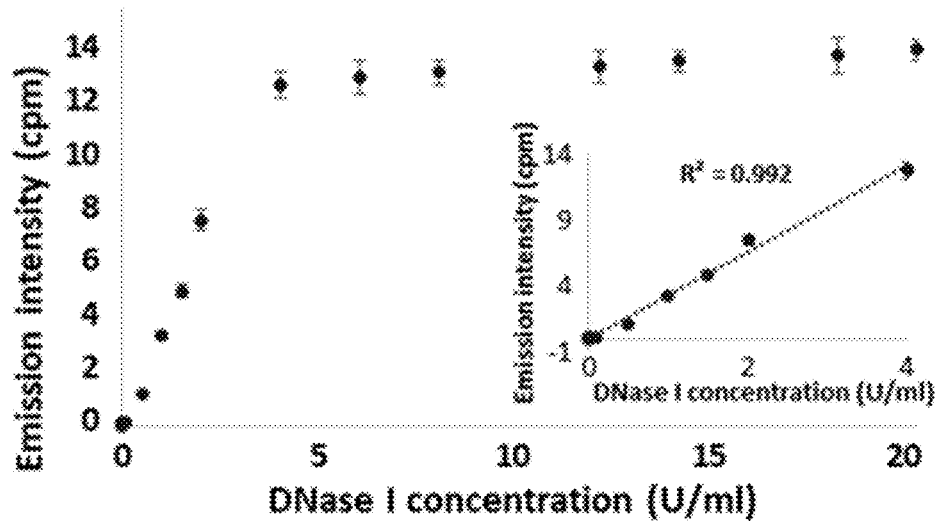
FIGS. 5A-5B. (5A) Emission intensities of 4/QIII DNA at 785 nm in the presence of different concentrations of DNAse I. Inset shows linear relationship with DNAse I concentration in the range of 0.01-4 U/mL. (5B) Emission intensities of 4/QIII DNA in the presence of different nucleases (4 U/mL) and proteins (8 µM). $\lambda_{ex}$=445 nm. Error bars represent standard deviation (n=3).
Figure 34:
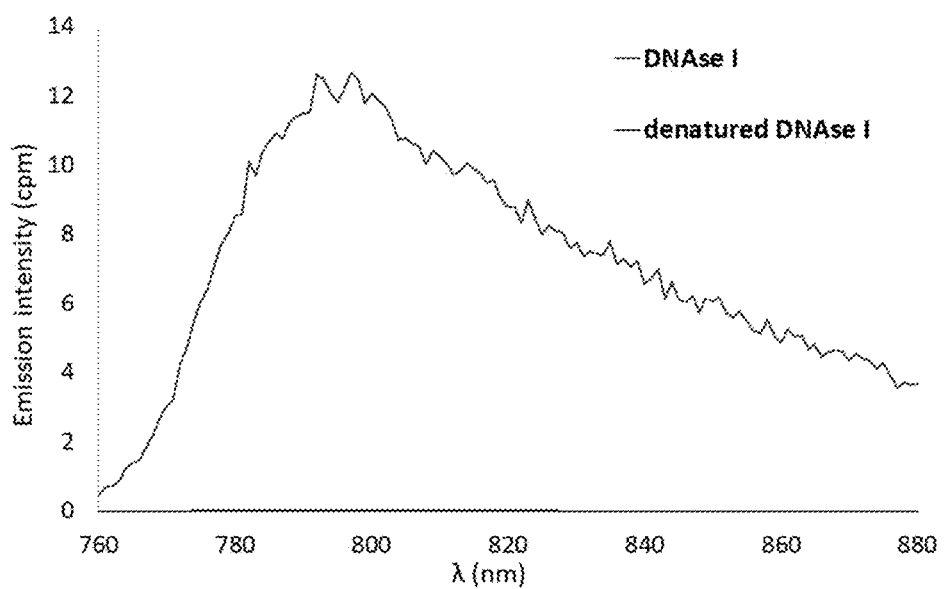
FIG. 34. Emission profile of 4/QIII ensemble in 9:1 Tris buffer (10 mM Tris-HCl, pH 7.5):DMSO in the presence of DNAse I (4 U/ml) and heat denatured DNAse I (4 U/ml) by heating at 65° C. for 10 min in the presence of 0.3 mM EDTA. $\lambda_{ex}$=445 nm, [4]=4 µM, QIII (8 µM).
Figure 35:
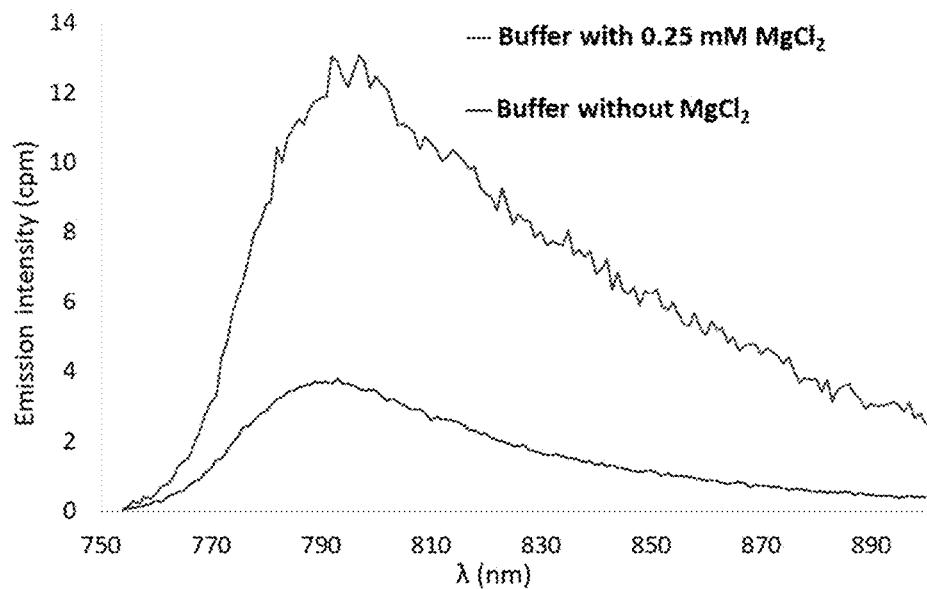
FIG. 35. Emission profile of 4/QIII ensemble in 9:1 Tris buffer (10 mM Tris-HCl, pH 7.5):DMSO in the presence of DNAse I (4 U/ml) using a reaction buffer with and without $MgCl_2$. $\lambda_{ex}$=445 nm, [4]=4 µM, QIII (8 µM).
Figure 36:
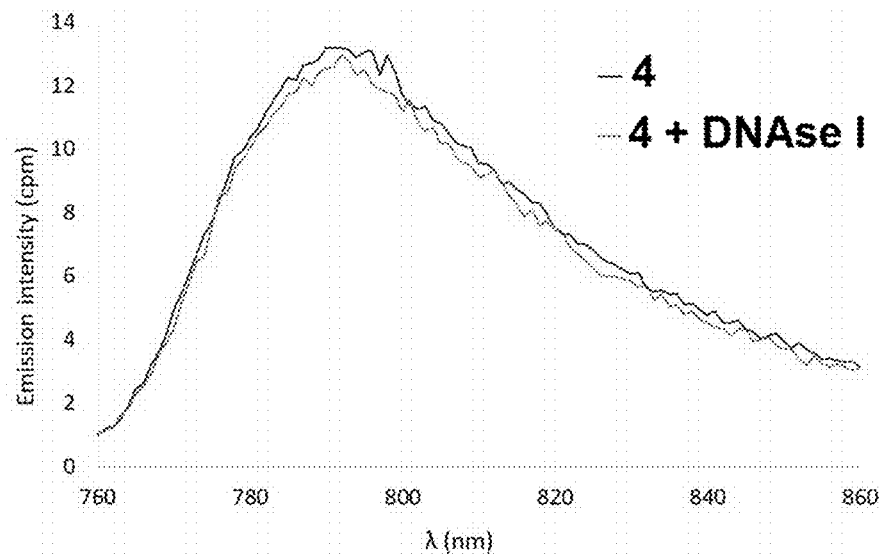
FIG. 36. Emission profile of 4 in 9:1 Tris buffer (10 mM Tris-HCl, pH 7.5):DMSO in the presence and absence of DNAse I (4 U/ml). $\lambda_{ex}$=445 nm, [4]=4 µM.

The ability of 4/QIII DNA ensembles to monitor DNAse I activity was next examined by measuring NIR emission in the presence of increasing concentrations of DNAse I (FIG. 5A). Luminescence measurements were performed in 96 well plates using a solution of 4/QIII DNA prepared from 4 µM 4 and 8 µM QIII DNA. The NIR emission intensity at 785 nm (indicative of DNA-free Pt complex aggregates) exhibited gradual enhancement in intensity as a function of DNAse I concentration and reached a plateau at ~6 U/mL DNAse I. Treatment of 4/QIII DNA ensembles with heat-inactivated DNAse I failed to elicit a luminescence response, verifying that the catalytic activity of DNAse I is crucial for NIR emission (FIG. 34). Since DNAse I is a $Mg^{2+}$-dependent enzyme (Baranovskii, et al., *Biochemistry* (Moscow) 2004, 69, 587-601 and Keyel, P. A. *Dev. Biol.* 2017, 429, 1-11), the degradation of 4/QIII DNA by DNAse I was performed in a reaction buffer without $Mg^{2+}$, which also resulted in considerable attenuation of NIR emission (FIG. 35). In the absence of QM, addition of DNAse I to 4 in 9:1 Tris buffer:DMSO resulted in negligible change in its emission profile (FIG. 36). These results confirm that NIR emission intensity of 4/QIII DNA is correlated with QIII DNA cleavage by DNAse I.

Figure 5B:
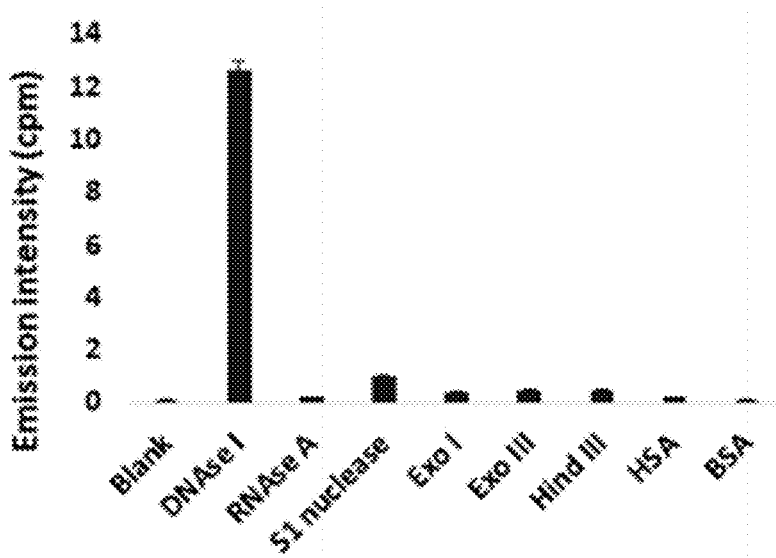
Figure 37:
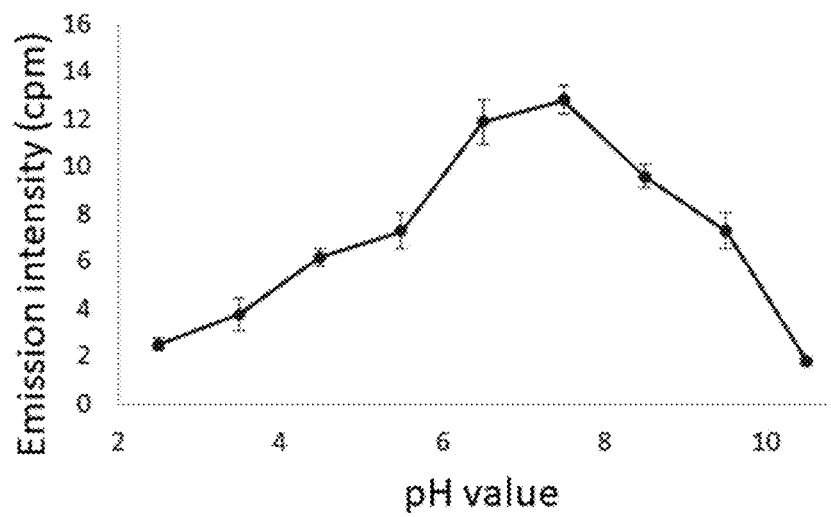
FIG. 37. NIR Emission intensity of 4/QIII ensemble in 9:1 Tris buffer (10 mM Tris-HCl):DMSO in the presence of DNAse I (4 U/ml) at different pH values. $\lambda_{ex}$=445 nm, [4]=4 µM, QIII (8 µM). Error bars represent standard deviation (n=3).
Figure 38:
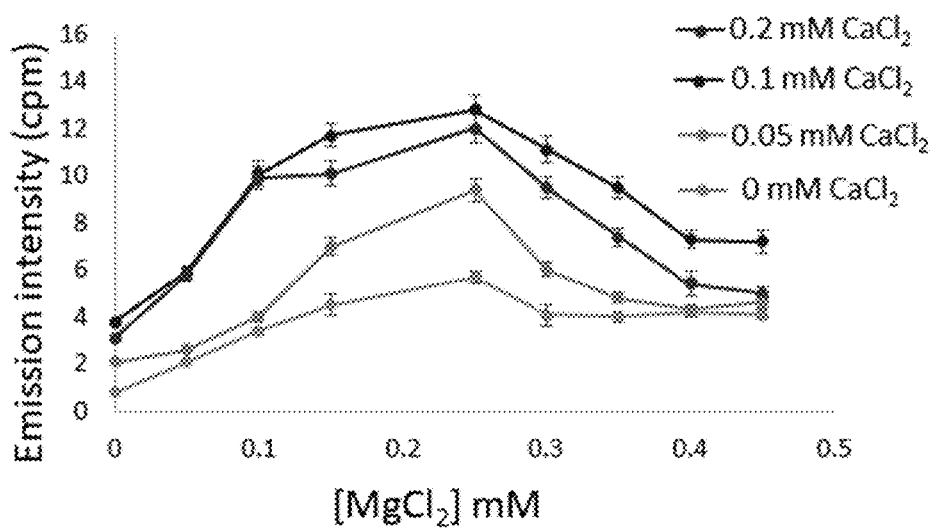
FIG. 38. NIR Emission intensity of 4/QIII ensemble in 9:1 Tris buffer (10 mM Tris-HCl, pH 7.5):DMSO in the presence of DNAse I (4 U/ml) at different combinations of $MgCl_2$ and $CaCl_2$. $\lambda_{ex}$=445 nm, [4]=4 µM, QIII (8 µM). Error bars represent standard deviation (n=3).

The inset in FIG. 5A reveals a linear relationship in the DNAse I concentration range of 0.01-4 U/mL. In addition, the detection limit of DNAse I is estimated to be 0.002 U/mL (3 $S_0$/S; $S_0$ is the standard deviation and S is the slope of the calibration curve). Significantly, the 4/QIII DNA ensemble is more sensitive in terms of detection of DNAse I activity than previously reported fluorescence-based DNAse I assays (Table S1). To address the selectivity of this method for DNAse I, other nucleases (RNAse A, S1 nuclease, Exonuclease I (Exo I), Exonuclease III (Exo III) and Hind III) and proteins (human serum albumin (HSA), bovine serum albumin (BSA)) were screened for their abilities to elicit NIR emission of 4/QIII DNA. In each case minimal to no NIR emission was detected (FIG. 5B), demonstrating the selectivity of this assay for DNAse I. Optimal assay pH was determined to be 7.5, and highest DNAse I activity was observed in the presence of 0.1 mM $CaCl_2$ and 0.25 mM $MgCl_2$ (FIGS. 37-38).

Figure 6A:
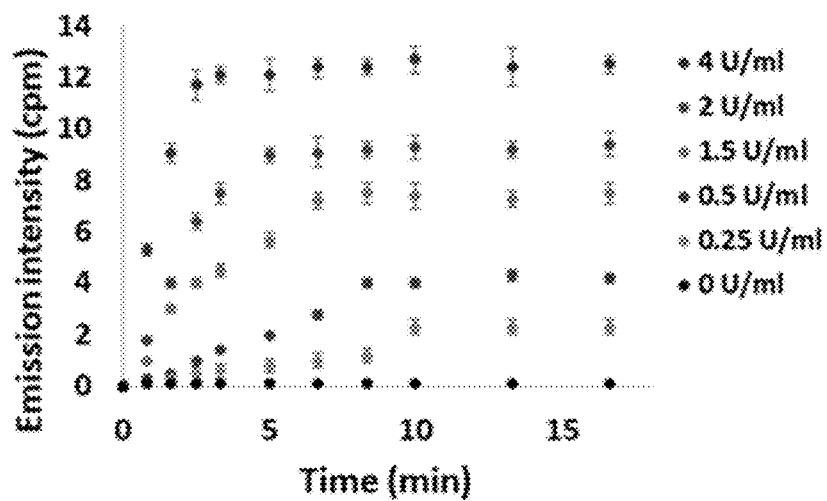
FIGS. 6A-6B. (6A) Emission intensities of 4/QIII DNA at 785 nm versus time at different DNAse I concentrations, $\lambda_{ex}$=445 nm. (6B) Lineweaver-Burk double reciprocal plot of initial digestion rate ($1/V_0$) versus substrate concentration (1/[S]). Error bars represent standard deviation (n=3).
Figure 6B:
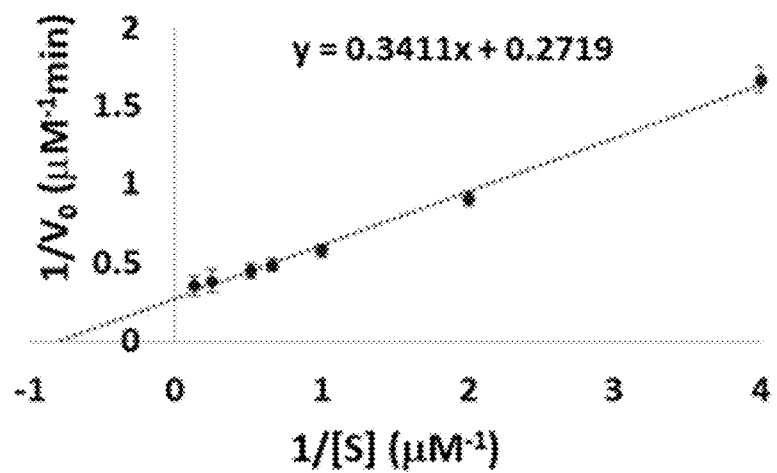
Figure 7:
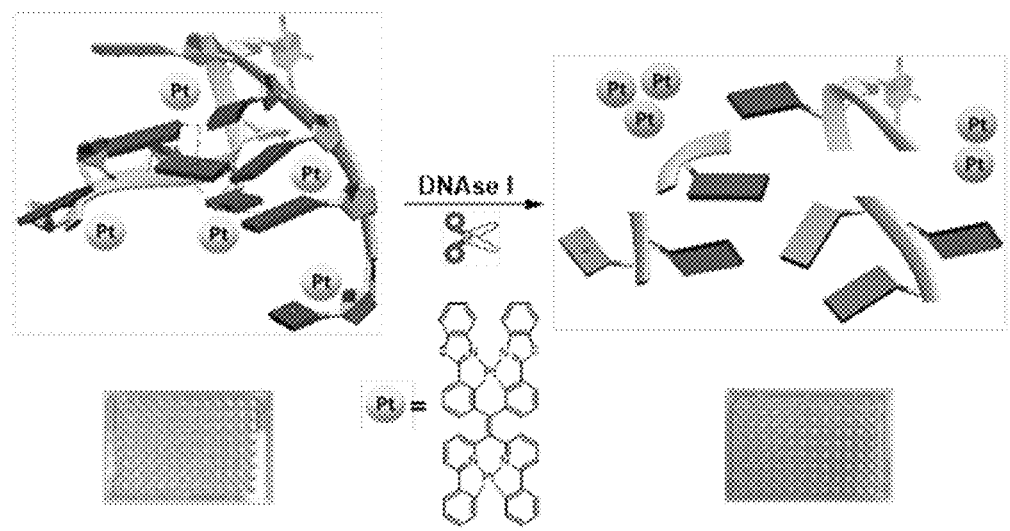
FIG. 7. Schematic of assay for detecting DNAse I.
Figure 8:
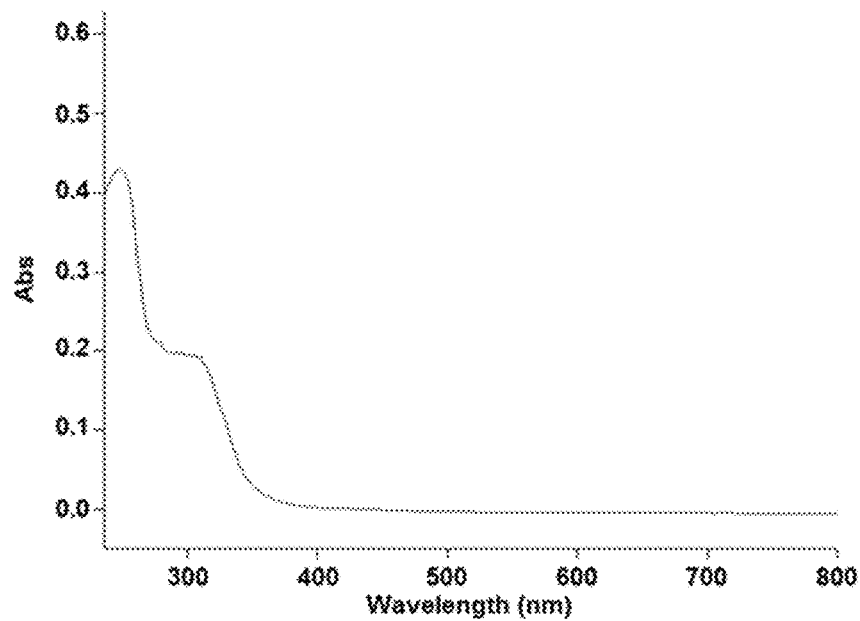
FIG. 8. UV-vis absorption spectrum of B (DMSO, 2 µM).
Figure 9:
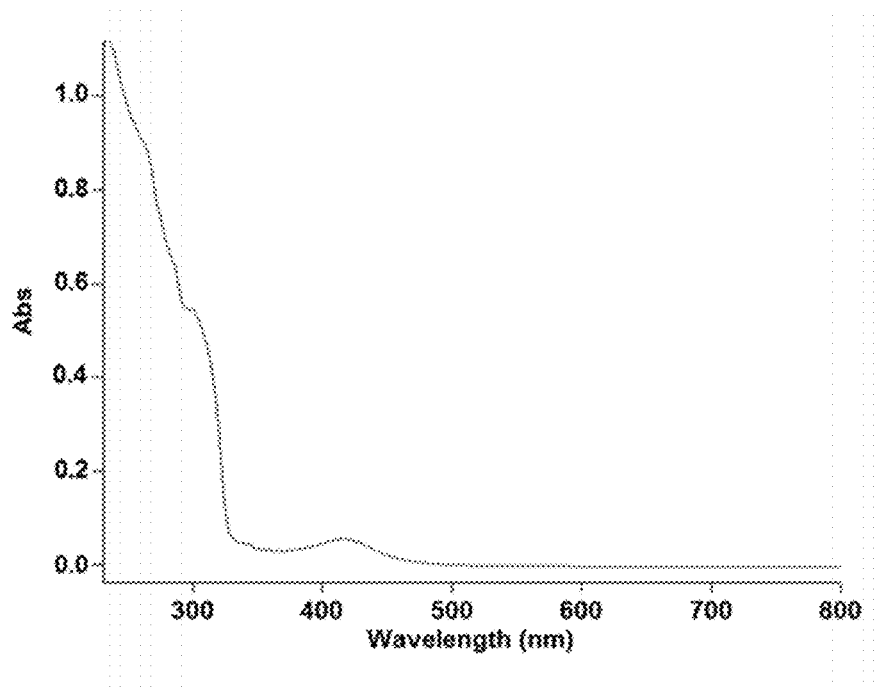
FIG. 9. UV-vis absorption spectrum of 2 (DMSO, 6 µM).
Figure 10:
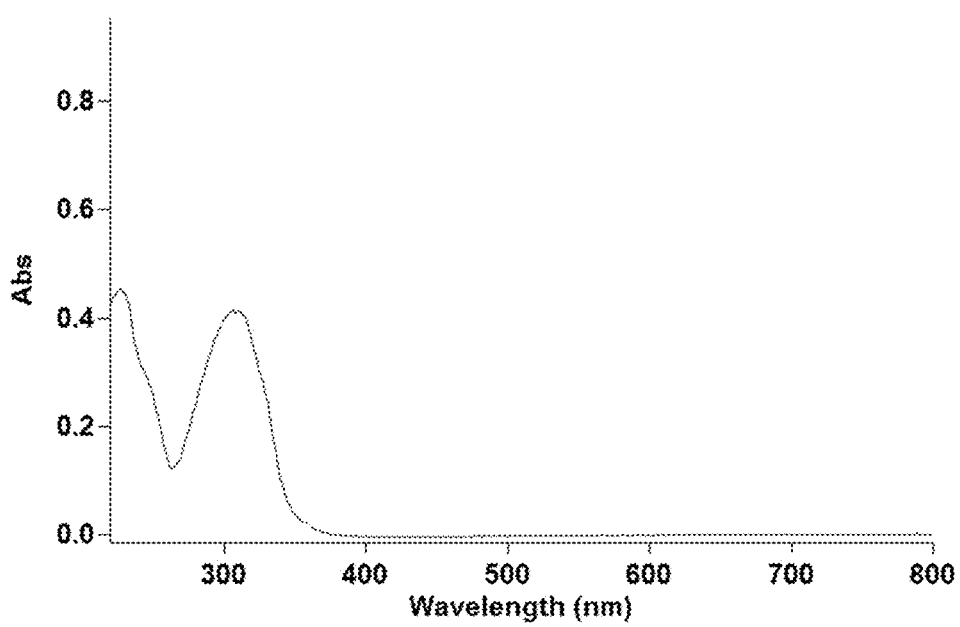
FIG. 10. UV-vis absorption spectrum of E (DMSO, 4 µM).
Figure 11:
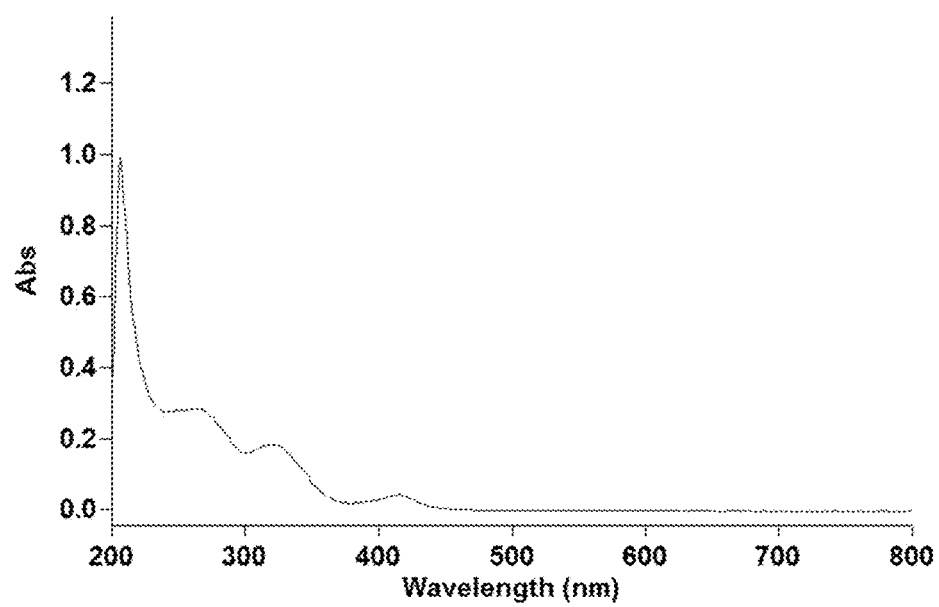
FIG. 11. UV-vis absorption spectrum of 3 (DMSO, 4 µM).
Figure 12:
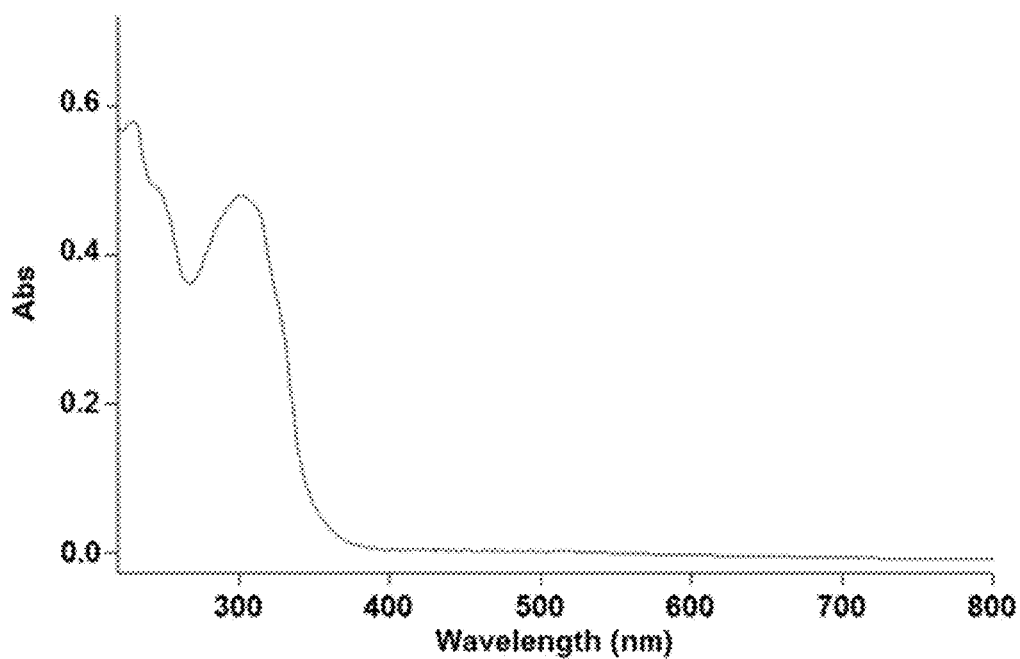
FIG. 12. UV-vis absorption spectrum of G (DMSO, 4 µM).
Figure 39:
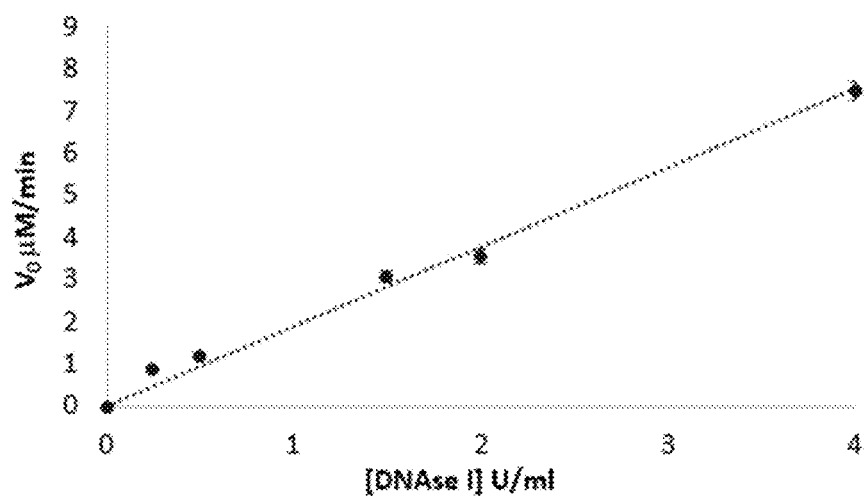
FIG. 39. Initial cleavage velocity ($V_0$) of 4/QIII ensemble as a function of DNAse I concentration.

Time curves for digestion of 4/QIII DNA as a function of DNAse I concentration (0-4 U/mL) are displayed in FIG. 6A. In the absence of DNAse I, negligible NIR emission can be detected over the incubation time. However, a rapid enhancement in the NIR emission signal is observed in the presence of 0.25 U/mL DNAse I. The emission signal plateaus after only 10 minutes, demonstrating the quick response of this assay to DNAse I activity. The digestion reaction rate increased gradually in the presence of higher concentrations of DNAse I (FIG. 6A), and a linear relationship between initial digestion rate ($V_0$) and DNAse I concentration was observed (FIG. 39). In order to further verify the validity of this method to study DNAse I kinetics, the initial digestion rates ($V_0$) were determined as a function of 4/QIII DNA concentration ([S]). A Lineweaver-Burk double reciprocal plot of 1/$V_0$ versus 1/[S] revealed a linear correlation (FIG. 6B) with a Michaelis-Menten constant ($K_m$) of 1.26±0.3 µM. This calculated $K_m$ value is in good agreement with previously reported $K_m$ values for DNAse I, which fall in the range of 0.4-2.19 µM (Jang, et al., *J. Biomol. Screen.* 2015, 20, 202-211 and Zhao, et al., *RSC Adv.* 2017, 7, 30911-30918). These results show that the 4/QIII DNA ensemble is an efficient real-time assay of DNAse I activity and its kinetic parameters.

Figure 40:
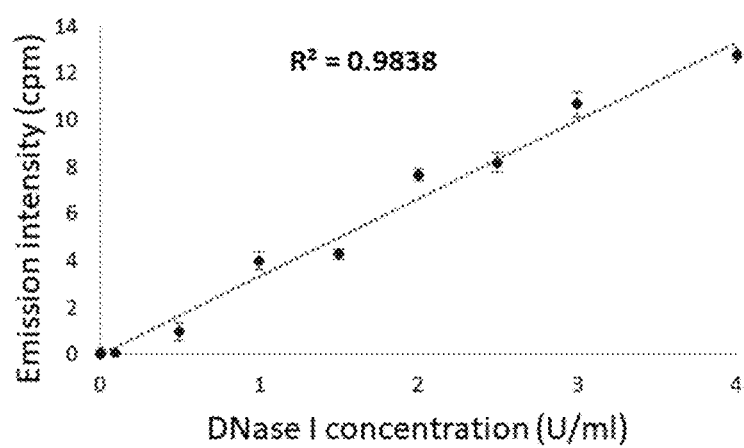
FIG. 40. The linear correlation of NIR emission intensity of 4/QIII ensemble and DNAse I concentrations in human serum samples. $\lambda_{ex}$=445 nm, [4]=4 µM, QIII (8 µM). Error bars represent standard deviation (n=3).

In order to evaluate the performance of 4/QIII DNA as a DNAse I sensor in complex matrices, this method was used in detecting DNAse I activity in human serum samples. Various concentrations of DNAse I (0-4 U/mL) were added to human serum samples and subjected to the assay procedure. A linear correlation between NIR emission signal of 4 and DNAse I concentration in human serum samples was observed (FIG. 40). In addition, assessing DNAse I activity in human serum samples spiked with 4 different concentrations of DNAse I (0.15, 0.5, 1 and 4 U/mL) revealed satisfactory reproducibility and precision (Table S2). These results demonstrate the potential of this system to detect DNAse I activity in real clinical samples. The assay was validated for high-throughput screening (HTS) mode by calculating the Z' factor, representing the ratio of data signal variability (standard deviation) to dynamic range (i.e., difference in luminescence signal for positive and negative controls) (Zhang, et al., *J. Biomol. Screen.* 1999, 4, 67-73). The mean Z' factor of the assay is 0.54 (see Supporting Information), which is indicative of a high quality assay (Z'≤0.5) (Zhang, et al., *J. Biomol. Screen.* 1999, 4, 67-73). This was accompanied by signal-to-background (S/B) ratio and signal-to-noise (S/N) ratio of 12.7 and >2000, respectively. These parameters confirm the potential suitability of 4/QIII DNA assay for HTS of DNAse I activity.

Figure 41:
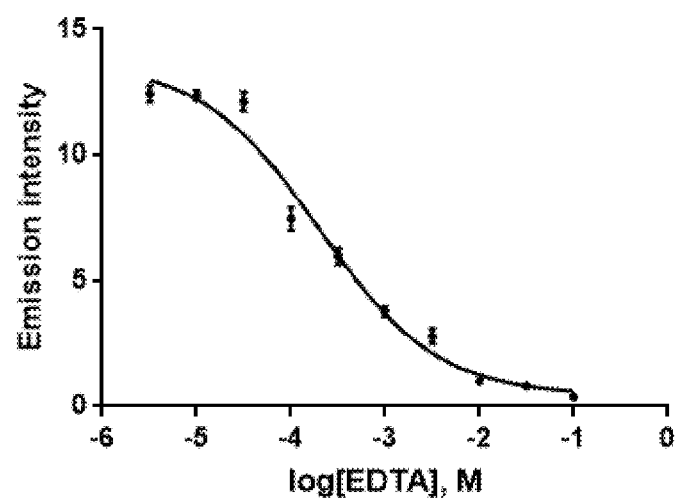
FIG. 41. Dose-response curve in the presence of different concentrations of EDTA based on NIR emission intensity of 4/QIII ensemble. $\lambda_{ex}$=445 nm, [4]=4 µM, [QIII]=8 µM, [DNAse I]=4 U/ml. Error bars represent standard deviation (n=3).
Figure 42:
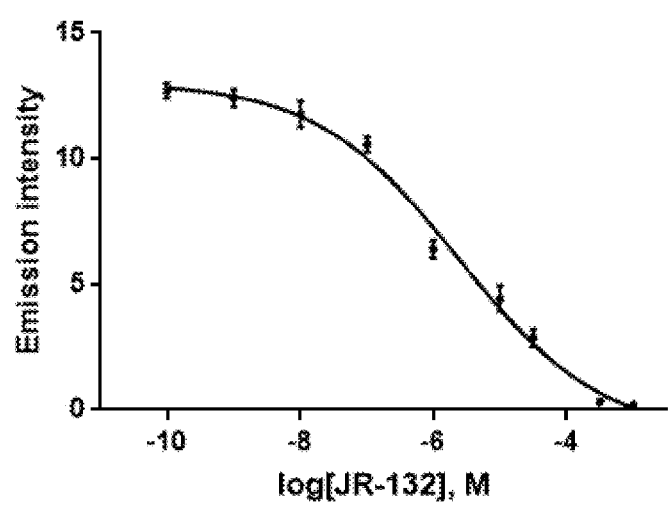
FIG. 42. Dose-response curve in the presence of different concentrations of JR-132 based on NIR emission intensity of 4/QIII ensemble. $\lambda_{ex}$=445 nm, [4]=4 µM, [QIII]=8 µM, [DNAse I]=4 U/ml. Error bars represent standard deviation (n=3).
Figure 43:
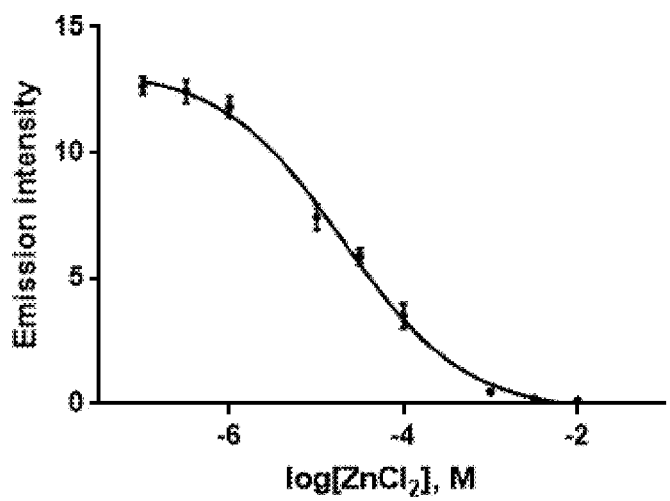
FIG. 43. Dose-response curve in the presence of different concentrations of $ZnCl_2$ based on NIR emission intensity of 4/QIII ensemble. $\lambda_{ex}$=445 nm, [4]=4 µM, [QIII]=8 µM, [DNAse I]=4 U/ml. Error bars represent standard deviation (n=3).
Figure 44:
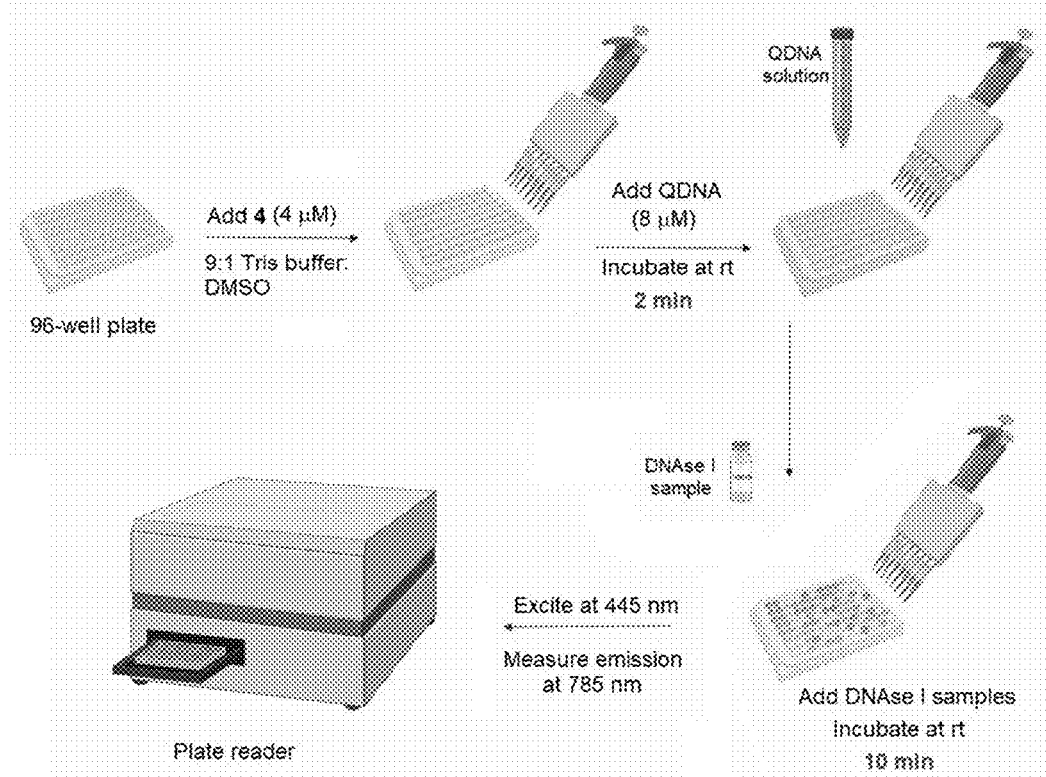
FIG. 44. Schematic illustration of the general procedure of the developed DNAse I assay.
Figure 45:
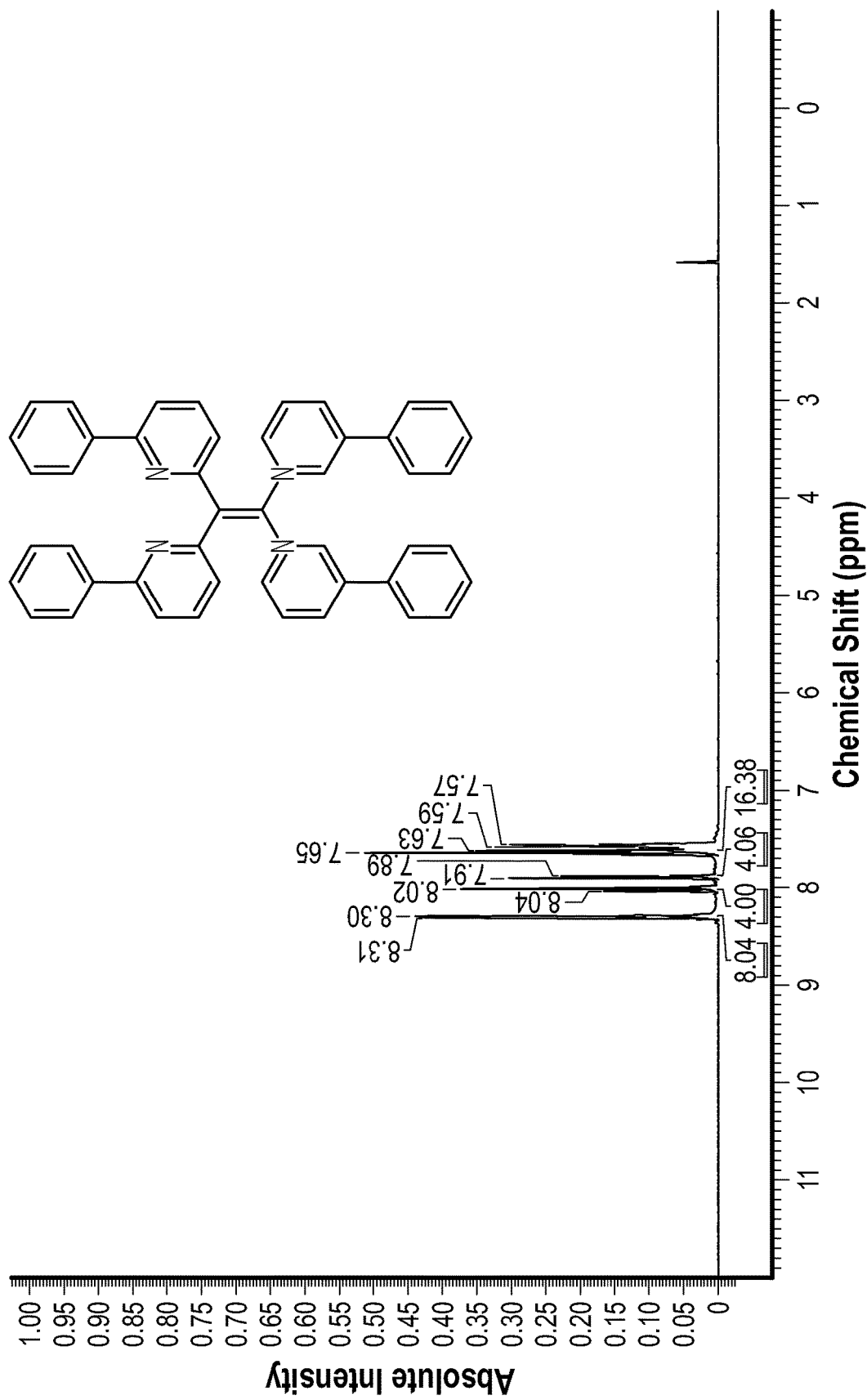
FIG. 45. NMR spectra of certain compounds described herein.
Figure 45:
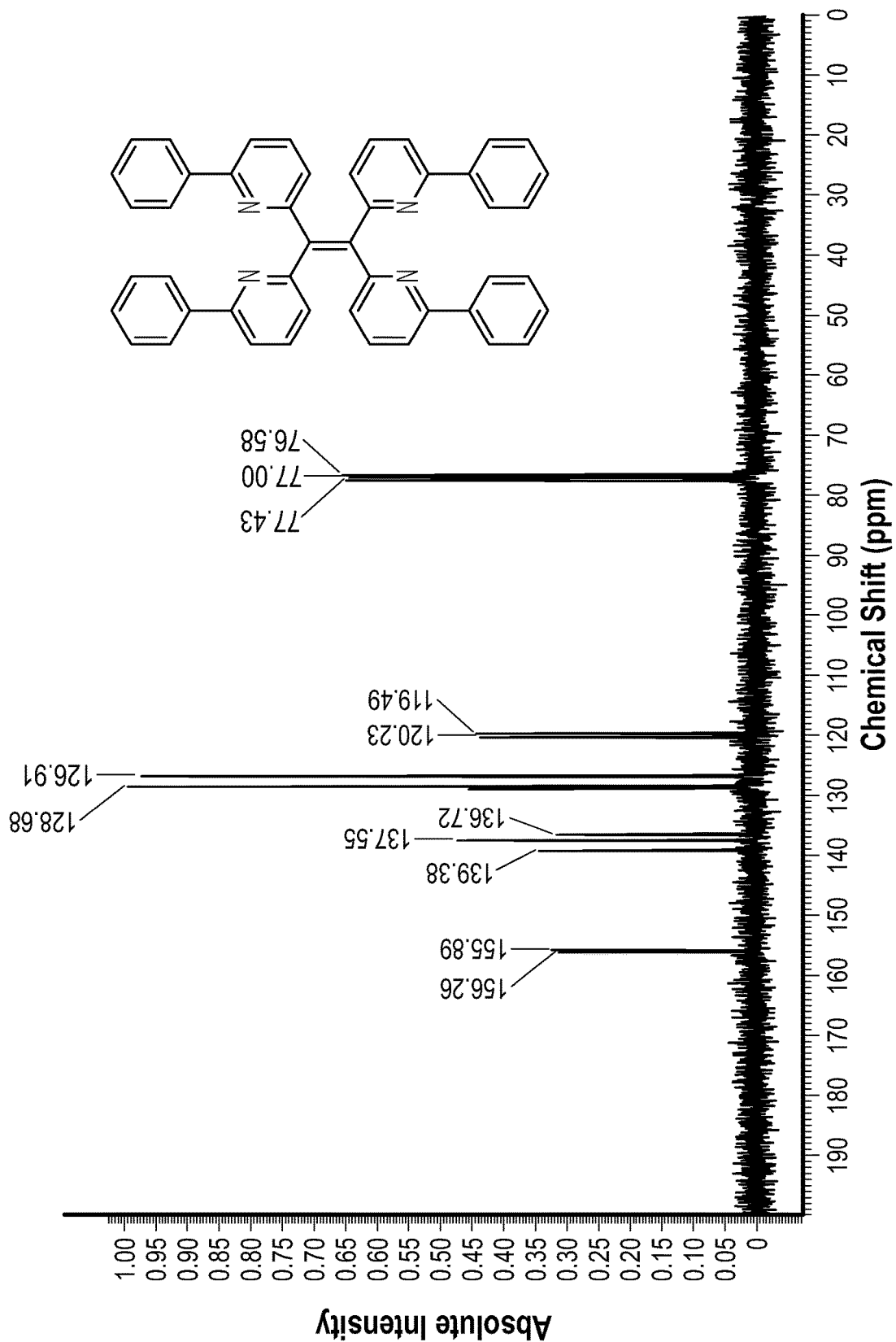
Figure 45:
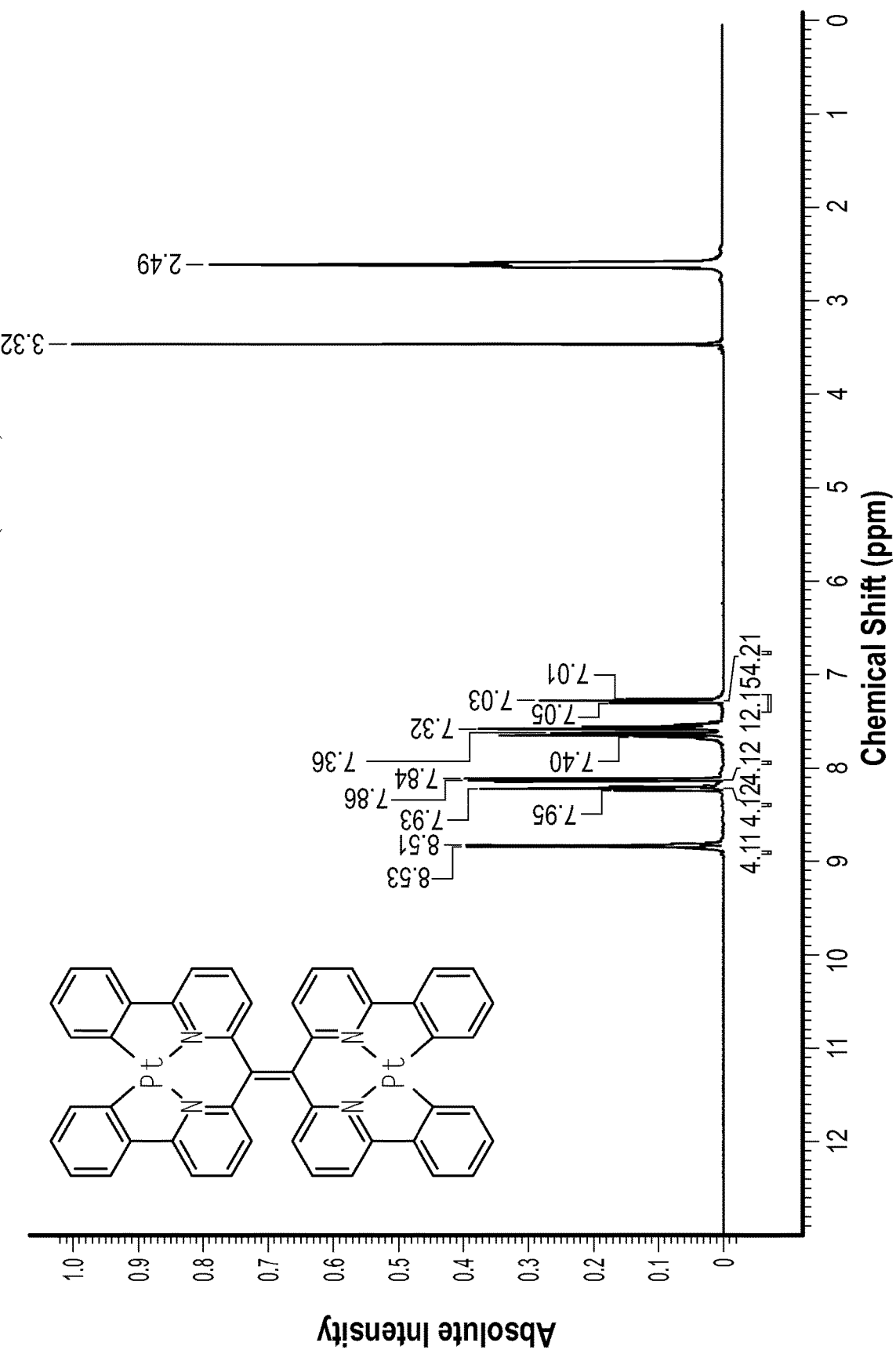
Figure 45:
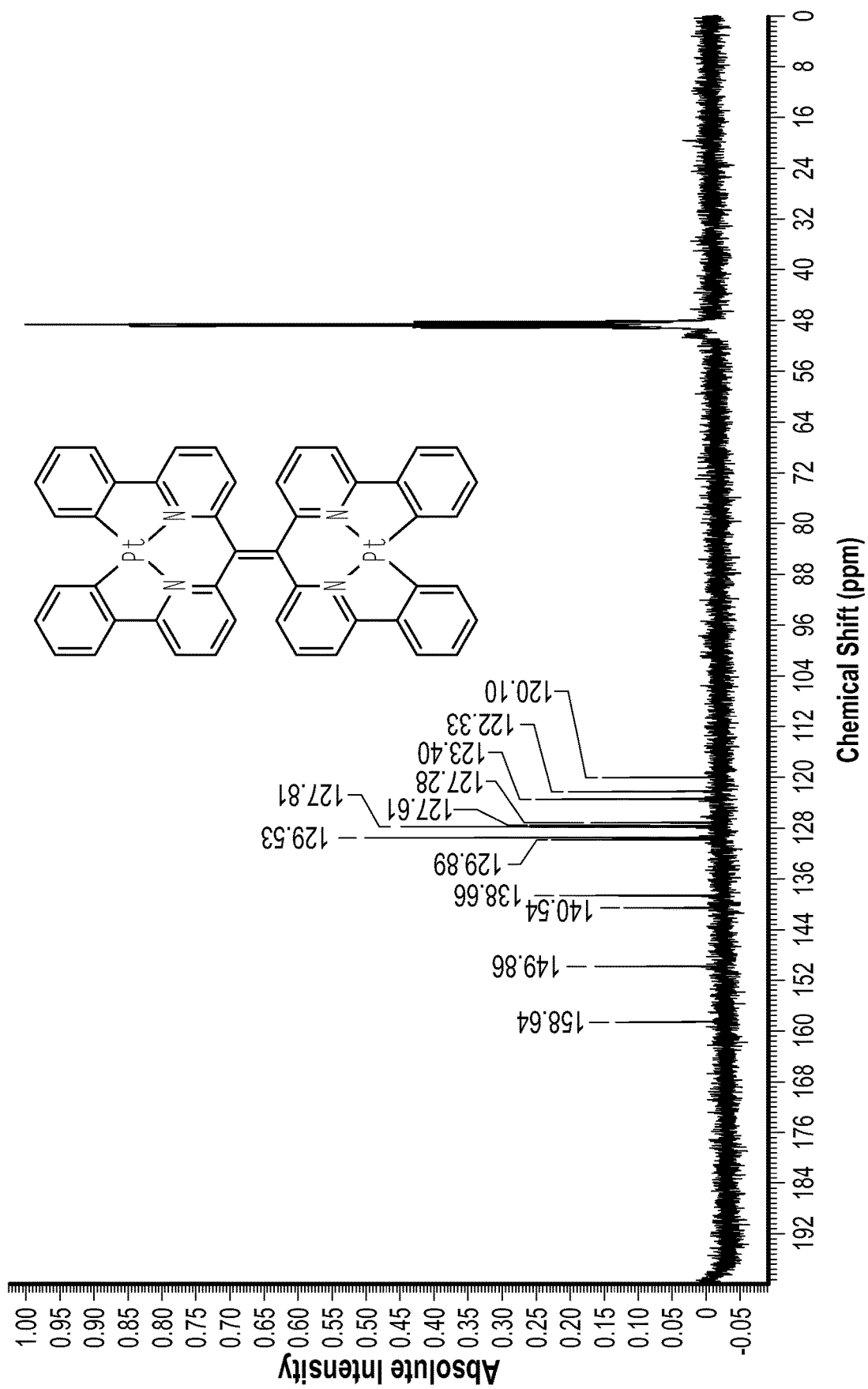
Figure 45:
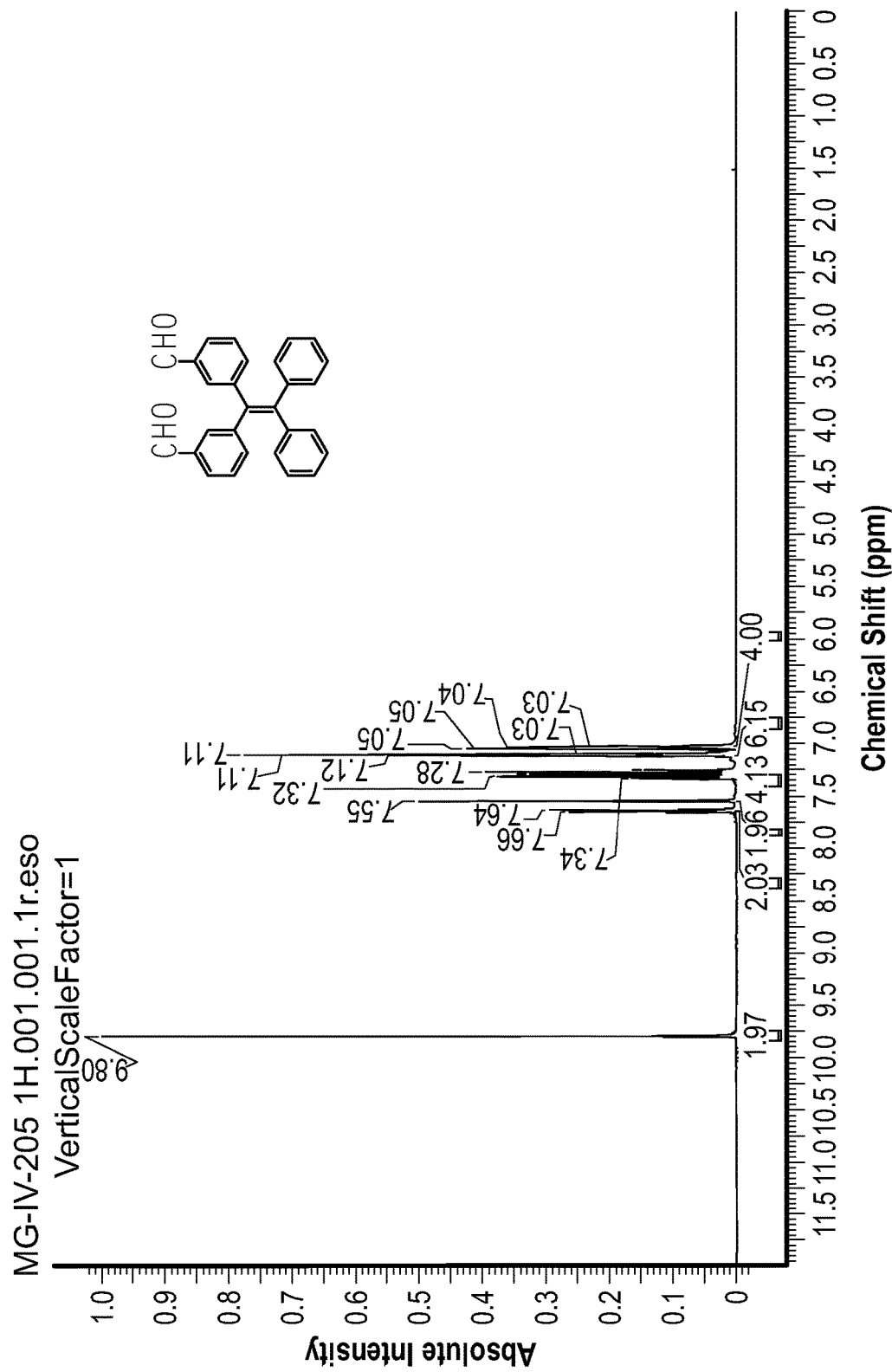
Figure 45:
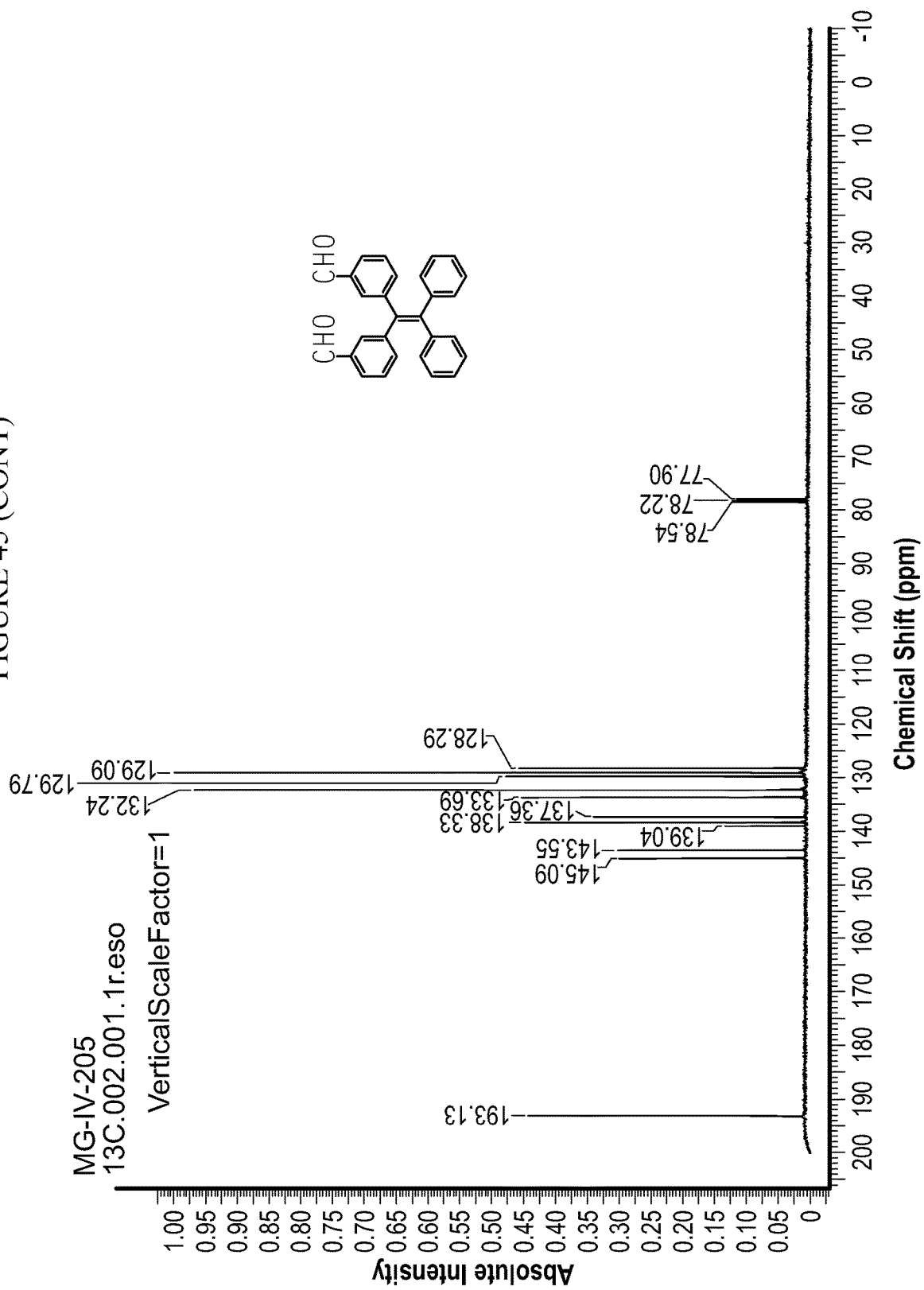
Figure 45:
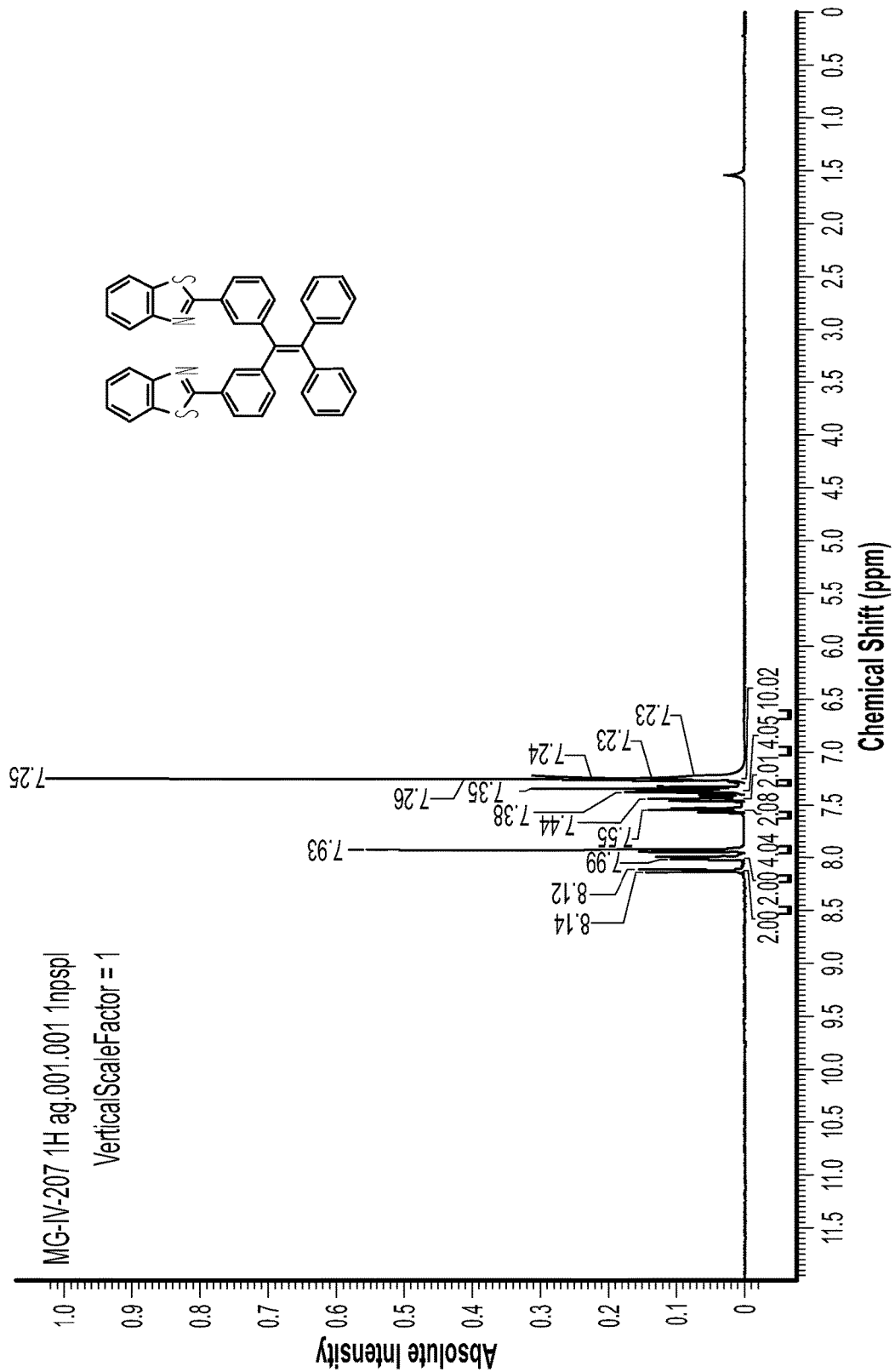
Figure 45:
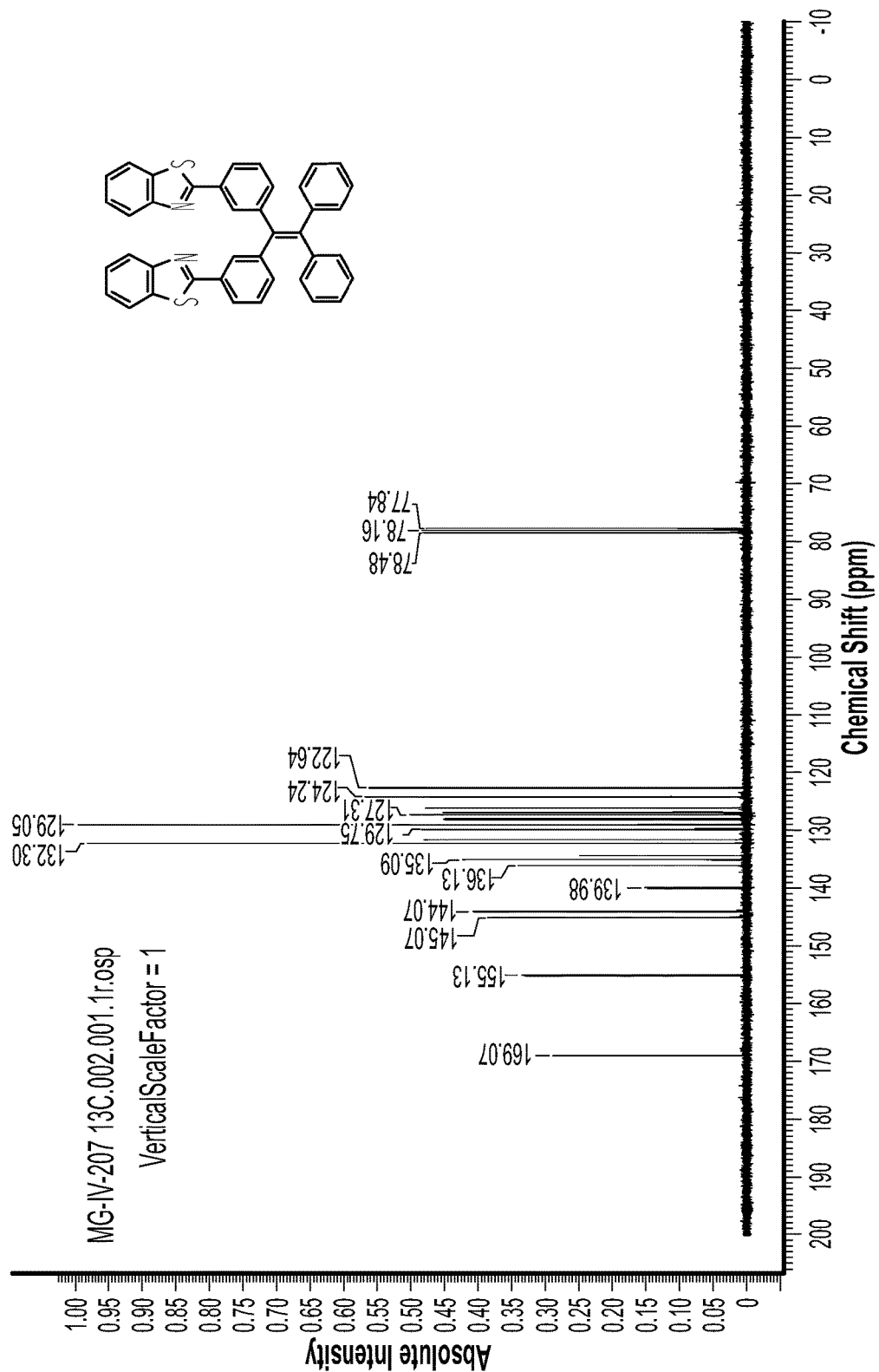
Figure 45:
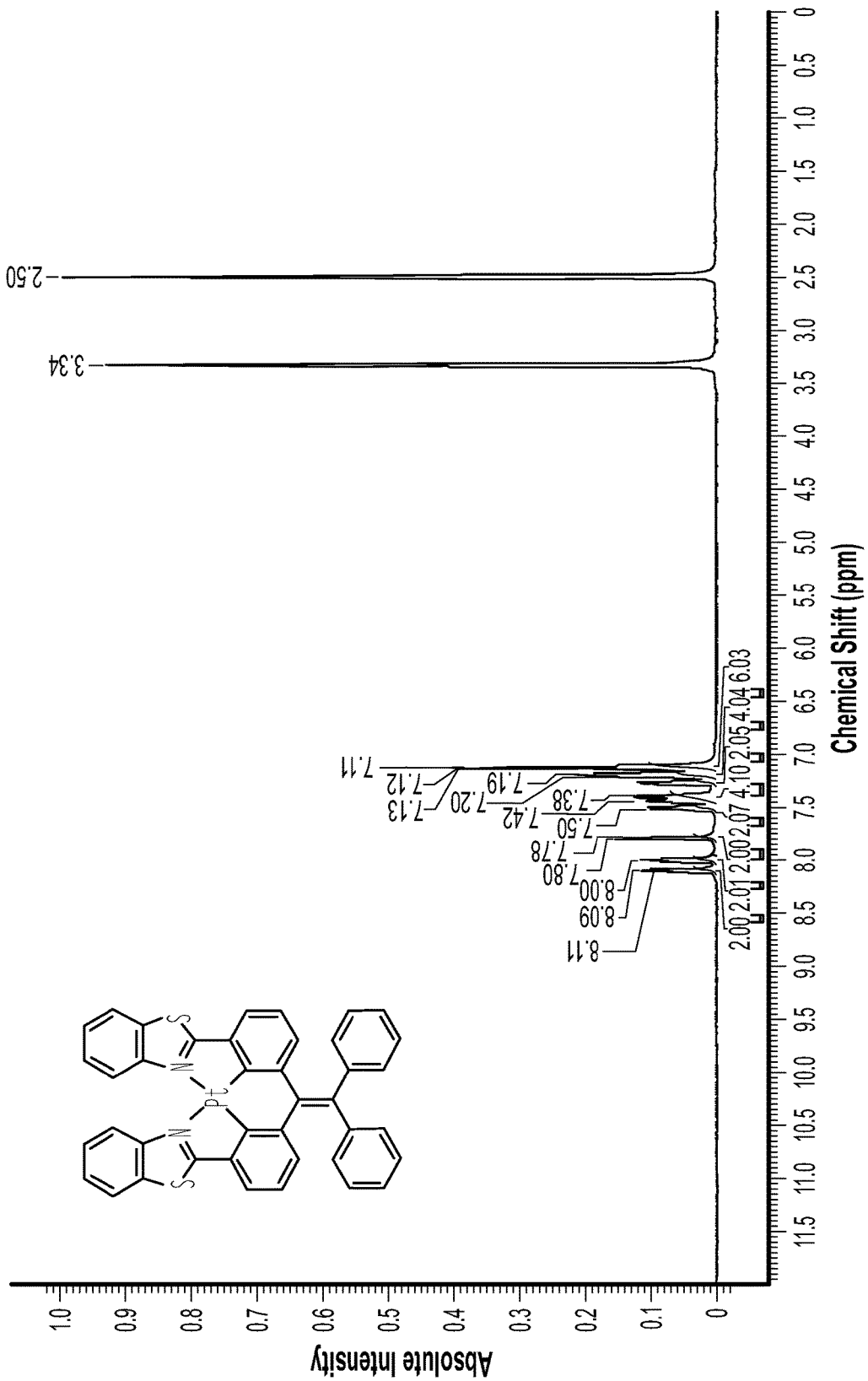
Figure 45:
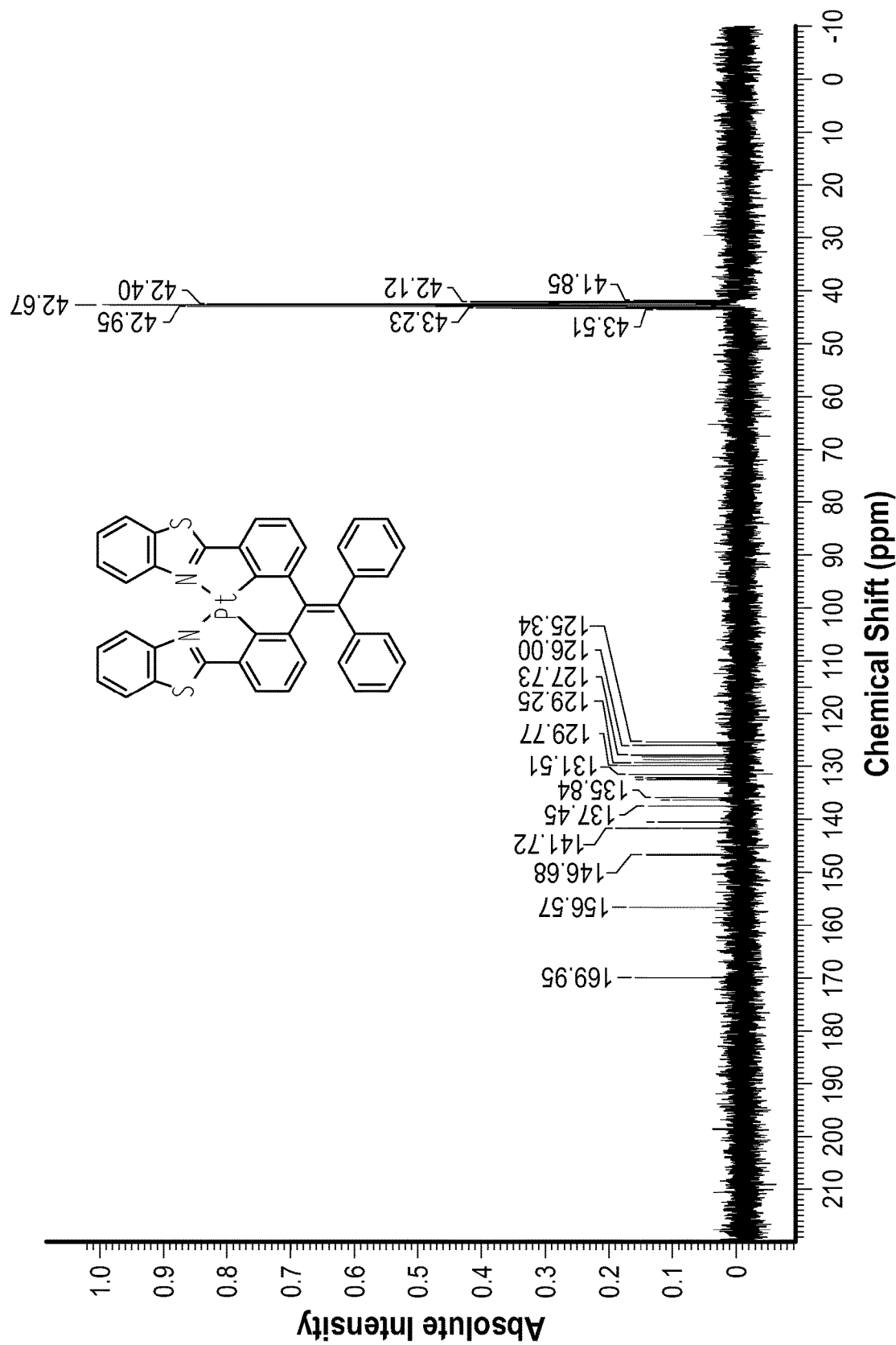
Figure 45:
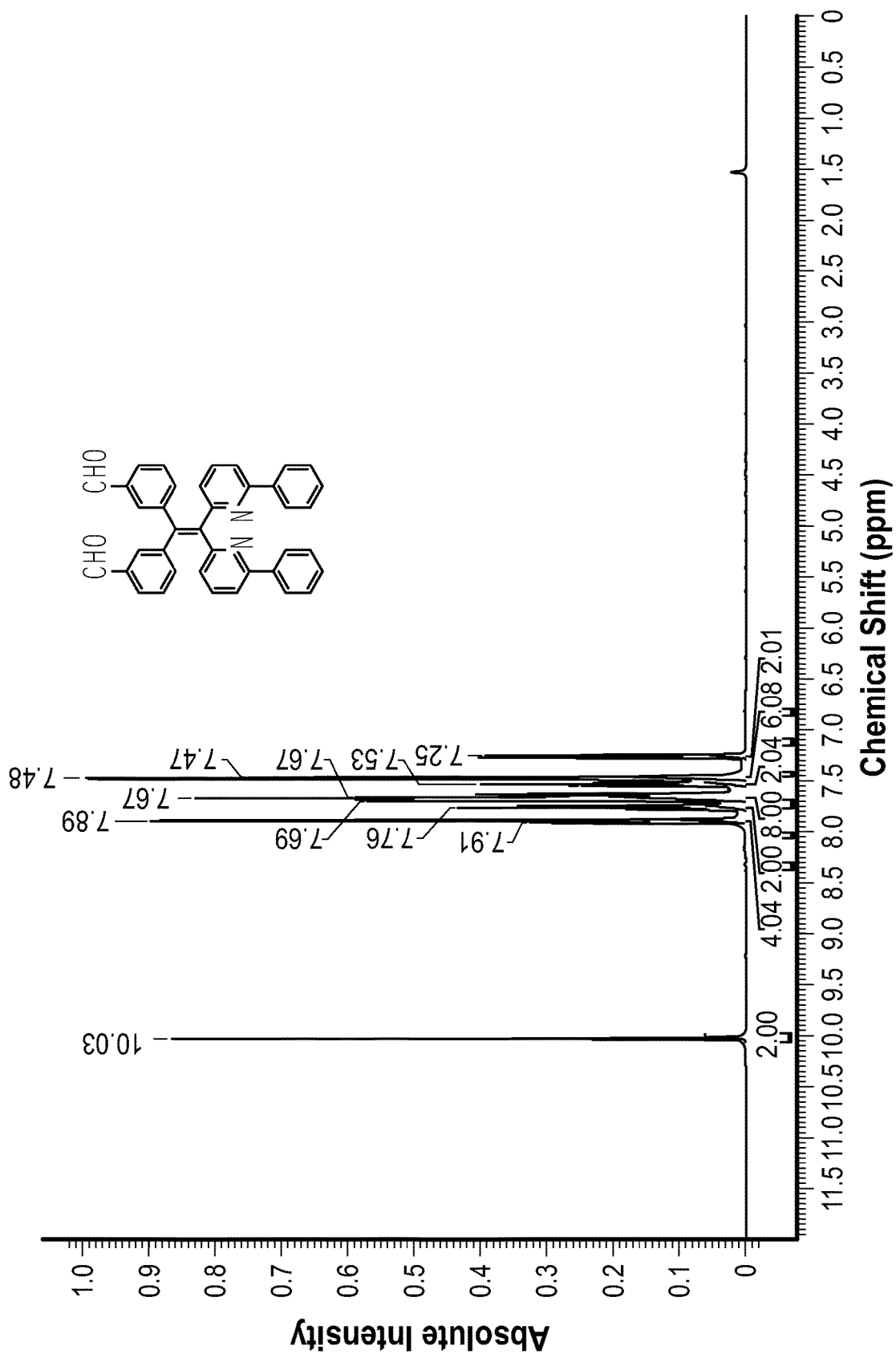
Figure 45:
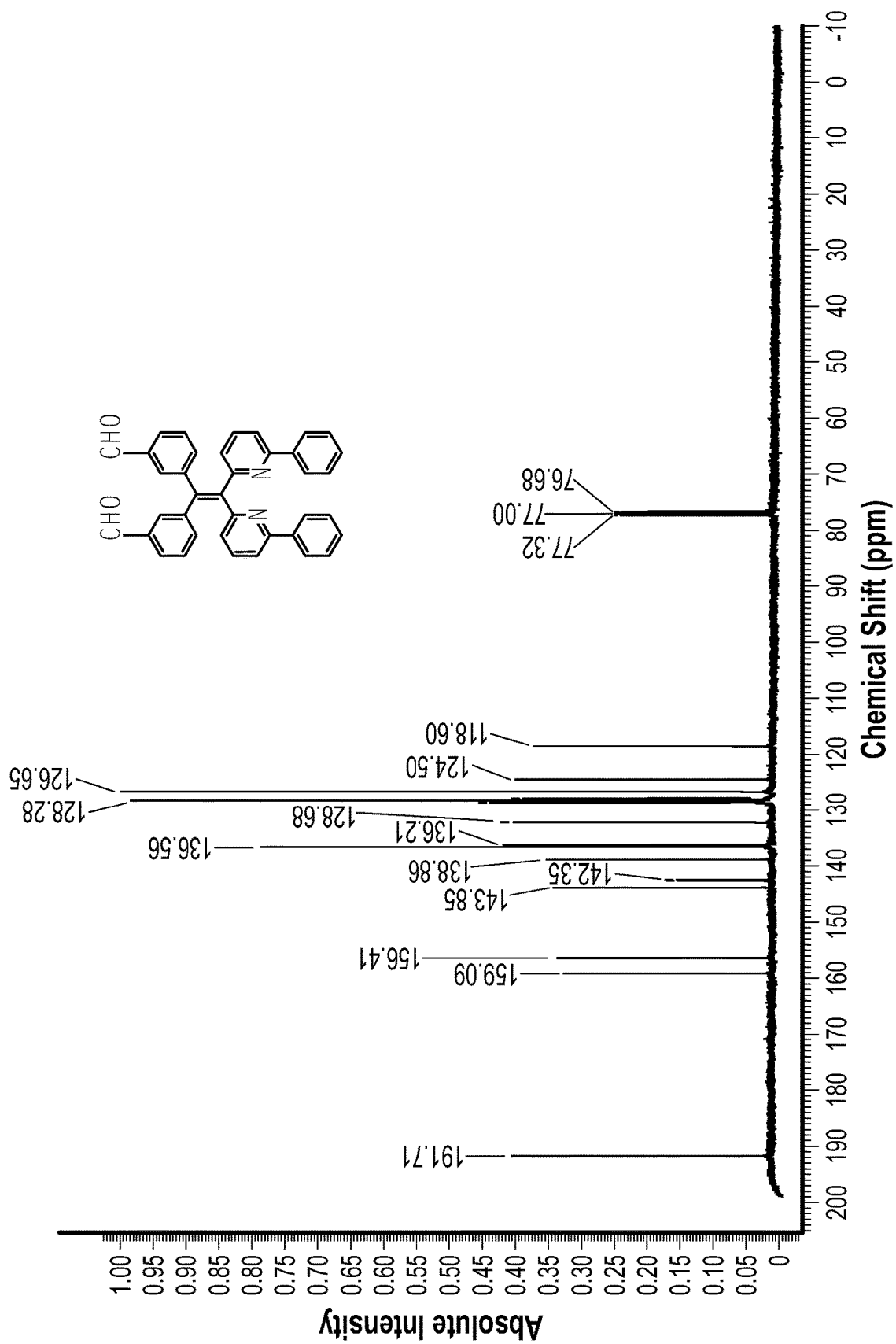
Figure 45:
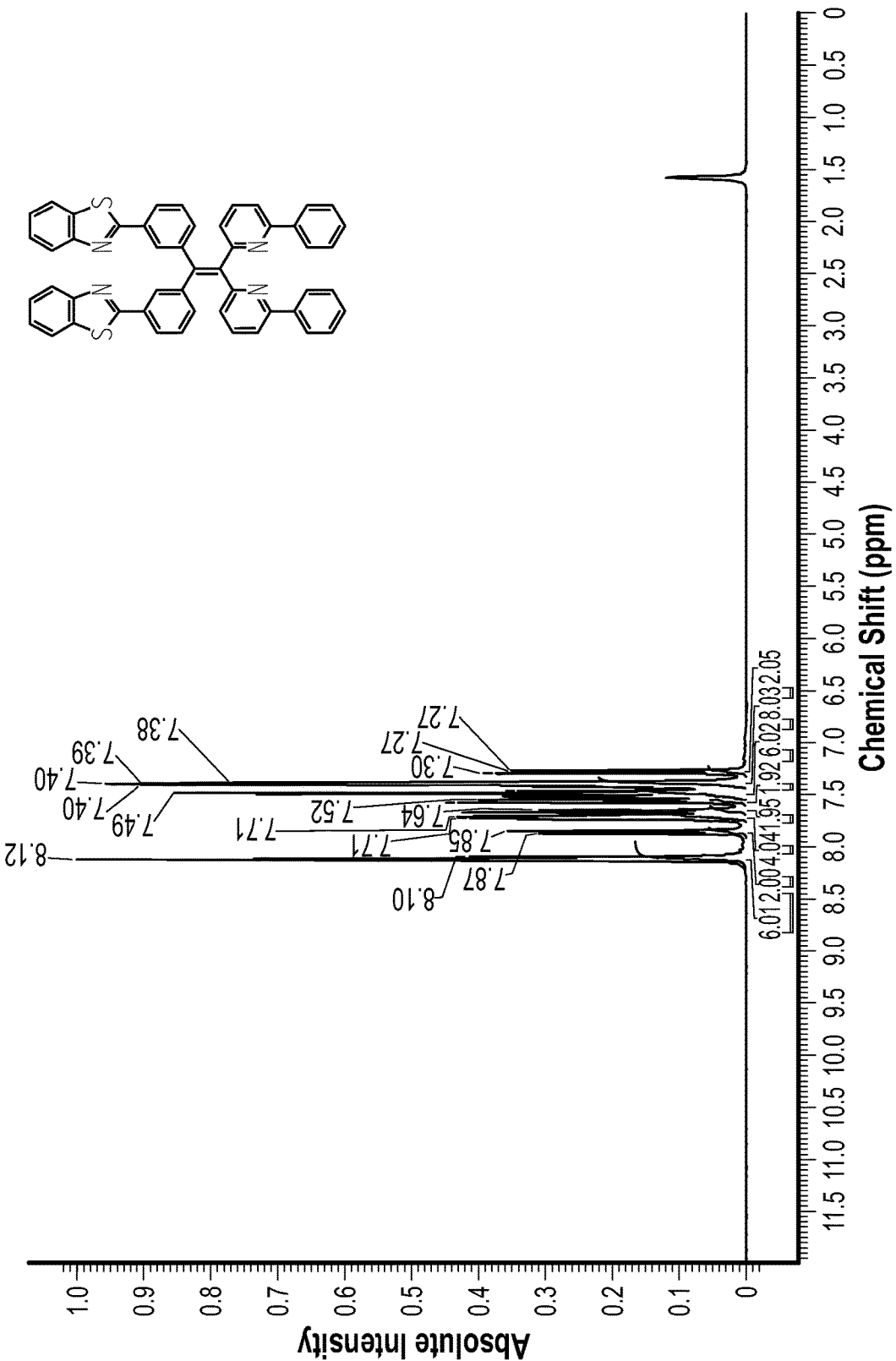
Figure 45:
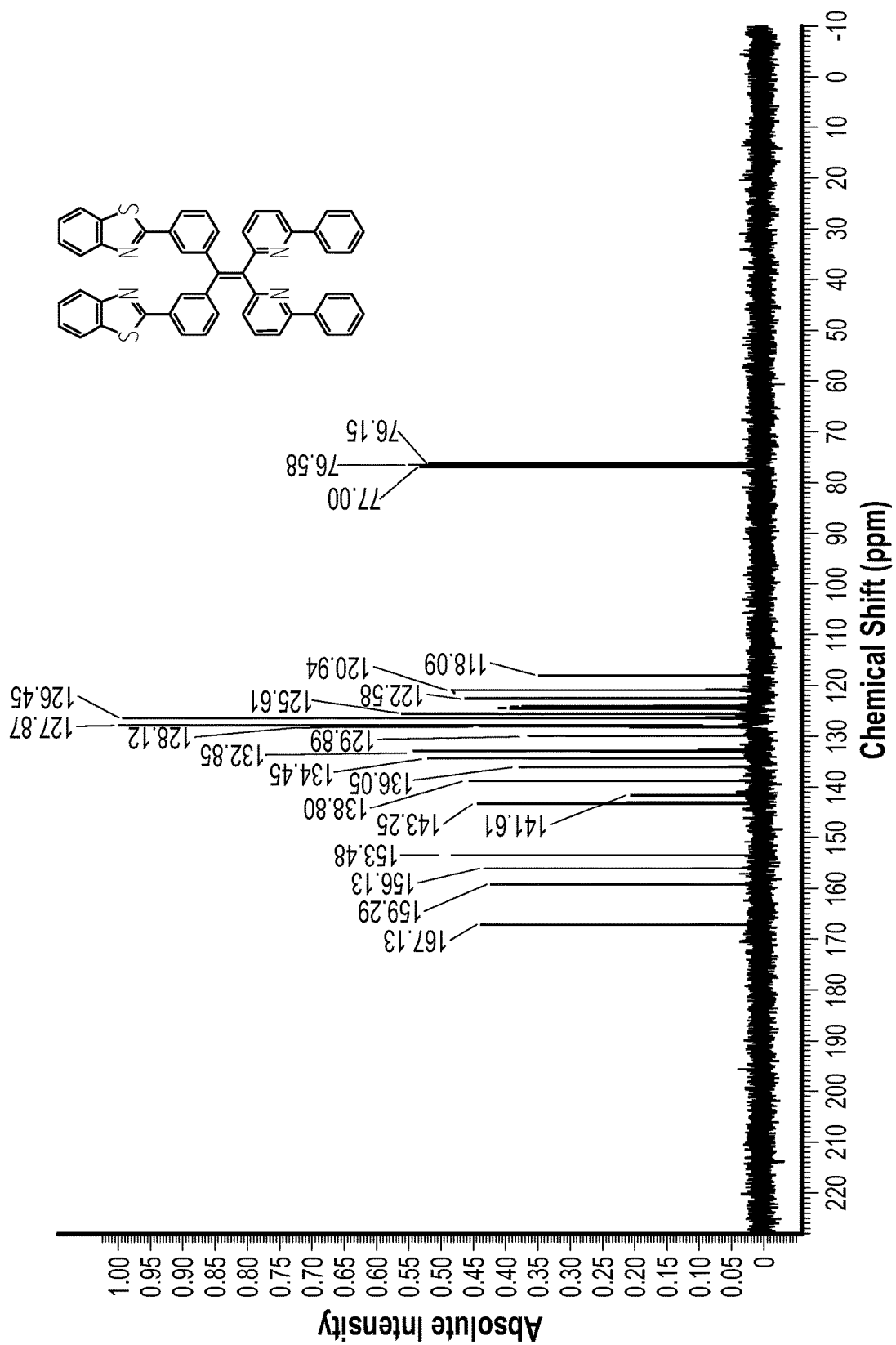
Figure 45:
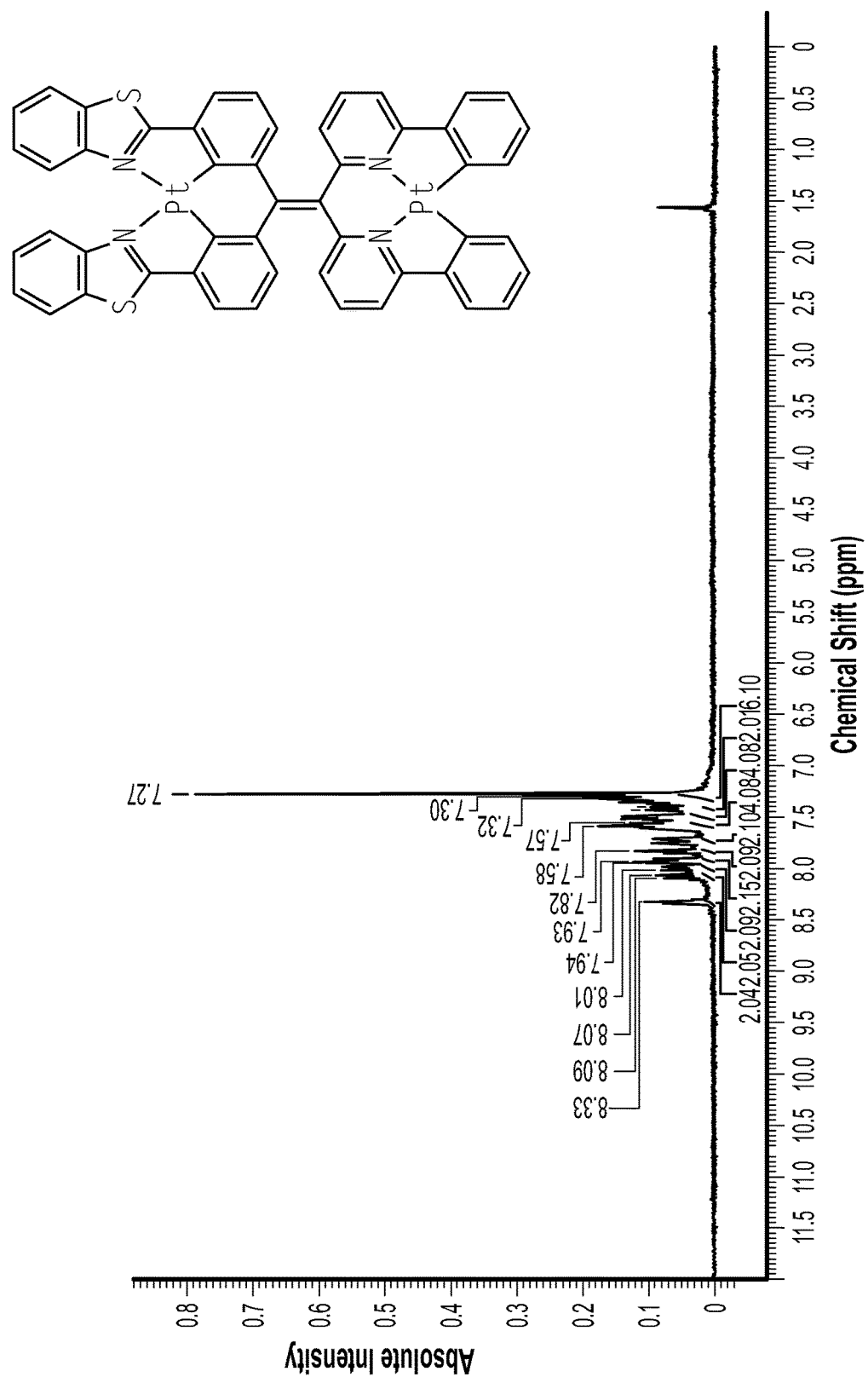
Figure 45:
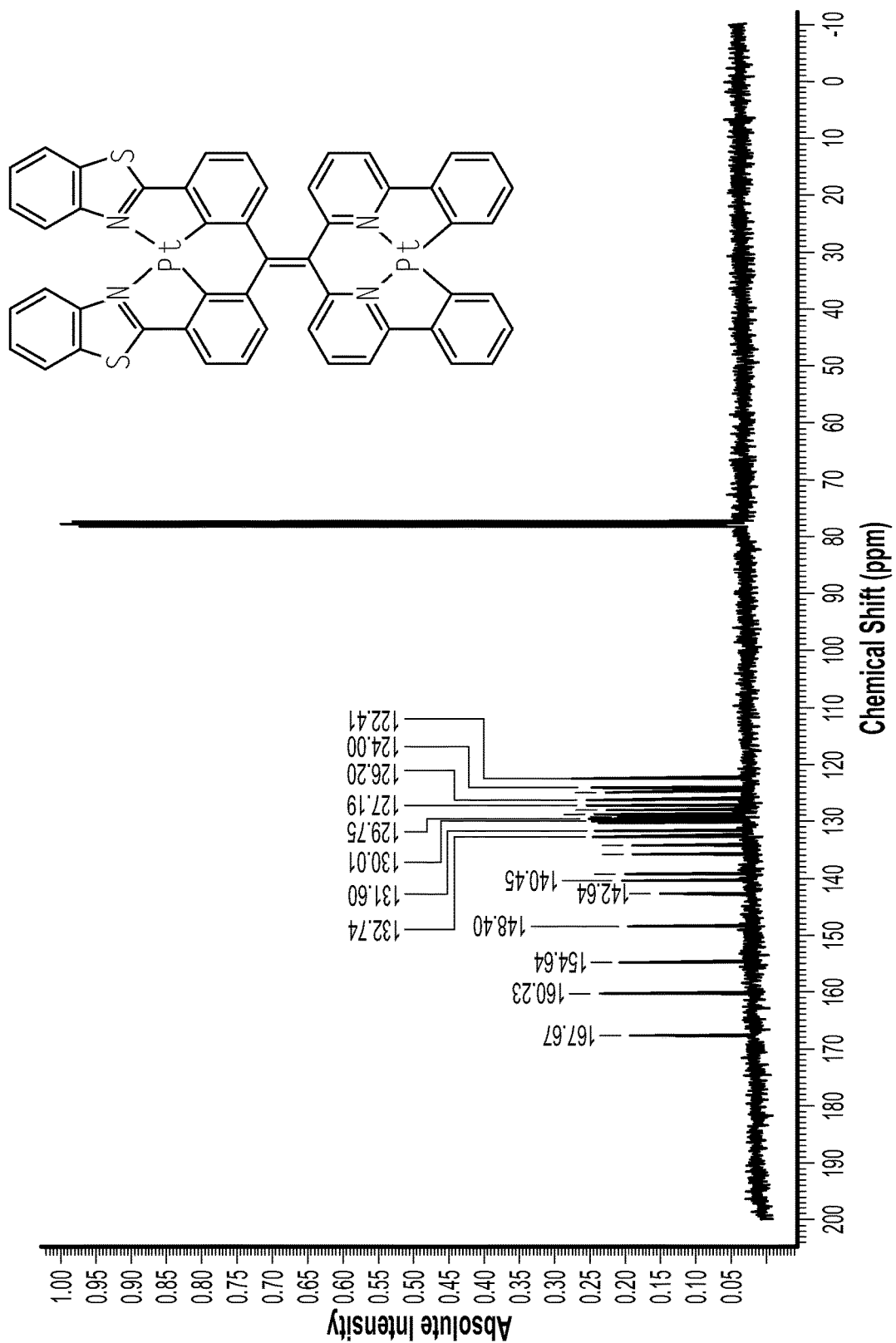
Figure 45:
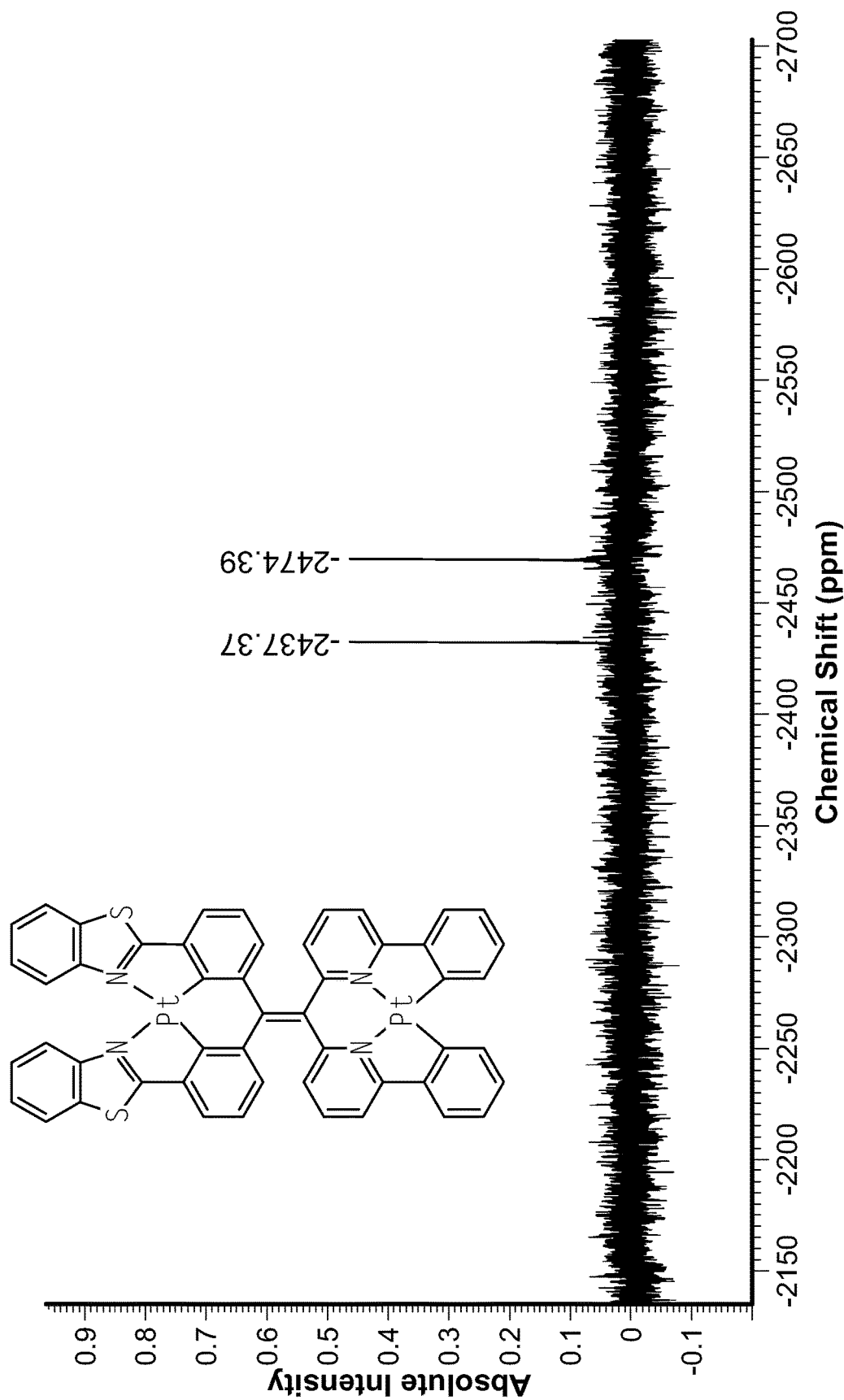

As a further test of this assay, the ability of 4/QIII DNA ensembles to identify DNAse I inhibitors also was examined. Identification of DNAse I inhibitors is attracting increasing attention as inhibition of DNAse I may exert tissue-protective effects against necrosis and radiation injury (Basnakian, et al., *J. Am. Soc. Nephrol.* 2005, 16, 697-702; Kolarevic, et al., *Eur. J. Med. Chem.* 2014, 88, 101-111 and Apostolov, et al., *Radiat. Res.* 2009, 172, 481-492). In addition, DNAse I inhibitors are proposed to be effective in the treatment of male infertility through prevention of sperm DNA fragmentation (Illic, et al., *Biochem. Biophys. Res. Commun.* 2018, 498, 1073-1077). The inhibitor assay was performed by monitoring the NIR emission intensity of 4/QIII DNA in the presence of DNAse I and varying concentrations of three known DNAse I inhibitors: EDTA, JR-132 (1,4-phenylene-bis-aminoguanidine hydrochloride), and $ZnCl_2$. Inhibitor $IC_{50}$ values were determined from plots of log[inhibitor] vs NIR emission intensity (FIGS. 41-43). Experimentally calculated $IC_{50}$ values for the three inhibitors (EDTA—202 μM, JR-132-2.29 μM, $ZnCl_2$-20.7 μM) are all in excellent agreement with previously reported values (Table S3) (Jang, et al., *J. Biomol. Screen.* 2015, 20, 202-211). Thus, the 4/QIII DNA luminescence assay is effective for direct determination of DNAse I activity and detection/quantification of DNAse I inhibition.

In summary, a new G quadruplex-based luminescence assay was developed for sensitive, label-free, rapid and real-time detection of DNAse I activity and inhibition. The developed assay is the most sensitive of any luminescence-based assay available for DNAse I activity and has further advantages of HTS compatibility and cost efficiency. A structurally novel and neutral diplatinum(II) complex (4) has been easily prepared via cyclometalation of a bis(pyridyl)-bis(benzothiazole) tetraarylethylene derivative. The complex exhibits switchable near-IR luminescence at 785 nm as a function of solvent-induced aggregation. Association of 4 with DNA was found to result in varying degrees of NIR emission quenching as a function of DNA structure, and complete luminescence quenching was observed in the presence of G-quadruplex DNA derived from the human c-myc oncogene. Subsequent DNA degradation liberates 4 which then self-assembles to produce a turn-on luminescence signal. The switchable NIR emission of this 4/DNA ensemble was successfully used to develop a fast (10 min), sensitive (LOD=0.002 U/mL), and label-free assay for the endonuclease DNAse I that possesses distinct advantages over all previously reported DNAse I assays. Furthermore, the assay can be easily modified to allow screening for DNAse I inhibitors. Assay experiments were performed in multiwell plates and are compatible with high throughput screening techniques. Significantly, the suitability of this method for clinical use is demonstrated by utilizing 4/QIII DNA system for sensitive detection of DNAse I in human serum samples.

Finally, it is notable that the variable response of 4 based on DNA structure should enable further optimization of the system for different applications in biosensor technology. Moreover, the organometallic tetraarylethylene scaffold utilized in this study is representative of a versatile molecular framework well-suited for development of additional organic and metal-organic bioprobes for use in diverse chemical biology applications. In particular, the structural modification of the diplatinum complexes described here may ultimately facilitate use of these agents for in vivo monitoring of cellular events as activatable NIR luminescent probes.

Materials and Methods

All commercially available starting materials, reagents, and solvents were used as supplied unless otherwise stated. Reported yields are isolated yields. Proton ($^1H$) and carbon ($^{13}C$) NMR were collected on a Bruker NMR spectrometer at 300 MHz or 400 MHz for $^1H$ and 75 MHz or 100 MHz for $^{13}C$. Chemical shifts (δ) are reported in parts-per million (ppm) relative to residual undeuterated solvent. $^{195}Pt$ NMR was collected on a Bruker NMR spectrometer at 86 MHz and referenced externally against potassium tetrachloroplatinate(II) in $D_2O$. Melting points were recorded using a capillary melting point apparatus and are uncorrected. High resolution mass spectra were obtained in positive ion mode using electrospray ionization (ESI) on a double-focusing magnetic sector mass spectrometer or electron ionization time of flight mass spectroscopy (EI-TOF MS). Elemental analyses were performed using CE-440 Elemental Analyzer-Exeter Analytical, Inc. Particle size distribution analysis was measured by dynamic light scattering (DLS) using a Malvern Zetasizer Nano ZS instrument. Oligonucleotides were obtained from Integrated DNA Technologies (Coralville, IA). The G-quadruplexes from QI, QII and QIII were formed as previously described by heating the corresponding oligonucleotide solution (1 mM) in potassium phosphate buffer at 95° C. for 15 min and allowing the solution to equilibrate at room temperature overnight (Ang, D. L.; Harper, B. W. J.; Cubo, L.; Mendoza, O.; Vilar, R.; Aldrich-Wright, *J. Chem. Eur. J.* 2016, 22, 2317-2325). The synthesis and photophysical properties of platinum(II) complex 1 were previously reported (Gabr M. T.; Pigge, F. C. *Inorg. Chem.* 2018, 57, 12641-12649).

UV-Visible Spectroscopy. UV-visible spectra were obtained using quartz cuvettes on a Varian Cary 100-Scan dual-beam spectrophotometer. Each measurement was done in duplicate and compared to solvent blank. Blank samples were prepared using HPLC grade solvents.

Fluorescence Spectroscopy. Fluorescence spectra were obtained at room temperature using an Agilent Cary Eclipse fluorescence spectrophotometer in quartz cuvettes or white 96-well plates (Costar, Corning, NY). Each measurement was done in triplicate. Sample stock solutions were prepared in HPLC grade DMSO. DNA stock solutions were prepared in Tris buffer (50 mM NaCl, 2 mM Tris, pH 7.5).

General Procedure for Multiwell DNAse I Assay. A reaction mixture (total volume of 100 μL) containing 4 (4 μM) and QIII (8 μM) was prepared in 9:1 Tris buffer (10 mM Tris-HCl, 0.25 mM $MgCl_2$, 0.1 mM $CaCl_2$, pH 7.5):DMSO. Tris buffer was prepared using nuclease-free water. The reaction mixtures were prepared in white 96-well plates (Costar, Corning, NY) and incubated at room temperature for 2 min. Varying concentrations of DNAse I prepared in Tris buffer (10 mM Tris-HCl, 0.25 mM $MgCl_2$, 0.1 mM CaCl$_2$, pH 7.5) were added to the reaction mixture and incubated at room temperature for 10 min. Fluorescence spectra were obtained using Agilent Cary Eclipse fluorescence spectrophotometer, $\lambda_{ex}$=445 nm. NIR emission intensity at 785 nm was detected.

Lineweaver-Burk Plot. The assay was performed in multiwell plates as described in the general procedure above using a reaction mixture (100 µL) prepared from a starting solution of 4/QIII (4 and 8 µM, respectively, see General Procedure) diluted with buffer to obtain varying substrate concentrations of QIII (0, 0.25, 0.5, 1, 1.5, 2, 4 and 8 µM). DNAse I (4 U/mL) was added and mixtures were incubated at room temperature for 10 min. followed by fluorescence measurements. The initial digestion rates ($V_0$) were measured from time curves of digestion reactions.

Detection of DNAse I in Human Serum. Human serum from human male AB plasma was purchased from Sigma-Aldrich. DNAse I assay was performed as previously described. Different concentrations of DNAse I were prepared in human serum and added to reaction mixtures.

Determination of IC$_{50}$ Values of DNAse I Inhibitors. DNAse I assay was performed as previously described in the presence of DNAse I (4 U) and various concentrations of the inhibitor. Stock solutions of the inhibitors were prepared in Tris buffer (10 mM Tris-HCl, pH 7.5). The IC$_{50}$ values were calculated by plotting log[inhibitor] versus NIR emission intensity of 4. The dose-response curves were analyzed by nonlinear regression using GraphPad Prism 8.0 (GraphPad Software, Inc., La Jolla, CA, USA).

Saturation binding isotherm. The interaction between 4 and DNA was quantified by measuring the change in NIR emission intensity of 4 (4 µM) in the presence of various concentrations of DNA (0-18 µM). The experiment was performed in triplicate with results given as the mean±SD. The fraction of 4 bound to DNA was plotted versus DNA concentration to yield binding isotherms. The fraction of 4 bound to DNA at each point of the titration was calculated following the changes of emission intensity at 785 nm, using the following equation (Petraccone, L.; et al. *Biochimie* 2011, 93, 1318-1327):

Fraction of 4 bound to DNA=$(I_{785}-I_{free})/(I_{bound}-I_{free})$

Where $I_{785}$: NIR emission intensity at 785 nm at the different molar ratios (4/DNA) investigated.

$I_{free}$: NIR emission intensity at 785 nm of 4 in the absence of DNA.

$I_{bound}$: NIR emission intensity at 785 nm of saturated sample of 4 with DNA.

The corresponding binding isotherms were analysed by GraphPad Prism 8.0 (GraphPad Software, Inc., La Jolla, CA, USA) by non-linear regression using a one site binding equation. The dissociation constants ($K_d$) values were calculated using the following equation (Hein, P. et al. Receptor and Binding Studies in Practical Methods in Cardiovascular Research (Eds.: S. Dhein, F. W. Mohr, M. Delmar), Springer, Berlin, Heidelberg, 2005, pp. 723-783):

$$Y=B_{max}*X/(K_d+X)$$

where, X is the concentration of 4, Y is change in emission intensity, Bmax is the maximum specific binding.

Validation of the assay for high-throughput screening (HTS). The suitability of the assay for HTS was validated by calculating three screen parameters (signal-to-noise ratio (S/N), signal-to-background ratio (S/B) and Z' factor) using the following equations (Zhang, J.-H. et al. *J. Biomol. Screen.* 1999, 4, 67-73):

$$S/N = \frac{\text{mean signal of +ve control} - \text{mean background}}{\text{standard deviation of background}}$$

$$S/B = \frac{\text{mean signal of +ve control}}{\text{mean background}}$$

$$Z' \text{factor} = 1 - \frac{(S.D. +ve) + (S.D. -ve)}{(\text{mean} +ve) - (\text{mean} -ve)}$$

Where, S.D.+ve: Standard deviation of the positive control (i.e. in the presence of DNAse I)

S.D.−ve: Standard deviation of the negative control (i.e. in the absence of DNAse I)

Mean+ve: mean of the positive controls

Mean−ve: mean of the negative controls

Z' factor was calculated using 10 plates run in 96-well format. Each plate contained 40 positive controls (DNAse I was added) and 40 negative controls (DNAse I was not added).

UV-Melting Experiments. DNA melting temperature studies were carried out using quartz cells on an Agilent Cary Eclipse spectrophotometer equipped with a thermoprogrammer. Melting curves were monitored at 260 nm for dsDNA and 295 nm for QDNA with a heating rate of 2° C./min in the range of 24-98° C. Melting temperatures were obtained by plotting the temperature versus change in absorbance. The point of inflection of the heating curve was calculated using the first derivatives from which the melting temperature was obtained.

Experiments were performed in triplicate.

Tables

TABLE S1

Comparison of the developed DNAse I assay to other fluorescence-based DNAse I assays.

| Method | Limit of detection | Detection time (min) | Labeling | Signaling | Multi-well plate format |
|---|---|---|---|---|---|
| Graphene-based fluorescent assay[a] | 1.75 unit/ml | 8 | Labelling is required | Turn-on | No |
| Graphene-based fluorescent assay[b] | 1 unit/ml | 10 | Labelling is required | Turn-on | No |
| Self-quenched fluorescent reporter DNA[c] | Not determined | 25 | Labelling is required | Turn-on | Yes |
| Nano-graphene-based fluorescent assay[d] | 0.005 unit/ml | 40 | Labelling is required | Turn-on | No |
| Malachite green dye/ G-quadruplex[e] | 1 unit/ml | 180 | Label-free | Turn-off | No |
| DNA-templated gold/silver nanoclusters[f] | 1.5 unit/ml | 30 | Label-free | Turn-off | No |
| DNA-templated silver nanocluster/ graphene oxide nanocomposite[g] | 0.1 unit/ml | 150 | Label-free | Turn-on | Yes |
| dsDNA coupled with PicoGreen[h] | 5 pg | 60 | Label-free | Turn-on | Yes |
| FRET dsDNA probe[i] | 40 unit/L | 20 | Labelling is required | Turn-on | No |

TABLE S1-continued

Comparison of the developed DNAse I assay to other fluorescence-based DNAse I assays.

| Method | Limit of detection | Detection time (min) | Labeling | Signaling | Multi-well plate format |
|---|---|---|---|---|---|
| DNAseAlert ™ QC system[j] | 0.005 unit | 30-60 | Labelling is required | Turn-on | Yes |
| This work | 0.002 unit/ml | 10 | Label-free | Turn-on | Yes |

[a]Zhou, Z.; Zhu, C.; Ren, J.; Dong, S. *Anal. Chim. Acta* 2012, 740, 88-92
[b]Xu, W.; Xie, Z.; Tong, C.; Peng, L.; Xiao, C.; Liu, X.; Zhu, Y.; Liu, B. *Anal. Bioanal. Chem.* 2016, 408, 3801-3809
[c]Jang, D. S.; Penthala, N. R.; Apostolov, E. O.; Wang, X.; Fahmi, F.; Crooks P. A.; Basnakian, A. G. *J. Biomol. Screen.* 2015, 20, 202-211
[d]Zhao, C.; Chen, Y.; Fang, J.; Fan, J.; Tong, C.; Liu, X.; Liu B.; Wang, W. *RSC Adv.* 2017, 7, 30911-30918
[e]Sun, S.-K.; Wang B.-B.; Yan, X.-P. *Analyst* 2013, 138, 2592-2597
[f]Dou, Y.; Yang, X. *Anal. Chim. Acta* 2013, 784, 53-58
[g]Lee, C. Y.; Park, K. S.; Jung Y. K.; Park, H. G. *Biosens. Bioelectron.* 2017, 93, 293-297
[h]Choi; S. J.; Szoka, F. C. *Anal. Biochem.* 2000, 281, 95-97
[i]Su, X.; Zhang, C.; Zhu, X.; Fang, S.; Weng, R.; Xiao, X.; Zhao, M. *Anal. Chem.* 2013, 85, 9939-9946
[j]DNAseAlert ™ QC system. https://www.thermofisher.com/order/catalog/product/AM1970 (Accessed on Jan. 27, 2019)

TABLE S2

Determination of DNAse I activity in diluted human serum.

| Added DNAse I (U/ml) | Measured DNAse I[a] (U/ml) | Coefficient of variation[c] (%) | % Recovery[d] |
|---|---|---|---|
| 0.15 | 0.16 (0.003)[b] | 1.87 | 106 |
| 0.5 | 0.48 (0.01) | 2.08 | 96 |
| 1 | 1.09 (0.04) | 3.66 | 109 |
| 4 | 3.88 (0.07) | 1.8 | 97 |

[a]Mean value of three measurements.
[b]Standard deviation (SD) for measured DNAse I (n = 3).
[c]Coefficient of variation = SD/mean × 100.
[d]% Recovery = Measured DNAse I/Added DNAse I × 100.

TABLE S3

Determination of $IC_{50}$ values of known DNAse I inhibitors.

| DNAse I inhibitor | $IC_{50}$ (μM) | Reported $IC_{50}$ (μM)[10] |
|---|---|---|
| EDTA | 202 ± 3.2 | 190 |
| JR-132 (1,4-phenylene-bis-aminoguanidine hydrochloride)[a] | 2.29 ± 0.2 | 2.73 |
| $ZnCl_2$ | 20.7 ± 0.4 | 18 |

[a]Ring, J. R.; Zheng, F.; Haubner, A. J.; Littleton J. M.; Crooks, P. A. *Bioorg. Med. Chem.* 2013, 21, 1764-1774

All publications, patents, and patent documents are incorporated by reference herein, including Gabr et al., *Molecules* 2019, 24, 4390, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula (Ia) or (Ib):

GGGGTTTTGGGGGGGTTTTGGG,  (SEQ ID NO: 1)

AGGGTTAGGGTTAGGGTTAGGG,  (SEQ ID NO: 2)

or

TGAGGGTGGGTAGGGTGGGTAA.  (SEQ ID NO: 3)

wherein:
A, B, C, D, E, F, J and K are aryl or heteroaryl;
L, M, Q and V are selected from the group consisting of S, O, and N; provided 2 and only 2 of the 4 are nitrogen;
X, Y, W and Z are selected from the group consisting of S, O, and N; provided 2 and only 2 of the 4 are nitrogen;
wherein CWXAEQLJ is a mirror image of DZYBFVMK and CWXAE is a mirror image of DZYBF;
or a salt thereof.

2. The compound or salt of claim 1, wherein C, D, J and K are each benzothiazolyl.

3. The compound or salt of claim 1, wherein A, B, E and F are each pyridyl.

4. The compound or salt of claim 1, which is a compound of formula (Ia), wherein A and B, or C and D, or E and F, or J and K, or A and D, or B and C, or J and F, or E and K are each phenyl.

5. The compound or salt of claim 2, which is a compound of formula (Ib), wherein E and F are each phenyl, anthracenyl, pyrenyl, or naphthyl.

6. The compound or salt of claim 1, which is a compound of formula (Ia), wherein L and M, or Q and V, or L and V, or Q and M are each carbon.

7. The compound or salt of claim 1, which is a compound of formula (Ia), wherein L and M, or Q and V, or L and V, or Q and M are each a heteroatom.

8. The compound or salt of claim 7, which is a compound of formula (Ia), wherein L and M, or Q and V, or L and V, or Q and M are each nitrogen.

9. The compound or salt of claim 1, wherein X and Y, or W and Z, or X and Z, or W and Y are each nitrogen.

10. The compound or salt of claim 1, wherein X and Y, or W and Z, or X and Z, or W and Y are each carbon.

11. A compound selected from a group consisting of:

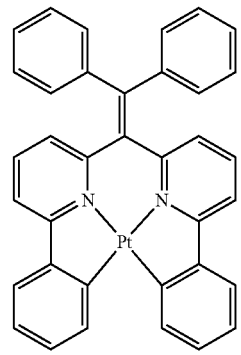

1

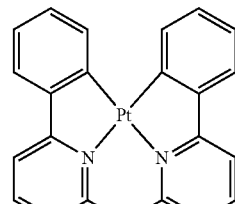

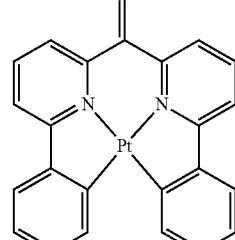

2

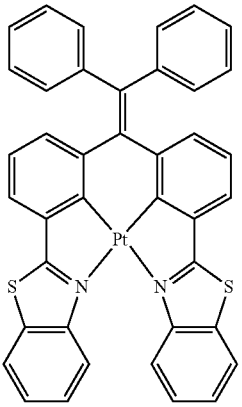

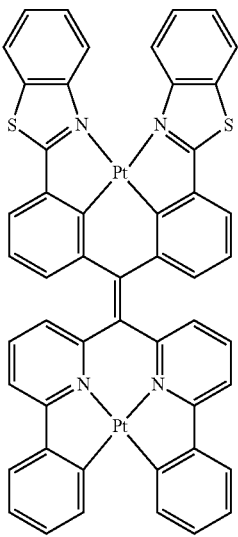

and

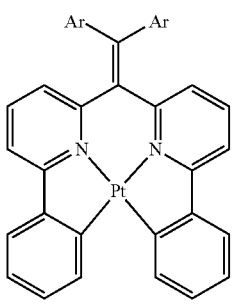

wherein each of Ar is independently

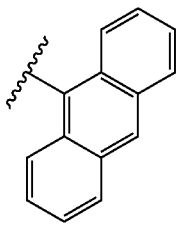

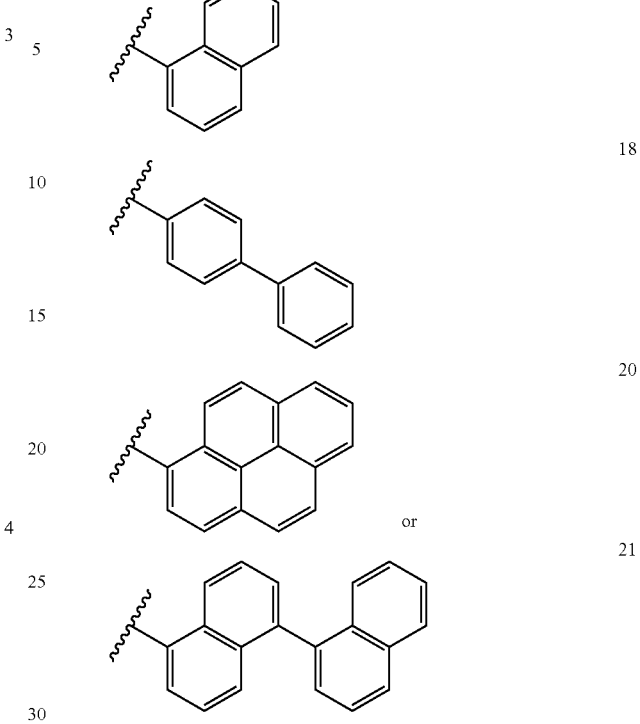

or a salt thereof.

12. A composition comprising 1) a plurality of compounds of formula (Ia), (Ib) or salts thereof as described claim 1; and 2) at least one DNA oligonucleotide.

13. The composition of claim 12, wherein the at least one DNA oligonucleotide comprises a sequence having at least 80% sequence identity to: GGGGTTTTGGGGGGGTTTTGGG (SEQ ID NO:1), AGGGTTAGGGTTAGGGTTAGGG (SEQ ID NO:2), or TGAGGGTGGGTAGGGTGGGTAA (SEQ ID NO:3).

14. The composition of claim 12, wherein the at least one DNA oligonucleotide comprises a sequence TGAGGGTGGGTAGGGTGGGTAA (SEQ ID NO:3).

15. A method of detecting the presence of DNAse I in a test sample, the method comprising:
  1) contacting a composition as described in claim 12 with the test sample to provide a first reaction mixture; and
  2) measuring the NIR emission intensity of the first reaction mixture, wherein an increase in the NIR emission intensity as compared to a control correlates with the presence of DNAse I in the test sample.

16. A method of detecting the presence of DNAse I in a test sample, the method comprising:
  1) measuring the NIR emission intensity of a composition as described in claim 12;
  2) contacting the composition with the test sample to provide a first reaction mixture; and
  3) measuring the NIR emission intensity of the first reaction mixture, wherein an increase in the NIR emission of the first reaction mixture as compared to the NIR emission intensity of the composition correlates with the presence of DNAse I in the test sample.

17. A method of identifying a DNAse I inhibitor, the method comprising:
  1) contacting a composition as described in claim 12, DNAse I and a test compound to provide a first reaction mixture;

2) measuring the NIR emission intensity of the first reaction mixture; and
3) identifying the test compound as a DNAse I inhibitor when a decrease in the NIR emission intensity is detected as compared to a control.

18. A method of identifying a DNAse I inhibitor, the method comprising:
1) contacting a composition as described in claim 12 and DNAse I to provide a first reaction mixture;
2) measuring the NIR emission intensity of the first reaction mixture;
3) contacting a composition as described in any one of claims 14, DNAse I and the test compound to provide a second reaction mixture;
4) Measuring the NIR emission intensity of the second reaction mixture; and
5) identifying the test compound as a DNAse I inhibitor when the NIR emission intensity of the second reaction mixture is less than the NIR emission intensity of the first reaction mixture.

19. A kit comprising:
1) a plurality of compounds of formula (Ia), (Ib) or salts thereof as described in claim 1;
2) G-quadruplex DNA; and
3) instructions for detecting the presence of DNAse I in a test sample or identifying a DNAse I inhibitor, using the plurality of compounds of formula (Ia), (Ib) or salts thereof, and the G-quadruplex DNA.

* * * * *

UNITED STATES PATENT AND TRADEMARK OFFICE
CERTIFICATE OF CORRECTION

PATENT NO. : 11,851,447 B2
APPLICATION NO. : 16/814423
DATED : December 26, 2023
INVENTOR(S) : Christopher Pigge and Moustafa Tarek Ahmed Ibrahim Gabr Page 1 of 1

It is certified that error appears in the above-identified patent and that said Letters Patent is hereby corrected as shown below:

In the Claims

Column 45, Lines 27-36, Claim 1, please delete

GGGGTTTTGGGGGGGTTTTGGG, (SEQ ID NO, 1)

AGGGTTAGGGTTAGGGTTAGGG, (SEQ ID NO, 2)
or

"TGAGGGTGGGTAGGGTGGGTAA." (SEQ ID NO, 3) " and insert

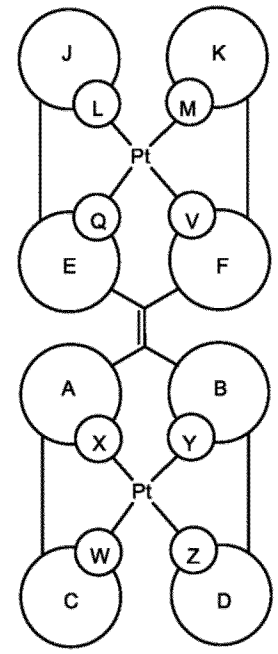  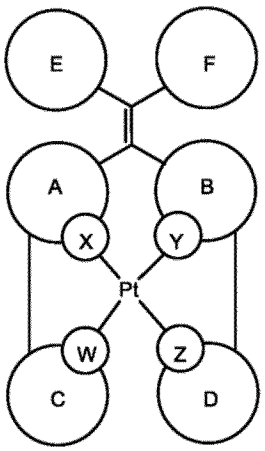

--   Ia                Ib                -- therefor.

Signed and Sealed this
Twenty-sixth Day of March, 2024

Katherine Kelly Vidal
*Director of the United States Patent and Trademark Office*